United States Patent
Lee et al.

(10) Patent No.: US 11,958,844 B2
(45) Date of Patent: Apr. 16, 2024

(54) 1,3,4-OXADIAZOLE DERIVATIVE COMPOUNDS AS HISTONE DEACETYLASE 6 INHIBITOR, AND PHARMACEUTICAL COMPOSITION COMPRISING THE SAME

(71) Applicant: Chong Kun Dang Pharmaceutical Corp., Soul (KR)

(72) Inventors: Chang Sik Lee, Gyeonggi-do (KR); Jung Taek Oh, Gyeonggi-do (KR); Hokeun Yun, Gyeonggi-do (KR); Hyeseung Song, Gyeonggi-do (KR); Hyunjin Michael Kim, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 665 days.

(21) Appl. No.: 17/263,333

(22) PCT Filed: Jul. 25, 2019

(86) PCT No.: PCT/KR2019/009228
§ 371 (c)(1),
(2) Date: Jan. 26, 2021

(87) PCT Pub. No.: WO2020/022794
PCT Pub. Date: Jan. 30, 2020

(65) Prior Publication Data
US 2021/0188831 A1 Jun. 24, 2021

(30) Foreign Application Priority Data
Jul. 26, 2018 (KR) .................. 10-2018-0087455

(51) Int. Cl.
*C07D 413/14* (2006.01)
*C07D 413/04* (2006.01)
*C07D 417/14* (2006.01)

(52) U.S. Cl.
CPC ......... *C07D 413/14* (2013.01); *C07D 413/04* (2013.01); *C07D 417/14* (2013.01)

(58) Field of Classification Search
CPC .................................................. C07D 413/04
See application file for complete search history.

(56) References Cited

U.S. PATENT DOCUMENTS

| | | | |
|---|---|---|---|
| 4,871,753 A | 10/1989 | Rorh | |
| 8,901,156 B2 | 12/2014 | Baloglu | |
| 8,981,084 B2 | 3/2015 | Baloglu | |
| 9,670,193 B2 | 6/2017 | Hebach et al. | |
| 10,464,911 B2 | 11/2019 | Lee et al. | |
| 10,494,355 B2 | 12/2019 | Kim et al. | |
| 10,538,498 B2 | 1/2020 | Lee et al. | |
| 10,584,117 B2 | 2/2020 | Lee et al. | |
| 10,717,716 B2 | 6/2020 | Lee et al. | |
| 2005/0288282 A1 | 12/2005 | Delorme et al. | |
| 2006/0058298 A1 | 3/2006 | Delorme et al. | |
| 2007/0293530 A1 | 12/2007 | Smil et al. | |
| 2012/0027874 A1 | 2/2012 | Charrier et al. | |
| 2012/0289495 A1 | 11/2012 | Baloglu et al. | |
| 2013/0059883 A1 | 3/2013 | Baloglu et al. | |
| 2014/0005133 A1 | 1/2014 | Trivedi et al. | |
| 2014/0005164 A1 | 1/2014 | Varrone et al. | |
| 2014/0142105 A1 | 5/2014 | Hebach et al. | |
| 2014/0329825 A1 | 11/2014 | Hebach et al. | |
| 2015/0307497 A1 | 10/2015 | Sugimoto et al. | |
| 2016/0244449 A1 | 8/2016 | Lu et al. | |
| 2017/0015809 A1 | 1/2017 | Hawkins et al. | |
| 2017/0145012 A1 | 5/2017 | Buckmelter et al. | |
| 2018/0215743 A1 | 8/2018 | Lee et al. | |
| 2018/0230113 A1 | 8/2018 | Lee et al. | |
| 2018/0230114 A1 | 8/2018 | Lee et al. | |
| 2018/0251437 A1 | 9/2018 | Lee et al. | |

(Continued)

FOREIGN PATENT DOCUMENTS

| | | |
|---|---|---|
| CN | 101263121 | 9/2008 |
| CN | 102802623 | 11/2012 |

(Continued)

OTHER PUBLICATIONS

Office Action for Korean Appln, No. 10-2020-0065508, dated Mar. 2, 2022, 15 pages (with Machine Translation).
Cancer [online], "Cancer," Jun. 27, 2007, retrieved on Jul. 6, 2007, retrieved from URL <http://www.nlm.nih.gov/mededlineplus/cancer. html>, 10 pages.
CAS No. 904635-69-4, "4-Morpholinecarboxamide, N-[4-[5-(trifluoromethyl)-1,3,4-oxadiazol-2-yl]phenyl]," STN Easy, dated Aug. 25, 2006, 1 page.
CAS No. 904652-71-7, "4-Morpholinecarboxamide, N-[4-[5-(dichloromethyl)-1,3,4-oxadiazol-2-yl]phenyl]," STN Easy, dated Aug. 25, 2006, 1 page.

(Continued)

*Primary Examiner* — Matthew P Coughlin
*Assistant Examiner* — Meghan C Heasley
(74) *Attorney, Agent, or Firm* — Fish & Richardson P.C.

(57) ABSTRACT

The present invention relates to novel compounds having a histone deacetylase 6 (HDAC6) inhibitory activity, optical isomers thereof or pharmaceutically acceptable salts thereof, a pharmaceutical use thereof, and a method for preparing the same. According to the present invention, the novel compounds, optical isomers thereof or pharmaceutically acceptable salts thereof have the histone deacetylase 6 (HDAC6) inhibitory activity, and are effective in preventing or treating HDAC6-related diseases, comprising infectious diseases; neoplasm; internal secretion; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, and chromosomal aberration.

9 Claims, No Drawings

(56) References Cited

U.S. PATENT DOCUMENTS

| | | |
|---|---|---|
| 2018/0273495 A1 | 9/2018 | Kim et al. |
| 2019/0008836 A1 | 1/2019 | Kaieda et al. |
| 2021/0355089 A1 | 11/2021 | Chern et al. |
| 2023/0079386 A1 | 3/2023 | Lee et al. |
| 2023/0092890 A1 | 3/2023 | Lee et al. |

FOREIGN PATENT DOCUMENTS

| | | |
|---|---|---|
| CN | 103221047 | 7/2013 |
| CN | 103339111 | 10/2013 |
| CN | 104744446 | 7/2015 |
| CN | 103998446 | 11/2016 |
| CN | 108699048 | 10/2018 |
| EA | 201491060 | 9/2014 |
| EP | 0816356 | 1/1998 |
| EP | 3327019 A1 | 5/2018 |
| EP | 3330259 | 6/2018 |
| JP | H10-059962 | 3/1998 |
| JP | 2005513123 | 5/2005 |
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2013533279 | 8/2013 |
| JP | 2014513071 | 5/2014 |
| JP | WO 2014077401 | 5/2014 |
| JP | 2014520794 | 8/2014 |
| JP | 2014524922 | 9/2014 |
| JP | 2014533721 | 12/2014 |
| JP | 2014533734 | 12/2014 |
| JP | 2018511573 | 4/2018 |
| JP | 2018521110 | 8/2018 |
| JP | 2019504821 | 2/2019 |
| JP | 2021532130 | 11/2021 |
| JP | 2022529695 | 6/2022 |
| JP | 2022537904 | 8/2022 |
| KR | 100265385 | 11/2000 |
| KR | 100903743 | 6/2009 |
| KR | 101262870 | 5/2013 |
| KR | 101320198 | 10/2013 |
| KR | 20130112911 | 10/2013 |
| KR | 20140097459 | 8/2014 |
| KR | 20147017436 | 8/2014 |
| KR | 101561860 | 10/2015 |
| KR | 20170013186 | 2/2017 |
| KR | 10-2022-0012243 | 2/2022 |
| RU | 2515611 | 8/2012 |
| WO | WO 2003028729 | 4/2003 |
| WO | WO 2007011626 | 1/2007 |
| WO | WO 2007032445 | 3/2007 |
| WO | WO 2007093827 | 8/2007 |
| WO | WO 2007107758 | 9/2007 |
| WO | WO 2009010479 | 1/2009 |
| WO | WO 2010109148 | 9/2010 |
| WO | WO 2010123933 | 10/2010 |
| WO | WO 2010126002 | 11/2010 |
| WO | 2011011186 A2 | 1/2011 |
| WO | 2011091213 A2 | 7/2011 |
| WO | WO 2011088181 | 7/2011 |
| WO | WO 2011088192 | 7/2011 |
| WO | WO 2011104680 | 9/2011 |
| WO | WO 2011133888 | 10/2011 |
| WO | 2012011592 A1 | 1/2012 |
| WO | WO 2012013716 | 2/2012 |
| WO | WO 2012136492 | 10/2012 |
| WO | 2013008162 A1 | 1/2013 |
| WO | 2013041407 A1 | 3/2013 |
| WO | 2013052110 A1 | 4/2013 |
| WO | 2013066833 A1 | 5/2013 |
| WO | 2013066835 A2 | 5/2013 |
| WO | 2013066838 A1 | 5/2013 |
| WO | 2013066839 A2 | 5/2013 |
| WO | 2013080120 A1 | 6/2013 |
| WO | 2013134467 A1 | 9/2013 |
| WO | WO 2015033301 | 3/2015 |
| WO | WO 2015087151 | 6/2015 |
| WO | WO 2016082930 | 6/2016 |
| WO | WO 2016134320 | 8/2016 |
| WO | WO 2017014170 | 1/2017 |
| WO | 2017018804 A1 | 2/2017 |
| WO | 2017023133 A2 | 2/2017 |
| WO | WO 2017014321 | 2/2017 |
| WO | WO 2017018803 | 2/2017 |
| WO | WO 2017018805 | 2/2017 |
| WO | WO 2017065473 | 4/2017 |
| WO | 2017222951 A1 | 12/2017 |
| WO | 2017222952 A1 | 12/2017 |
| WO | WO-2017222951 A1 * | 12/2017 ............ A61K 45/06 |
| WO | WO 2018213364 | 11/2018 |
| WO | WO 2020022794 | 1/2020 |
| WO | WO 2020212479 | 10/2020 |
| WO | WO 2021127643 | 6/2021 |

OTHER PUBLICATIONS

CAS No. 904653-13-0, "4-Morpholinecarboxamide, N-[4-[5-(trichloromethyl)-1, 3,4-oxadiazol-2-yl]phenyl]," STN Easy, dated Aug. 25, 2006, 1 page.
Chemical Abstract compound RN No. 1355844-43-7, STN Express, dated Feb. 8, 2012, 1 page.
Chemical Abstract compound RN No. 1384673-31-7, STN Express, dated Jul. 27, 2012, 1 page.
Chemical Abstract compound RN No. 1436149-02-8, STN Express, dated Jun. 9, 2013, 1 page.
Chemical Abstract compound RN No. 1708354-35-1, STN Express, dated May 20, 2015, 1 page.
Chemical Abstract compound RN No. 1790675-44-3, STN Express, dated Jun. 29, 2015, 1 page.
Chemical Abstract compound RN No. 1798074-73-3, STN Express, dated Jul. 9, 2015, 1 page.
Chemical Abstract compound RN No. 904653-15-2, STN Express, dated Aug. 25. 2006, 1 page.
Chemical Abstract compound RN No. 904653-17-4, STN Express, Aug. 25, 2006, 1 page.
Chemical Abstract compound RN No. 904653-20-9, STN Express, dated Aug. 25, 2006, 2 pages.
Chemical Abstract compound RN No. 904653-21-0, STN Express, dated Aug. 25, 2006, 1 page.
Chemical Abstract compound RN No. 904653-22-1, STN Express, dated Aug. 25, 2006, 1 page.
Chen et al., "Computational exploration of zinc binding groups for HDAC inhibition," J. Org. Chem., May 2013, 78(10):5051-5055.
Chen et al., "Discovery of 2-methylpyridine-based biaryl amides as y-secretase modulators for the treatment of Alzheimer's disease, "Bioorg. Med. Chem, 2013, 23(23):6447-6454.
Decision to Grant in Russian Appln. No. 2021104625, dated Dec. 3, 2021, 29 pages (with English Translation).
El-Din et al., "Synthesis and in vitro antiproliferative activity of new 1,3,4-oxadiazole derivatives possessing sulfonamide moiety," Eur. J. Med. Chem, Jan. 2015, 90:45-52.
Extended European Search Report in European Appln. No. 16830836. 9, dated Dec. 19, 2018, 7 pages.
Extended European Search Report in European Appln. No. 16830837. 7, dated Dec. 17, 2018, 9 pages.
Extended European Search Report in European Appln. No. 16830838. 5, dated Nov. 19, 2018, 7 pages.
Extended European Search Report in European Appln. No. 16833369. 8, dated Apr. 1, 2019, 6 pages.
Golub et al., "Molecular Classification of Cancer: Class Discovery and Class Prediction by Gene Expression Monitoring," Science, Oct. 1991, 286:531-537.
International Preliminary Report on Patentability and Written Opinion for International Appln. No. PCT/KR2016/008214, dated Jan. 30, 2018, 8 pages.
International Preliminary Report on Patentability and Written Opinion for International Appln. No. PCT/KR2016/008216, dated Jan. 30, 2018, 9 pages.

(56) References Cited

OTHER PUBLICATIONS

International Preliminary Report on Patentability and Written Opinion for International Appln. No. PCT/KR2016/008218, dated Jan. 30, 2018, 8 pages.
International Preliminary Report on Patentability and Written Opinion for International Appln. No. PCT/KR2016/008622, dated Feb. 6, 2018, 8 pages.
International Preliminary Report on Patentability and Written Opinion for International Appln. No. PCT/KR2016/011355, dated Apr. 17, 2018, 6 pages.
International Search Report for International Appln. No. PCT/KR2016/008214, dated Nov. 24, 2016, 5 pages.
International Search Report for International Appln. No. PCT/KR2016/008216, dated Nov. 21, 2016, 12 pages (with English Translation).
International Search Report for International Appln. No. PCT/KR2016/008218, dated Nov. 21, 2016, 5 pages.
International Search Report for International Appln. No. PCT/KR2016/008622, dated Feb. 17, 2017, 5 pages.
International Search Report for International Appln. No. PCT/KR2016/011355, dated Jan. 26, 2017, 5 pages.
Lala et al., "Role of nitric oxide in tumor progression: Lessons from experimental tumors," Cancer Metastasis Rev., 1998, 17(1):91-106.
Manku, et al., "Synthesis and evaluation of lysine derived sulfamides as histone deacetylase inhibitors," Bioorg. Med. Chem. Lett., Feb. 2009, 19:1866-1870.
Murphy et al., "Regulation of the Dynamics of hsp90 Action on the Glucocorticoid Receptor by Acetylation/Deacetylation of the Chaperone," J. Biol. Chem., Oct. 2005, 280(40):33792-33799.
Office Action for Australian Appln. No. 2016299484, dated Aug. 28, 2018, 6 pages.
Office Action for Australian Appln. No. 2016299484, dated Dec. 18, 2018, 3 pages.
Office Action for Australian Appln. No. 2016299485, dated Sep. 13, 2018, 7 pages.
Office Action for Australian Appln. No. 2016299486, dated Jul. 21, 2018, 5 pages.
Office Action for Australian Appln. No. 2016303891, dated Nov. 16, 2018, 7 pages.
Office Action for Canadian Appln. No. 2987570, dated Oct. 18, 2018, 5 pages.
Office Action for Canadian Appln. No. 2993918, dated Dec. 4, 2018, 5 pages.
Office Action for Canadian Appln. No. 2993929, dated Dec. 4, 2018, 4 pages.
Office Action for Indian Appln. No. 201727037873, dated May 21, 2019, 7 pages.
Office Action for Indian Appln. No. 201817006324, dated Jun. 27, 2019, 6 pages.
Office Action for Japanese Appln. No. 2018-503804, dated Feb. 15, 2019, 4 pages (with English Translation).
Office Action for Japanese Appln. No. 2018-504096, dated Jan. 8, 2019, 5 pages (with English Translation).
Office Action for Japanese Appln. No. 2018-504720, dated Jan. 8, 2019, 19 pages (with English Translation).
Office Action for Japanese Appln. No. 2018-505725, dated Sep. 12, 2018, 3 pages.
Office Action for Japanese Appln. No. 2021-503874, dated Feb. 8, 2022, 7 pages (with English Translation).
Office Action for Korean Appln, No. 10-2016-0095332, dated May 9, 2017, 15 pages.
Office Action for Korean Appln, No. 10-2016-0095334, dated May 9, 2017, 17 pages.
Office Action for Korean Appln, No. 10-2016-0099508, dated May 9, 2017. 20 pages.
Office Action for Korean Appln, No. 10-2016-0131245, dated May 9, 2017, 7 pages.
Office Action for New Zealand Appln. No. 739211, dated Jun. 14, 2018, 3 pages.
Office Action for Russian Appln. No. 2018106877, dated Oct. 18, 2018, 16 pages (with English translation).
Office Action for Russian Appln. No. 2018106904, dated Sep. 20, 2018, 14 pages (with English translation).
Office Action for Russian Appln. No. 2018106914, dated Nov. 15, 2018, 14 pages (with English translation).
Office Action for Taiwanese Appln. No. 105132939, dated Nov. 2, 2017, 8 pages (with English translation).
Othman et al., "1,3,4-Oxadiazole, 1,3,4-thiadiazole and 1,2,4-triazole derivatives as potential antibacterial agents," Arab. J. Chem., 2014:1-16.
Pal et al., "Hydroxamic acid—A novel molecule for anticancer therapy," J. Adv. Pharm. Technol. Res., 2012, 3(2):92-99.
Rajak et al., "2,5-Disubstituted-1,3,4-oxadiazoles/thiadiazole as surface recognition moiety: Design and synthesis of novel hydroxamic acid based histone deacetylase inhibitors," Bioorg. Med. Chem. Lett., Aug. 2011, 21:5735-5738.
Rossi et al., "4-N-Hydroxy-4-[ 1-( sulfonyl )piperidin-4-yl ]-butyramides as HDAC inhibitors," Bioorg. Med. Chem. Lett., Sep. 2011, 21:6767-6769.
International Search Report for PCT/KR2019/009228, dated Nov. 11, 2019. 4 pages.
Hassig et al., Nuclear histone acetylases and deacetylases and transcriptional regulation: HATs off to HDACs' Current Opinion in Chemical Biology 1997, 1, pp. 300-308.
Warrell et al, Therapeutic Targeting of Transcription in Acute Promyelocytic Leukemia by Use of an Inhibitor of Histone Deacetylase, Journal of the National Cancer Institute, vol. 90, No. 21, Nov. 4, 1998, pp. 1621-1625.
Bolden et al., "Anticancer activities of histone deacetylase inhibitors", National Reviews, Drug Discovery, vol. 5, Sep. 2006, pp. 769-784.
Piekarz et al., "Clinical Toxicities of Histone Deacetylase Inhibitors", Pharmaceuticals 2010, 3, pp. 2751-2767.
Witt et al., "HDAC family: What are the cancer relevant targets"?, Cancer Letters 277, 2009, 2, pp. 8-21.
Matthias et al., "Mice Lacking Histone Deacetylase 6 Have Hyperacetylated Tubulin but Are Viable and Develop Normally", Molecular and Cellular Biology, Mar. 2008, pp. 1688-1701.
Yao et al., "HDAC6 Regulates Hsp90 Acetylation and Chaperone-Dependent Activation of Glucocorticoid Receptor", Molecular Cell, vol. 18, May 27, 2006, pp. 601-607.
Santo et al., "Preclinical activity, pharmacodynamic, and pharmacokinetic properties of a selective HDAC6 inhibitor, ACY-1215, in combination with bortezomib in multiple myeloma", Blood, Mar. 15, 2012, vol. 119, No. 11, pp. 2579-2590.
Vishwakarma et al., "Tubastatin, a selective histone deacetylase 6 inhibitor shows anti-inflammatory and anti-rheumatic effects", International Immunopharmacology 2013, 16, pp. 72-78.
Hlu et al., "HDAC6 α-tubulin deacetylase: A potential therapeutic target in neurodegenerative diseases", Journal of the Neurological Sciences 304, 2011, pp. 1-8.
Wiest et al., "Computational Exploration of Zinc Binding Groups for HDAC Inhibition", J. Org. Chem. , May 17, 2013 78: pp. 5051-5055.
Methot et al., Exploration of the internal cavity of histone deacetylase (HDAC) with selective HDAC1/HDAC2 inhibitors (SHI-1:2), Bioorganic & Medicinal Chemistry Letters 18 (2008), pp. 973-978.
Woster et al., "Discovery of a new class of histone deacetylase inhibitors with a novel zinc binding group", Med. Chem. Commun. 2015, online publication, 6 pages.
Baijuka, et al., "Synthesis and Biological Activities of 1, 3, 4-Oxadiazole Derivatives: a Review of Literature", Int. J. Adv. Res, [Published] Jan. 2018, vol. 6, No. 1, pp. 1114-1122.
Extended European Search Report in European Appln. No. 20814548.2, dated Nov. 8, 2022, 5 pages.
Extended European Search Report in European Appln. No. 20815468.2, dated May 4, 2023, 13 pages.
Notice of Allowance in Australian Appln. No. 2020284167, dated May 1, 2023, 3 pages.
Notice of Allowance in Korean Appln. No. 2020-0065507, dated Nov. 10, 2022, 10 pages (with English translation).

(56) References Cited

OTHER PUBLICATIONS

Office Action for Australian Appln. No. 2020284167, dated Nov. 3, 2022, 3 pages.
Office Action for Australian Appln. No. 2020284606, dated Aug. 11, 2022, 8 pages.
Office Action for Canadian Appln. No. 3136223, dated Nov. 30, 2022, 4 pages.
Office Action for Canadian Appln. No. 3139026, dated Dec. 14, 2022, 6 pages.
Office Action for Indian Appln. No. 202137058528, dated Jul. 6, 2022, 5 pages.
Office Action for Indian Appln. No. 202137061193, dated Jul. 7, 2022, 6 pages.
Office Action for Japanese Appln. No. 2021-571486, dated Jan. 10, 2023, 12 pages (with English Translation).
Office Action for Japanese Appln. No. 2021-571498, dated Nov. 8, 2022, 12 pages (with English Translation).
Office Action for Malaysian Appln. No. PI2021006507, dated May 22, 2023, 4 pages.
Office Action for Russian Appln. No. 2021139516, dated Aug. 11, 2022, 20 pages (with English Translation).
Office Action for Russian Appln. No. 2021139540, dated Aug. 17, 2022, 32 pages (with English Translation).
U.S. Appl. No. 17/615,363, filed Nov. 30, 2021, Chang Sik Lee.
U.S. Appl. No. 17/614,967, filed Nov. 29, 2021, Chang Sik Lee.
ACS RN 904653-05-0, "Benzamide, 3-methoxy-N-[4-[5-(trichloromethyl)-1,3,4-oxadiazol-2-yl]phenyl]", STN-Registry, dated Aug. 25, 2006, 1 page.
ACS RN 904568-68-9, "Benz amide, 3,4,5-trimethoxy-N-[4-[5-(trifluoromethyl)-1,3,4-oxadiazol-2-yl]phenyl]" STN-Registry, Aug. 25, 2006, 1 page.
Office Action and Search Report for Chinese Application No. 201680044430.0, dated Aug. 21, 2020, 9 pages (with English translation).
Office Action and Search Report for Chinese Application No. 201680053218.0 dated Nov. 4, 2020, 14 pages (with English translation).
Office Action and Search Report for Chinese Application No. 201680058155.8, dated Jan. 6, 2021, 13 pages (with English translation).
Office Action and Search Report for Chinese Application No. 201680072029.8, dated Oct. 26, 2020, 12 pages (with English translation).
PCT International Preliminary Report on Patentability in International Appln. No. PCT/KR2019/009228, dated Feb. 4, 2021, 6 pages.
Notice of Allowance in Korean Appln. No. 2018-0087455, dated Oct. 7, 2021, 4 pages (with English translation).
Office Action in Russian Appln. No. 2021104625, dated Jul. 23, 2021, 22 pages (with English translation).
Action for TW108126316 dated Oct. 22, 2020 and English translation. 7 pages.
Baijika, et al., "Synthesis and biological activities of 1, 3, 4-oxadiazole derivatives: A Review of Literature", Int. J. Adv. Res, [Published] Jan. 2018, vol. 6, No. 1, pp. 1114-1122.
Office Action for TW109118219, dated Mar. 19, 2021 and English translation, 9 pages.
Office Action for TW109118221, dated Apr. 15, 2021 and English translation, 9 pages.
PCT International Search Report and Written Opinion in International Application No. PCT/IB2020/055109, dated Sep. 4, 2020, 10 pages.
PCT International Search Report and Written Opinion in International Application No. PCT/IB2020/055110, dated Sep. 4, 2020, 12 pages.
PCT International Search Report and Written Opinion in International Application No. PCT/KR2019/009228, dated Nov. 11, 2019, 8 pages.
Office Action in Chinese Appln. No. 201980049375.8, dated Sep. 20, 2023, 13 pages (with English translation).
Office Action in Malaysia Appln. No. PI2021000199, dated Dec. 1, 2023, 2 pages (with English translation).
Office Action in Mexico Appln. No. MX/a/2021/000737, dated Jun. 15, 2023, 8 pages (with English translation).
Office Action in New Zealand Appln. No. 771899, dated Aug. 22, 2023, 4 pages.
Office Action in Vietnam Appln. No. 51472w/SHTT-SC, dated Aug. 23, 2023, 4 pages (with English translation).
Silverman, "The Organic Chemistry of Drug Design and Drug Action," Second Edition, 2008, pp. 17-23.

\* cited by examiner

1,3,4-OXADIAZOLE DERIVATIVE COMPOUNDS AS HISTONE DEACETYLASE 6 INHIBITOR, AND PHARMACEUTICAL COMPOSITION COMPRISING THE SAME

TECHNICAL FIELD

The present invention relates to 1,3,4-oxadiazole derivative compounds having a histone deacetylase 6 (HDAC6) inhibitory activity, optical isomers thereof, pharmaceutically acceptable salts thereof, a pharmaceutical use thereof, and a method for preparing the same.

BACKGROUND ART

In cells, a post-translational modification such as acetylation serves as a very important regulatory module at the hub of biological processes, and is also strictly controlled by a number of enzymes. As a core protein constituting chromatin, histone functions as an axis, around which DNA winds, and thus helps a DNA condensation. Also, a balance between acetylation and deacetylation of histone plays a very important role in gene expression.

As an enzyme for removing an acetyl group from lysine residue of histone protein, which constitutes chromatin, histone deacetylases (HDACs) are known to be associated with gene silencing and induce a cell cycle arrest, angiogenic inhibition, immunoregulation, apoptosis, etc. (Hassig et al., Curr. Opin. Chem. Biol. 1997, 1, 300-308). Also, it is reported that the inhibition of HDAC enzyme functions induces cancer cells into committing apoptosis for themselves by lowering an activity of cancer cell survival-related factors and activating cancer cell death-related factors in vivo (Warrell et al., J. Natl. Cancer Inst. 1998, 90, 1621-1625).

For humans, 18 HDACs are known and classified into four classes according to their homology with yeast HDAC. At that time, eleven HDACs using zinc as a cofactor may be divided into three classes: Class I (HDAC1, 2, 3, 8), Class II (IIa: HDAC4, 5, 7, 9; IIb: HDAC6, 10) and Class IV (HDAC11). Further, seven HDACs of Class III (SIRT 1-7) use NAD+ as a cofactor instead of zinc (Bolden et al., Nat. Rev. Drug Discov. 2006, 5(9), 769-784).

Various HDAC inhibitors are now in a preclinical or clinical development stage, but only non-selective HDAC inhibitors have been known as an anti-cancer agent. Vorinostat (SAHA) and romidepsin (FK228) have obtained an approval as a therapeutic agent for cutaneous T-cell lymphoma, while panobinostat (LBH-589) has won an approval as a therapeutic agent for multiple myeloma. However, it is known that the non-selective HDAC inhibitors generally bring about side effects such as fatigue, nausea and the like at high doses (Piekarz et al., Pharmaceuticals 2010, 3, 2751-2767). It is reported that such side effects are caused by the inhibition of class I HDACs. Due to such side effects, etc., the non-selective HDAC inhibitors have been subject to restriction on drug development in other fields than anti-cancer agents (Witt et al., Cancer Letters 277 (2009) 8.21).

Meanwhile, it is reported that the selective inhibition of Class II HDACs would not show toxicity, which has occurred in the inhibition of Class I HDACs. In case of developing the selective HDAC inhibitors, it would be likely to solve side effects such as toxicity, etc., caused by the non-selective inhibition of HDACs. Accordingly, there is a chance that the selective HDAC inhibitors may be developed as an effective therapeutic agent for various diseases (Matthias et al., Mol. Cell. Biol. 2008, 28, 1688-1701).

HDAC6, one of Class IIb HDACs, is known to be mainly present in cytoplasma and contain a tubulin protein, thus being involved in the deacetylation of a number of nonhistone substrates (HSP90, cortactin, etc.) (Yao et al., Mol. Cell 2005, 18, 601-607). HDAC6 has two catalytic domains, in which a zinc finger domain of C-terminal may bind to an ubiquitinated protein. HDAC6 is known to have a number of non-histone proteins as a substrate, and thus play an important role in various diseases such as cancer, inflammatory diseases, autoimmune diseases, neurological diseases, neurodegenerative disorders and the like (Santo et al., Blood 2012 119: 2579-258; Vishwakarma et al., International Immunopharmacology 2013, 16, 72-78; Hu et al., J. Neurol. Sci. 2011, 304, 1-8).

A structural feature that various HDAC inhibitors have in common consists of a cap group, a linker and a zinc binding group (ZBG) as shown in a following structure of vorinostat. Many researchers have conducted a study on the inhibitory activity and selectivity with regard to enzymes through a structural modification of the cap group and the linker. Out of those groups, it is known that the zinc binding group plays a more important role in the enzyme inhibitory activity and selectivity (Wiest et al., J. Org. Chem. 2013 78: 5051-5065; Methot et al., Bioorg. Med. Chem. Lett. 2008, 18, 973-978).

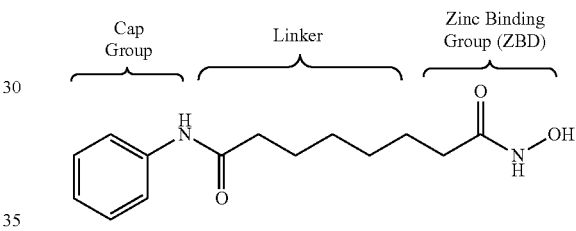

Most of said zinc binding group consists of hydroxamic acid or benzamide, out of which hydroxamic acid derivatives show a strong HDAC inhibitory effect, but have a problem with low bioavailability and serious off-target activity. Benzamide contains aniline, and thus has a problem in that it may produce toxic metabolites in vivo (Woster et al., Med. Chem. Commun. 2015, online publication).

Accordingly, unlike the non-selective inhibitors having side effects, there is a need to develop a selective HDAC6 inhibitor, which has a zinc binding group with improved bioavailability, while causing no side effects in order to treat cancer, inflammatory diseases, autoimmune diseases, neurological diseases, neurodegenerative disorders and the like.

DISCLOSURE OF INVENTION

Technical Problem

An objective of the present invention is to provide 1,3,4-oxadiazole derivative compounds having a selective HDAC6 inhibitory activity, optical isomers thereof or pharmaceutically acceptable salts thereof.

Other objective of the present invention is to provide a method for preparing 1,3,4-oxadiazole derivative compounds, optical isomers thereof or pharmaceutically acceptable salts thereof.

Another objective of the present invention is to provide a pharmaceutical composition containing 1,3,4-oxadiazole derivative compounds having a selective HDAC6 inhibitory activity, optical isomers thereof or pharmaceutically acceptable salts thereof.

Yet another objective of the present invention is to provide a pharmaceutical composition for preventing or treating HDAC6 activity-related diseases, containing 1,3,4-oxadiazole derivative compounds, optical isomers thereof or pharmaceutically acceptable salts thereof as an effective component.

Still yet another objective of the present invention is to provide a use of 1,3,4-oxadiazole derivative compounds, optical isomers thereof or pharmaceutically acceptable salts thereof in preparing a drug for preventing or treating HDAC6 activity-related diseases.

Further still yet another objective of the present invention is to provide a method for treating HDAC6 activity-related diseases, including a step of administering a therapeutically effective amount of 1,3,4-oxadiazole derivative compounds, optical isomers thereof or pharmaceutically acceptable salts thereof.

Solution to Problem

The present inventors have found novel 1,3,4-oxadiazole derivative compounds having a histone deacetylase 6 (HDAC6) inhibitory activity and have used the same in preventing or treating HDAC6 activity-related diseases, thereby completing the present invention.

1,3,4-Oxadiazole Derivative Compounds

According to said objectives, the present invention provides 1,3,4-oxadiazole derivative compounds represented by a following formula I, optical isomers thereof or pharmaceutically acceptable salts thereof:

[Formula I]

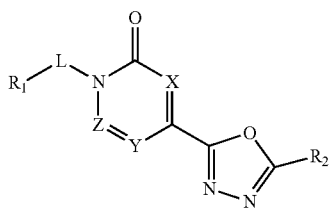

wherein,

X, Y and Z are each independently $CR_3$ or N;

L is —($C_1$-$C_6$ alkylene)-, —($C_2$-$C_6$ alkenylene)-, —(C=O)—($C_1$-$C_4$ alkylene)-, —(C=O)O—($C_1$-$C_4$ alkylene)-, —(C=O)NH—($C_1$-$C_4$ alkylene)-, —O(C=O)—($C_1$-$C_4$ alkylene)- or a single bond, wherein at least one H of —($C_1$-$C_6$ alkylene)-, —($C_2$-$C_6$ alkenylene)-, —(C=O)—($C_1$-$C_4$ alkylene)-, —(C=O)O—($C_1$-$C_4$ alkylene)-, —(C=O)NH—($C_1$-$C_4$ alkylene)- and —O(C=O)—($C_1$-$C_4$ alkylene)- may be substituted with aryl or heteroaryl;

$R_1$ is hydrogen, —$C_1$-$C_6$ alkyl, —$C_2$-$C_6$ alkenyl, —$C_3$-$C_8$ cycloalkyl, heterocycloalkyl, benzyl, aryl, heteroaryl or —$NR_4R_5$, wherein at least one H of aryl or heteroaryl may be substituted with —$C_1$-$C_6$ alkyl, —$C_2$-$C_6$ alkenyl, —$C_1$-$C_6$ haloalkyl, —$C_1$-$C_6$ aminoalkyl, —$C_1$-$C_6$ hydroxyalkyl, —$C_1$-$C_6$ alkoxy, hydroxy, cyano, halo, nitro, —$CF_2H$, —$CF_3$, —$NR_6R_7$, —C(=O)—$R_8$ or —S(=O)$_2$—$R_9$;

$R_2$ is —$CF_2H$ or —$CF_3$;

$R_3$ is hydrogen, halo or —$C_1$-$C_6$ alkyl;

$R_4$ to $R_7$ are each independently H or —$C_1$-$C_6$ alkyl; and $R_8$ and $R_9$ are each independently H, OH or —$C_1$-$C_6$ alkyl.

According to one embodiment aspect of the present invention, there are provided the compounds represented by the formula I above, wherein:

X, Y and Z are each independently $CR_3$ or N;

L is —($C_1$-$C_6$ alkylene)-, —($C_2$-$C_6$ alkenylene)-, —(C=O)—($C_1$-$C_4$ alkylene)-, —(C=O)O—($C_1$-$C_4$ alkylene)-, —(C=O)NH—($C_1$-$C_4$ alkylene)-, —O(C=O)—($C_1$-$C_4$ alkylene)- or a single bond, wherein at least one H of —($C_1$-$C_6$ alkylene)-, —($C_2$-$C_6$ alkenylene)-, —(C=O)—($C_1$-$C_4$ alkylene)-, —(C=O)O—($C_1$-$C_4$ alkylene)-, —(C=O)NH—($C_1$-$C_4$ alkylene)- and —O(C=O)—($C_1$-$C_4$ alkylene)- may be substituted with aryl;

$R_1$ is hydrogen, —$C_1$-$C_6$ alkyl, —$C_2$-$C_6$ alkenyl, heterocycloalkyl, benzyl, aryl, heteroaryl or —$NR_4R_5$, wherein at least one H of aryl or heteroaryl may be substituted with —$C_1$-$C_6$ alkyl, —$C_1$-$C_6$ alkoxy, halo, nitro, —$CF_3$ or —S(=O)$_2$—$R_9$;

$R_2$ is —$CF_2H$ or —$CF_3$;

$R_3$ is hydrogen or halo;

$R_4$ to $R_5$ are each independently —$C_1$-$C_6$ alkyl; and $R_9$ is each independently —$C_1$-$C_6$ alkyl.

Also, according to a specific embodiment aspect of the present invention, there are provided the compounds represented by the formula I above, wherein:

X, Y and Z are each independently $CR_3$;

L is —($C_1$-$C_4$ alkylene)-, —($C_2$-$C_4$ alkenylene)-, —(C=O)—($C_1$-$C_2$ alkylene)-, —(C=O)O—($C_1$-$C_2$ alkylene)-, —(C=O)NH—($C_1$-$C_2$ alkylene)-, —O(C=O)—($C_1$-$C_2$ alkylene)- or a single bond, wherein at least one H of —($C_1$-$C_4$ alkylene)-, —($C_2$-$C_4$ alkenylene)-, —(C=O)—($C_1$-$C_2$ alkylene)-, —(C=O)O—($C_1$-$C_2$ alkylene)-, —(C=O)NH—($C_1$-$C_2$ alkylene)- and —O(C=O)—($C_1$-$C_2$ alkylene)- may be substituted with aryl;

$R_1$ is —$C_1$-$C_6$ alkyl, —$C_2$-$C_6$ alkenyl

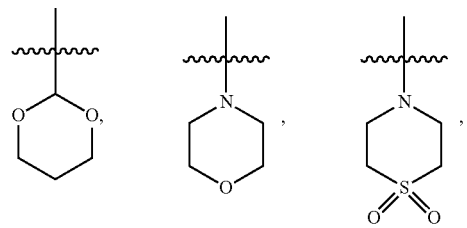 [SMILES: *C1OCCCO1 ; *N1CCOCC1 ; *N1CCS(=O)(=O)CC1]

benzyl, phenyl, naphthyl,

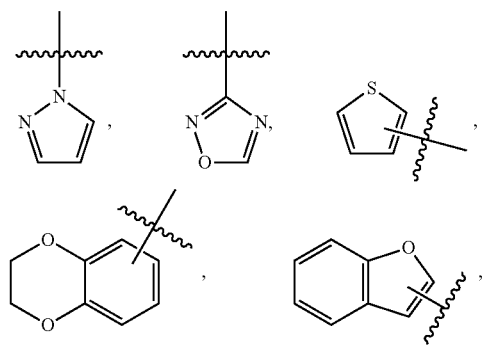

-continued

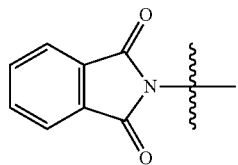

or —NR₄R₅, wherein at least one H of phenyl, naphthyl,

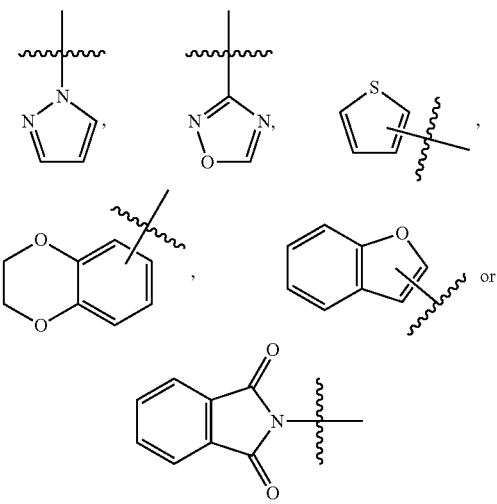

may be substituted with —C₁-C₆ alkyl, —C₁-C₆ alkoxy, halo, nitro, —CF₃ or —S(=O)₂—R₉;

$R_2$ is —CF₂H or —CF₃;

$R_3$ is hydrogen;

$R_4$ to $R_5$ are each independently —C₁-C₄ alkyl; and $R_9$ is each independently —C₁-C₄ alkyl.

According to a more specific embodiment aspect of the present invention, there are provided the compounds represented by the formula I above, wherein:

X, Y and Z are each independently CR₃;

L is —(C₁-C₄ alkylene)-, —(C₂-C₄ alkenylene)-, —(C=O)—(C₁-C₂ alkylene)-, —(C=O)NH—(C₁-C₂ alkylene)-, —O(C=O)—(C₁-C₂ alkylene)- or a single bond, wherein at least one H of —(C₁-C₄ alkylene)-, —(C₂-C₄ alkenylene)-, —(C=O)—(C₁-C₂ alkylene)-, —(C=O)NH—(C₁-C₂ alkylene)- and —O(C=O)—(C₁-C₂ alkylene)- may be substituted with aryl;

$R_1$ is —C₁-C₆ alkyl, —C₂-C₆ alkenyl,

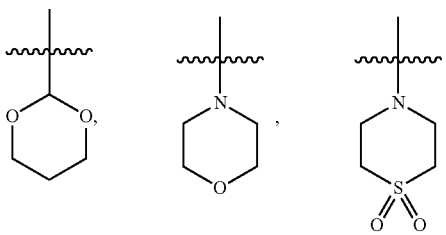

phenyl, naphthyl,

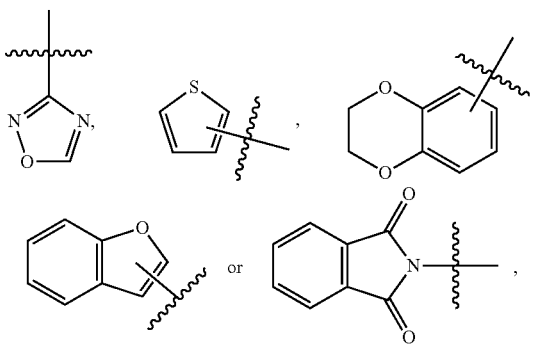

wherein at least one H of phenyl, naphthyl,

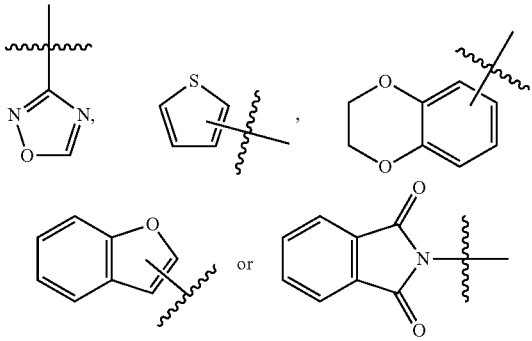

may be substituted with —C₁-C₆ alkoxy, halo, nitro or —CF₃;

$R_2$ is —CF₂H; and $R_3$ is hydrogen.

According to a more specific embodiment aspect of the present invention, a structural formula of the compounds represented by the formula I of the present invention is the same as represented by a following Table 1.

TABLE 1

| Compound | structure |
| --- | --- |
| 1 | ![structure] |

TABLE 1-continued

| Compound | structure |
|---|---|
| 2 | 1-benzyl-4-[5-(difluoromethyl)-1,3,4-oxadiazol-2-yl]pyridin-2(1H)-one |
| 3 | 1-(2-oxo-2-phenylethyl)-4-[5-(difluoromethyl)-1,3,4-oxadiazol-2-yl]pyridin-2(1H)-one |
| 4 | 1-methyl-4-[5-(difluoromethyl)-1,3,4-oxadiazol-2-yl]pyridin-2(1H)-one |
| 5 | 1-cinnamyl-4-[5-(difluoromethyl)-1,3,4-oxadiazol-2-yl]pyridin-2(1H)-one |
| 6 | 1-[2-(1H-pyrazol-1-yl)ethyl]-4-[5-(difluoromethyl)-1,3,4-oxadiazol-2-yl]pyridin-2(1H)-one |
| 7 | 1-[2-(naphthalen-2-yl)-2-oxoethyl]-4-[5-(difluoromethyl)-1,3,4-oxadiazol-2-yl]pyridin-2(1H)-one |
| 8 | 1-[2-(3,5-dimethoxyphenyl)ethyl]-4-[5-(difluoromethyl)-1,3,4-oxadiazol-2-yl]pyridin-2(1H)-one |

TABLE 1-continued

| Compound | structure |
|---|---|
| 9 | 1-(2-(1,3-dioxan-2-yl)ethyl)-4-(5-(difluoromethyl)-1,3,4-oxadiazol-2-yl)pyridin-2(1H)-one |
| 10 | 4-(5-(difluoromethyl)-1,3,4-oxadiazol-2-yl)-1-(2,5-difluorobenzyl)pyridin-2(1H)-one |
| 11 | 4-(5-(difluoromethyl)-1,3,4-oxadiazol-2-yl)-1-(2-(diethylamino)ethyl)pyridin-2(1H)-one |
| 12 | 1-(2-chlorobenzyl)-4-(5-(difluoromethyl)-1,3,4-oxadiazol-2-yl)pyridin-2(1H)-one |
| 13 | 4-(5-(difluoromethyl)-1,3,4-oxadiazol-2-yl)-1-(2,4,5-trifluorobenzyl)pyridin-2(1H)-one |
| 14 | 4-(5-(difluoromethyl)-1,3,4-oxadiazol-2-yl)-1-(3-fluorobenzyl)pyridin-2(1H)-one |
| 15 | benzyl 2-(4-(5-(difluoromethyl)-1,3,4-oxadiazol-2-yl)-2-oxopyridin-1(2H)-yl)acetate |

TABLE 1-continued

| Compound | structure |
|---|---|
| 16 | 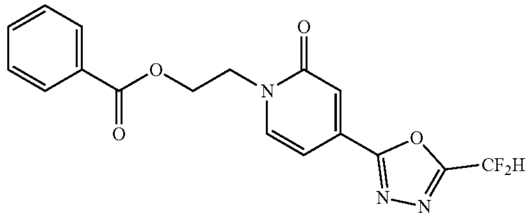 [SMILES: O=C(OCCn1ccc(-c2nnc(C(F)F)o2)cc1=O)c1ccccc1] |
| 17 | 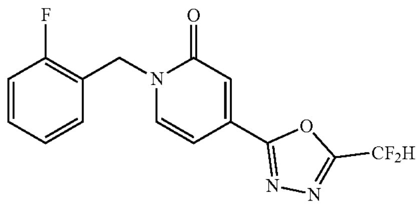 [SMILES: O=c1cc(-c2nnc(C(F)F)o2)ccn1Cc1ccccc1F] |
| 18 | 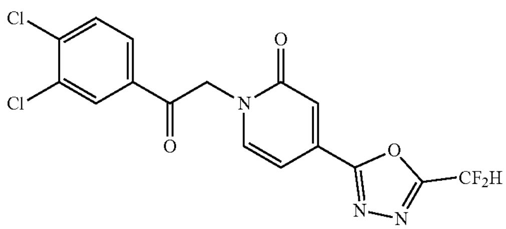 [SMILES: O=C(Cn1ccc(-c2nnc(C(F)F)o2)cc1=O)c1ccc(Cl)c(Cl)c1] |
| 19 | 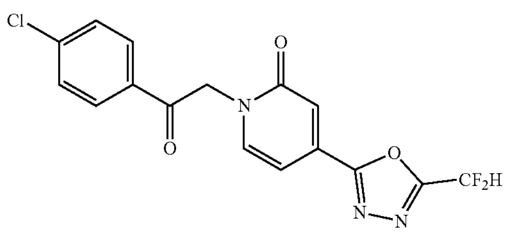 [SMILES: O=C(Cn1ccc(-c2nnc(C(F)F)o2)cc1=O)c1ccc(Cl)cc1] |
| 20 | 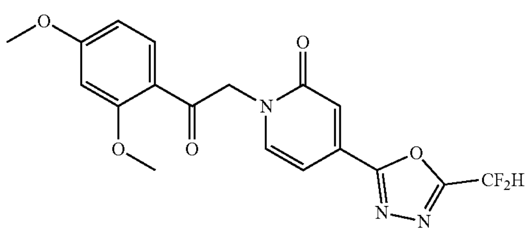 [SMILES: COc1ccc(C(=O)Cn2ccc(-c3nnc(C(F)F)o3)cc2=O)c(OC)c1] |
| 21 | 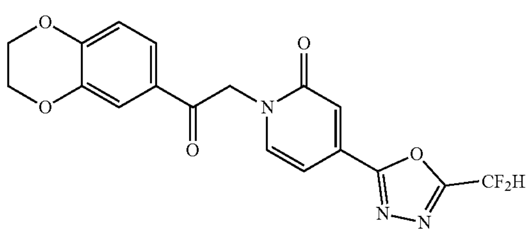 [SMILES: O=C(Cn1ccc(-c2nnc(C(F)F)o2)cc1=O)c1ccc2c(c1)OCCO2] |
| 22 | 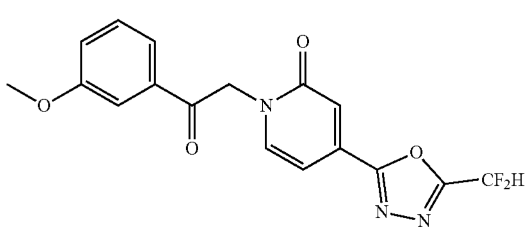 [SMILES: COc1cccc(C(=O)Cn2ccc(-c3nnc(C(F)F)o3)cc2=O)c1] |

TABLE 1-continued

| Compound | structure |
|---|---|
| 23 | 4-chloro-2-fluoro-5-methylphenyl substituted: 1-(2-(4-chloro-2-fluoro-5-methylphenyl)-2-oxoethyl)-4-(5-(difluoromethyl)-1,3,4-oxadiazol-2-yl)pyridin-2(1H)-one |
| 24 | 2,5-dimethoxyphenyl substituted: 4-(5-(difluoromethyl)-1,3,4-oxadiazol-2-yl)-1-(2-(2,5-dimethoxyphenyl)-2-oxoethyl)pyridin-2(1H)-one |
| 25 | 4-nitrophenyl substituted: 4-(5-(difluoromethyl)-1,3,4-oxadiazol-2-yl)-1-(2-(4-nitrophenyl)-2-oxoethyl)pyridin-2(1H)-one |
| 26 | 4-nitrobenzyl substituted: 4-(5-(difluoromethyl)-1,3,4-oxadiazol-2-yl)-1-(4-nitrobenzyl)pyridin-2(1H)-one |
| 27 | 2-ethylbutyl substituted: 4-(5-(difluoromethyl)-1,3,4-oxadiazol-2-yl)-1-(2-ethylbutyl)pyridin-2(1H)-one |
| 28 | 1-((5-(trifluoromethyl)-1,2,4-oxadiazol-3-yl)methyl)-4-(5-(difluoromethyl)-1,3,4-oxadiazol-2-yl)pyridin-2(1H)-one |

TABLE 1-continued
| Compound | structure |
|---|---|
| 29 | 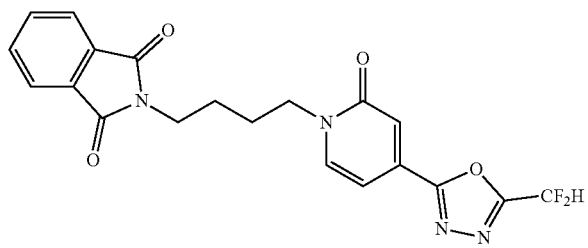 [SMILES: O=C1c2ccccc2C(=O)N1CCCCn1ccc(-c2nnc(C(F)F)o2)cc1=O] |
| 30 | 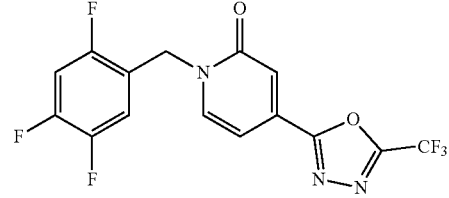 [SMILES: O=c1cc(-c2nnc(C(F)(F)F)o2)ccn1Cc1cc(F)c(F)cc1F] |
| 31 | 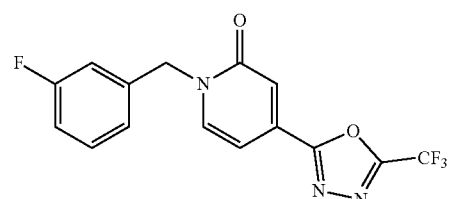 |
| 32 | 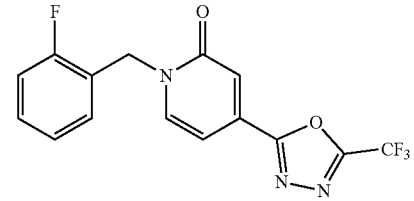 [SMILES: O=c1cc(-c2nnc(C(F)(F)F)o2)ccn1Cc1ccccc1F] |
| 33 | 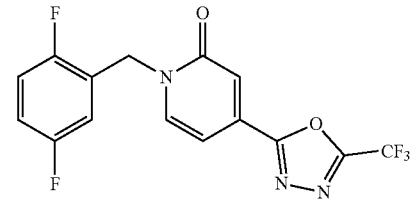 [SMILES: O=c1cc(-c2nnc(C(F)(F)F)o2)ccn1Cc1cc(F)ccc1F] |
| 34 | 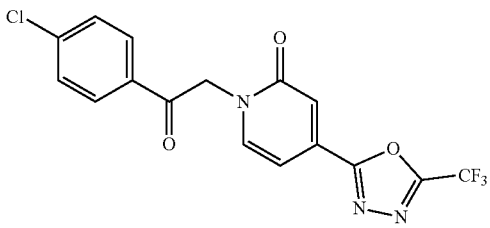 [SMILES: O=C(Cn1ccc(-c2nnc(C(F)(F)F)o2)cc1=O)c1ccc(Cl)cc1] |
| 35 | 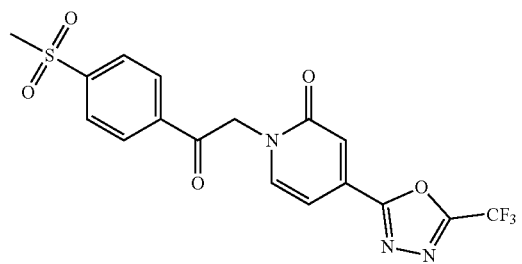 [SMILES: CS(=O)(=O)c1ccc(C(=O)Cn2ccc(-c3nnc(C(F)(F)F)o3)cc2=O)cc1] |

TABLE 1-continued
| Compound | structure |
|---|---|
| 36 | 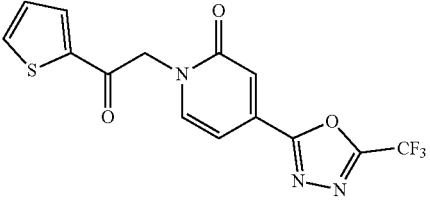 [SMILES: O=C(Cn1ccc(-c2nnc(C(F)(F)F)o2)cc1=O)c1cccs1] |
| 37 | 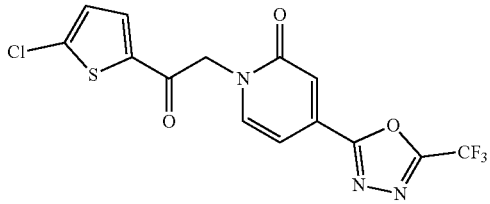 [SMILES: O=C(Cn1ccc(-c2nnc(C(F)(F)F)o2)cc1=O)c1ccc(Cl)s1] |
| 38 | 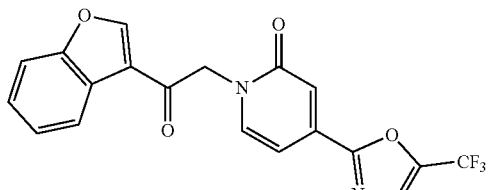 |
| 39 | 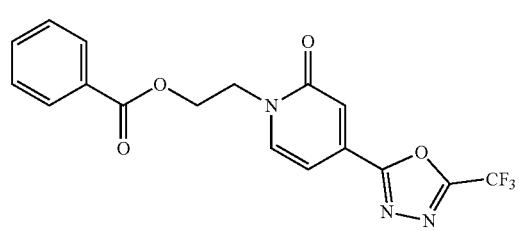 [SMILES: O=C(OCCn1ccc(-c2nnc(C(F)(F)F)o2)cc1=O)c1ccccc1] |
| 40 | 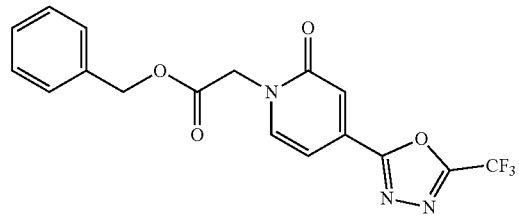 [SMILES: O=C(Cn1ccc(-c2nnc(C(F)(F)F)o2)cc1=O)OCc1ccccc1] |
| 41 | 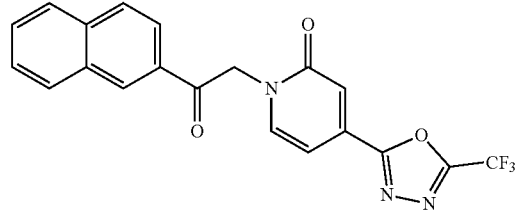 [SMILES: O=C(Cn1ccc(-c2nnc(C(F)(F)F)o2)cc1=O)c1ccc2ccccc2c1] |
| 42 | 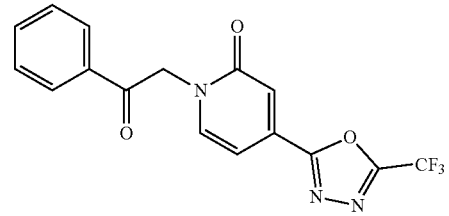 [SMILES: O=C(Cn1ccc(-c2nnc(C(F)(F)F)o2)cc1=O)c1ccccc1] |

TABLE 1-continued

| Compound | structure |
|---|---|
| 43 | 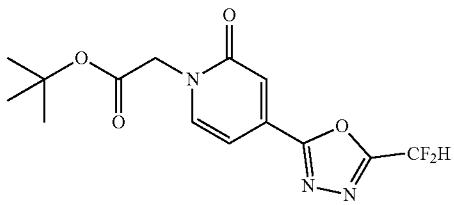 [SMILES: CC(C)(C)OC(=O)Cn1ccc(-c2nnc(C(F)F)o2)cc1=O] |
| 44 | 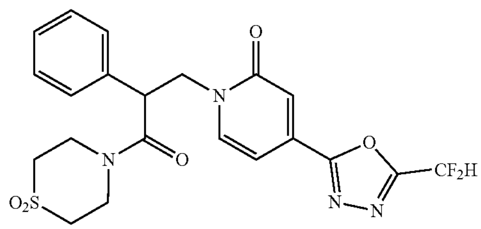 [SMILES: O=C(C(Cn1ccc(-c2nnc(C(F)F)o2)cc1=O)c1ccccc1)N1CCS(=O)(=O)CC1] |
| 45 | 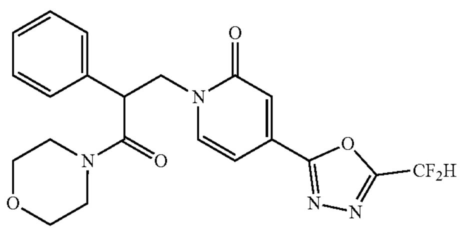 [SMILES: O=C(C(Cn1ccc(-c2nnc(C(F)F)o2)cc1=O)c1ccccc1)N1CCOCC1] |
| 46 | 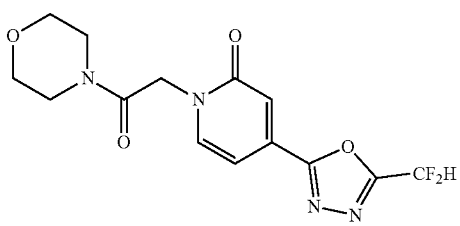 [SMILES: O=C(Cn1ccc(-c2nnc(C(F)F)o2)cc1=O)N1CCOCC1] |
| 47 | 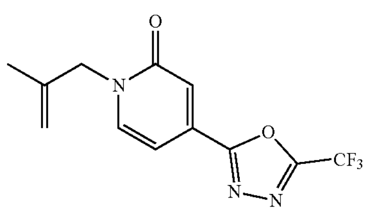 [SMILES: C=C(C)Cn1ccc(-c2nnc(C(F)(F)F)o2)cc1=O] |
| 48 | 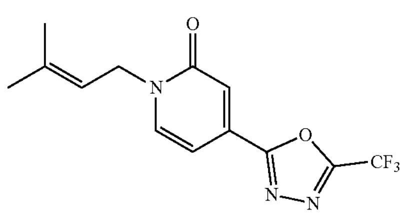 [SMILES: CC(C)=CCn1ccc(-c2nnc(C(F)(F)F)o2)cc1=O] |
| 49 | 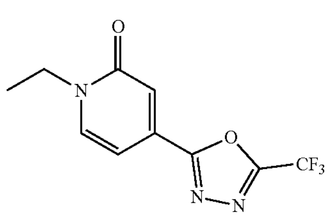 [SMILES: CCn1ccc(-c2nnc(C(F)(F)F)o2)cc1=O] |

TABLE 1-continued

| Compound | structure |
|---|---|
| 50 | 1-(2-(thiophen-2-yl)-2-oxoethyl)-4-(5-(difluoromethyl)-1,3,4-oxadiazol-2-yl)pyridin-2(1H)-one |
| 51 | 1-(2-(benzofuran-3-yl)-2-oxoethyl)-4-(5-(difluoromethyl)-1,3,4-oxadiazol-2-yl)pyridin-2(1H)-one |
| 52 | 1-(2-methylallyl)-4-(5-(difluoromethyl)-1,3,4-oxadiazol-2-yl)pyridin-2(1H)-one |
| 53 | 1-(3-methylbutyl)-4-(5-(difluoromethyl)-1,3,4-oxadiazol-2-yl)pyridin-2(1H)-one |
| 54 | 1-(3-methylbut-2-en-1-yl)-4-(5-(difluoromethyl)-1,3,4-oxadiazol-2-yl)pyridin-2(1H)-one |
| 55 | 1-ethyl-4-(5-(difluoromethyl)-1,3,4-oxadiazol-2-yl)pyridin-2(1H)-one |
| 56 | 1-(2-(5-chlorothiophen-2-yl)-2-oxoethyl)-4-(5-(difluoromethyl)-1,3,4-oxadiazol-2-yl)pyridin-2(1H)-one |

TABLE 1-continued

| Compound | structure |
|---|---|
| 57 | 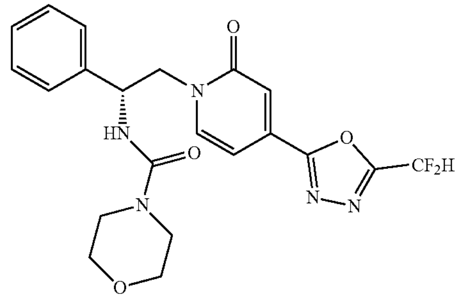 [SMILES: O=C(N[C@@H](Cn1ccc(-c2nnc(C(F)F)o2)cc1=O)c1ccccc1)N1CCOCC1] |
| 58 | 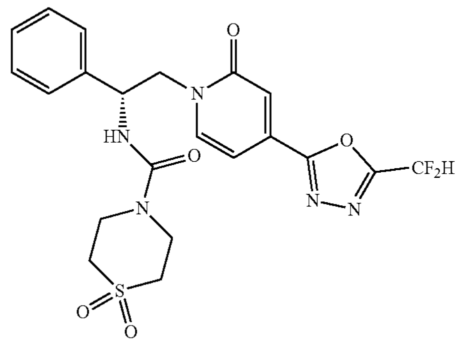 [SMILES: O=C(N[C@@H](Cn1ccc(-c2nnc(C(F)F)o2)cc1=O)c1ccccc1)N1CCS(=O)(=O)CC1] |

In the present invention, the compounds represented by the formula I above, optical isomers thereof or pharmaceutically acceptable salts thereof are preferably selected from the group consisting of compounds 1, 2, 3, 5, 7, 8, 9, 10, 13, 14, 15, 20, 21, 24, 25, 26, 28, 29, 43, 44, 45, 50, 51, 52, 53, 55, 56, 57 and 58, and more preferably selected from the group consisting of compounds 1, 2, 5, 14, 15, 28 and 56.

The compounds represented by the formula I of the present invention may include at least one asymmetric carbon, and thus may be present as racemate, racemic mixture, single enantiomer, mixture of diastereomers and respective diastereomers thereof. As such isomers, the compounds represented by the formula I may be separated by splitting themselves according to the related art, for example, with the aid of a column chromatography, HPLC or the like. Likewise, respective stereoisomers of the compounds represented by the formula I may be stereospecifically synthesized with a known array of optically pure starting materials and/or reagents.

In the present invention, pharmaceutically acceptable salts mean the salts conventionally used in a pharmaceutical industry, for example, inorganic ion salts prepared from calcium, potassium, sodium, magnesium and the like; inorganic acid salts prepared from hydrochloric acid, nitric acid, phosphoric acid, bromic acid, iodic acid, perchloric acid, tartaric acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbric acid, carbonic acid, vanillic acid, hydroiodic acid, etc.; sulphonic acid salts prepared from methanesulfonic acid, ethanesulfonic acid, benzenesulfonic acid, p-toluenesulfonic acid, naphthalenesulfonic acid and the like; amino acid salts prepared from glycine, arginine, lysine, etc.; amine salts prepared from trimethylamine, triethylamine, ammonia, pyridine, picoline, etc.; and the like, but types of salts meant in the present invention are not limited to those listed salts. In the present invention, preferable salts include hydrochloric acid, trifluoroacetic acid, citric acid, bromic acid, maleic acid, phosphoric acid, sulfuric acid and tartaric acid.

Here, a "substituted" group is one in which at least one hydrogen atom is substituted with at least one non-hydrogen atom group, but it is required that valence requirements thereof are met and a chemically stable compound thereof is generated from substitution. In the present specifications, it shall be interpreted that all the substituents may be substituted or unsubstituted, unless explicitly described as "unsubstituted" herein. Each substituent of $R_1$ and $R_2$ of the 1,3,4-oxadiazole derivative compounds the imidazole derivative according to the present invention may be substituted again with at least one of the substituents defined above.

The "alkyl" generally means linear and branched saturated hydrocarbon groups having the specified number of carbon atoms (e.g., 1 to 12 carbon atoms). Examples of an alkyl group comprise, without limitation, methyl, ethyl, n-propyl, isopropyl, n-butyl, sec-butyl, isobutyl, tert-butyl, n-pentyl, n-hexyl, n-heptyl and the like. The alkyl may be attached to a parent group or a substrate at any ring atom, unless its attachment violates valence requirements. Likewise, the alkyl or alkenyl group may comprise at least one non-hydrogen substituent, unless its attachment violates valence requirements.

The "cycloalkyl" refers to saturated monocyclic and polycyclic hydrocarbon rings generally having the specified number of carbon atoms with a ring (i.e., C3-10 cycloalkyl refers to a cycle having 3, 4, 5, 6, 7, 8, 9 or 10 carbon atoms as a ring member). The "heterocycloalkyl" refers to monocyclic and polycyclic hetero rings having 1 to 4 hetero atoms independently selected from nitrogen, oxygen and sulfur.

Examples of the heterocycloalkyl comprise, without limitation, tetrahydrofuranyl, tetrahydrothiophenyl, pyrrolidinyl, tetrahydropyranyl, tetrahydrothiopyranyl, piperidinyl and the like. The cycloalkyl and the heterocycloalkyl may be attached to a parent group or a substrate at any ring atom, unless their attachments violate valence requirements. Likewise, the cycloalkyl and the heterocycloalkyl may comprise at least one non-hydrogen substituent, unless their attachments violate valence requirements.

The "aryl" refers to monovalent aromatic groups including monocyclic or polycyclic aromatic hydrocarbon groups. The aryl further includes polycyclic rings fused with aromatic ring and cycloalkyl, such as tetrahydronaphthalenyl or dihydroindenyl. The "heteroaryl" refers to monovalent heteroaromatic monocyclic or polycyclic groups in which one or more of the aromatic group is/are is independently selected from nitrogen, oxygen and sulfur. The heteroaryl includes polycyclic rings fused with aryl and heterocycloalkyl or fused with heteroaromatic cyclic group and cycloalkyl.

Examples of a monocyclic aryl group and a heteroaryl group comprise, without limitation, phenyl, pyridinyl, furanyl, pyrrolyl, thiophenyl, thiazolyl, isothiazolyl, imidazolyl, triazolyl, tetrazolyl, pyrazolyl, oxazolyl, isoxazolyl, pyrazinyl, pyridazinyl, pyrimidinyl, naphthyl, etc. Examples of a polycyclic aryl group and a heteroaryl group comprise, without limitation, isoquinolinyl, naphthyl, biphenyl, anthracenyl, pyrenyl, carbazolyl, benzoxazolyl, benzodioxazolyl, benzodioxinyl, benzothiazolyl, benzoimidazolyl, benzothiophenyl, quinolinyl, indolyl, benzofuranyl, furinyl, indolizinyl, etc. More specific examples of aryl group and heteroaryl comprise phenyl, naphthyl,

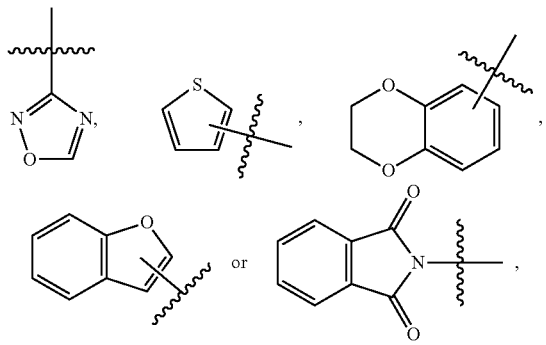

aryl group and the heteroaryl group may be attached to a parent group or a substrate at any ring atom, unless their attachments violate valence requirements. Likewise, the aryl group and the heteroaryl group may comprise at least one non-hydrogen substituent, unless their substitutions violate valence requirements. The non-hydrogen substituent of the aryl group and the heteroaryl group may be also substituted with an additional non-hydrogen substituent.

The —C(O)R' is carbonyl group. In the present specifications, the (O) means that oxygen is linked to an atom such as carbon or sulfur by means of a double bond. Here, the R' is a non-hydrogen substituent such as lower alkyl, lower alkoxy, etc. Examples of the carbonyl group comprise, without limitation, 2-methoxyoxoethyl, 3-methoxyoxopropyl, etc. The carbonyl may be attached to a parent group or a substrate at any ring atom, unless its attachment violates valence requirements. Likewise, the carbonyl group may comprise at least one non-hydrogen substituent, unless its attachment violates valence requirements.

The "alkoxy" refers to alkyl-O—, wherein the alkyl is defined above. Examples of the alkoxy group comprise, without limitation, methoxy, ethoxy, etc. The alkoxy may be attached to a parent group or a substrate at any ring atom, unless its attachment violates valence requirements. Likewise, the alkoxy group may comprise at least one non-hydrogen substituent, unless its attachment violates valence requirements.

The "akylene" is a divalent functional group of "alkane" as saturated aliphatic radical.

The "alkenylene" is divalent functional group of "alkene" as unsaturated hydrocarbon including a double bond between two carbon atoms.

Also, the 1,3,4-oxadiazole derivative compounds the imidazole derivative of the Formula 1 above may comprise a racemate thereof or a compound of an isomeric form.

Method for Preparing 1,3,4-Oxadiazole Derivative Compounds

The present invention provides a method for preparing 1,3,4-oxadiazole derivative compounds represented by the formula I, optical isomers thereof or pharmaceutically acceptable salts thereof.

In the present invention, a preferable method for preparing 1,3,4-oxadiazole derivative compounds represented by the formula I, optical isomers thereof or pharmaceutically acceptable salts thereof is as shown in following reaction formulas 1 to 5, and even a preparation method modified at a level apparent to those skilled in the art is also included therein.

$X$, $Y$, $Z$, $R_1$, $L$, $R_2$, $R_4$ and $R_5$ represented in the reaction formulas 1 to 5 are the same as defined above.

[Reaction Formula 1]

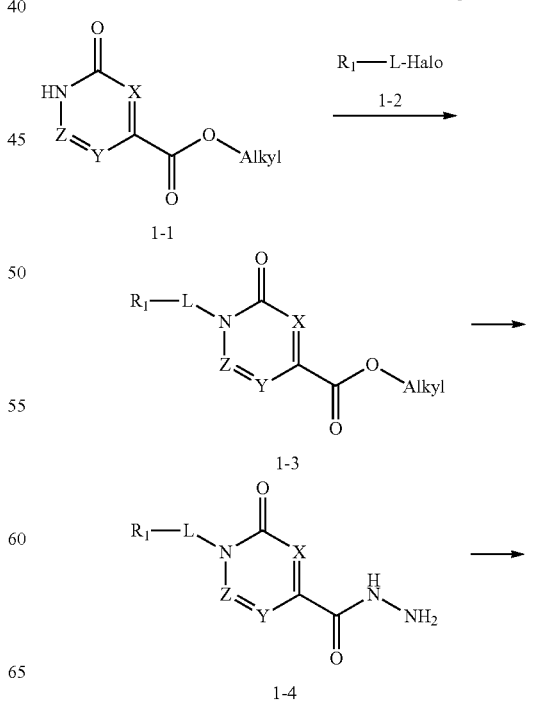

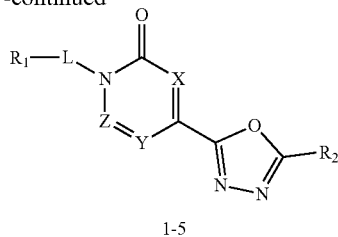

1-5

The [reaction formula 1] above is a method for preparing 1,3,4-oxadiazole derivative compounds, wherein a compound of a formula 1-3 is prepared by means of a substitution reaction between a compound of a formula 1-1 and a compound of a formula 1-2, then subjected to reaction with hydrazine to prepare a compound of a formula 1-4, and then subjected to reaction with difluoroacetic anhydride or trifluoroacetic anhydride to prepare a compound of a formula 1-5 (for example, Compound 1).

[Reaction Formula 2]

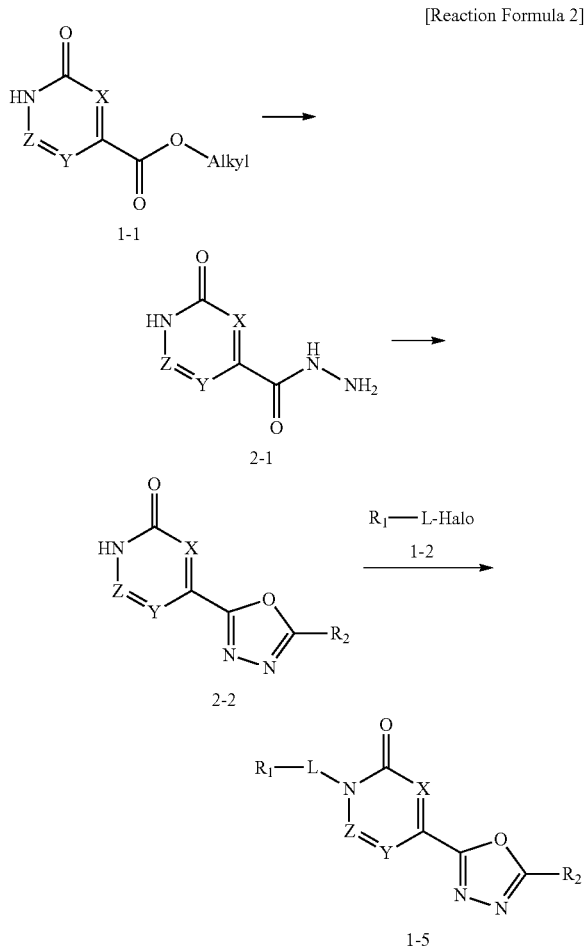

The [reaction formula 2] above is other method for preparing a compound 1-5, which may be prepared by means of the [reaction formula 1], wherein the compound of the formula 1-1, which is used in the reaction formula 1, is subjected to reaction with hydrazine to prepare a compound of a formula 2-1, and then subjected to reaction with difluoroacetic anhydride or trifluoroacetic anhydride to prepare a compound of a formula 2-2. After that, the compound of the formula 1-5 is prepared by means of a substitution reaction between the compound of the formula 2-2 and the compound of the formula 1-2.

In the present invention, as a compound prepared by means of the reaction formula above, there are compounds 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 47, 48, 49, 50, 51, 52, 53, 54, 55, 56 and the like.

[Reaction Formula 3]

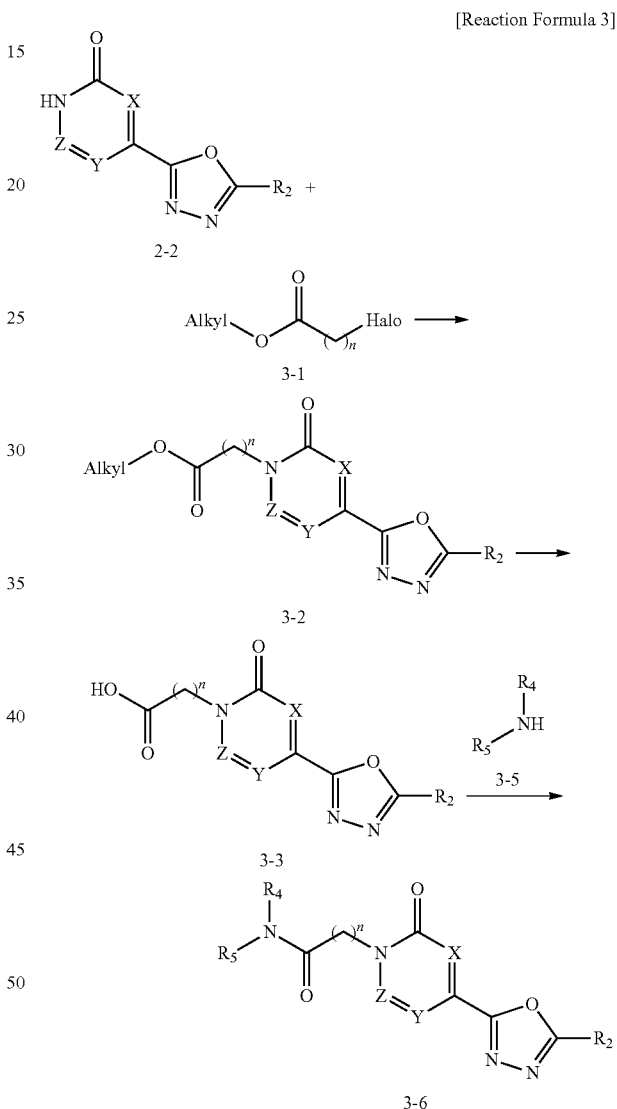

The [reaction formula 3] above is a method for synthesizing a compound having a 1,3,4-oxadiazole structure with an amide derivative included therein, wherein a compound of a formula 3-2 (for example, Compound 43) is prepared by means of a substitution reaction between the compound of the formula 2-2 and a compound of a formula 3-1, and then subjected to a hydrolysis reaction to prepare a compound of a formula 3-3. After that, a compound of a formula 3-6 (for example, Compound 46) is prepared by means of an amide coupling reaction with a compound of a formula 3-5.

[Reaction Formula 4]

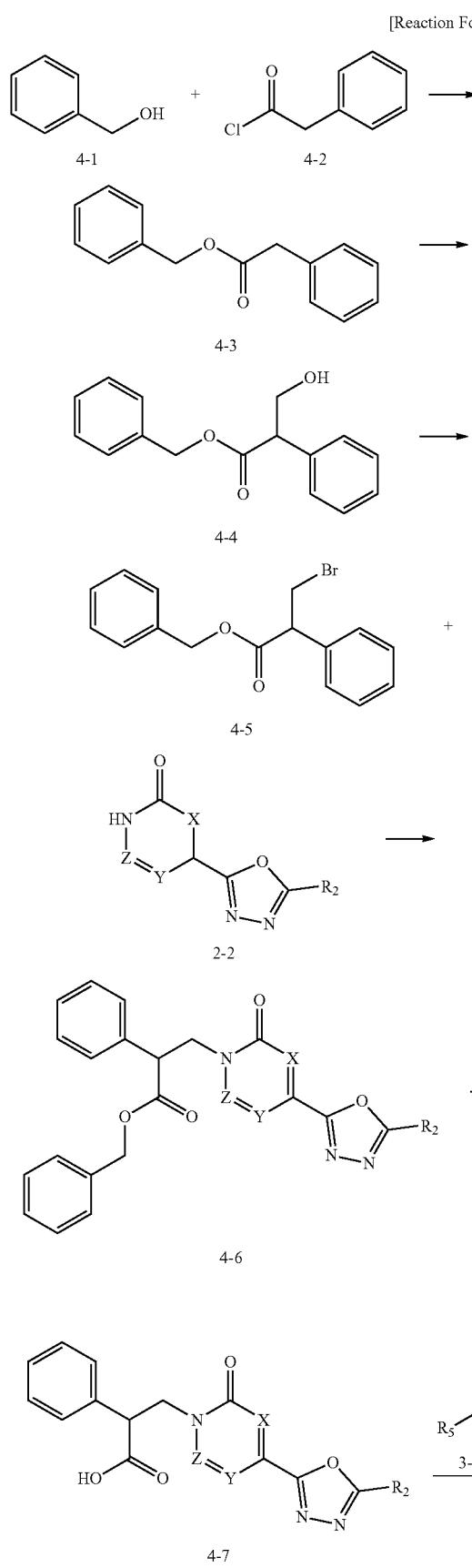

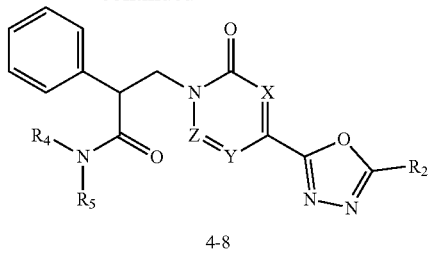

The [reaction formula 4] above is a method for preparing a compound having a 1,3,4-oxadiazole structure with an amide derivative included therein, wherein a compound of a formula 4-3 is prepared by means of an acylation reaction between a compound of a formula 4-1 and a compound of a formula 4-2, after which a compound of a formula 4-4 is prepared by means of formaldehyde. After that, a compound of a formula 4-5 is prepared through a bromination reaction, after which a compound of a formula 4-6 is prepared through a substitution reaction with the compound of the formula 2-2. A compound of a formula 4-7 is prepared through a hydrogenation reaction with the compound of the formula 4-6, after which a compound of a formula 4-8 (for example, compounds 44 and 45) is prepared through an amide coupling with a compound of the formula 3-5.

[Reaction Formula 5]

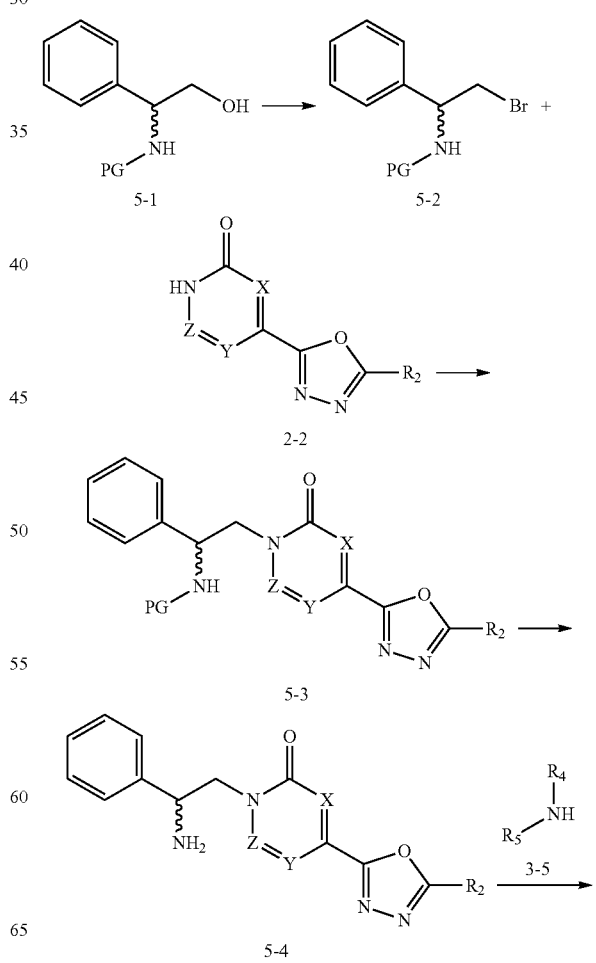

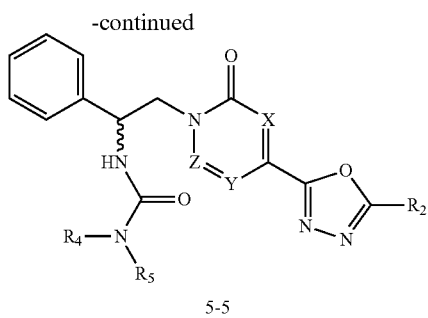

5-5

The [reaction formula 5] above is a method for preparing a compound having a 1,3,4-oxadiazole structure with a urea derivative included therein, wherein a compound of a formula 5-2 is prepared by means of a bromination reaction with a compound of a formula 5-1, after which a compound of a formula 5-3 is prepared through a substitution reaction with the compound of the formula 2-2. An amine protecting group (PG) is removed from the compound of the formula 5-3 to prepare a compound of a formula 5-4, after which a compound of a formula 5-5 (for example, compounds 57 and 58) is prepared by means of an amide coupling reaction with the compound of the formula 3-5.

Pharmaceutical Use of 1,3,4-Oxadiazole Derivative Compounds

The present invention provides a pharmaceutical use of 1,3,4-oxadiazole derivative compounds represented by a following formula I, optical isomers thereof or pharmaceutically acceptable salts thereof.

According to one embodiment aspect of the present invention, there is provided a pharmaceutical composition for preventing or treating histone deacetylase 6 activity-related diseases, containing 1,3,4-oxadiazole derivative compounds represented by a following formula I, optical isomers thereof or pharmaceutically acceptable salts thereof as an effective component:

[Formula I]

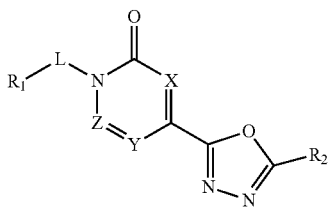

The formula I above is the same as defined above.

The pharmaceutical composition of the present invention selectively inhibits histone deacetylase 6, thereby showing a remarkable effect on preventing or treating histone deacetylase 6 activity-related diseases.

In the present invention, the histone deacetylase 6 activity-related diseases include at least one selected from infectious diseases; neoplasm; internal secretion; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, and chromosomal aberration.

The pharmaceutically acceptable salts are the same as described in the pharmaceutically acceptable salts of the compounds represented by the formula I of the present invention.

For its administration, the pharmaceutical composition of the present invention may further include at least one pharmaceutically acceptable carrier, in addition to the compounds represented by the formula I above, optical isomers thereof or pharmaceutically acceptable salts thereof. As the pharmaceutically acceptable carrier, the following may be used: saline solution, sterilized water, Ringer's solution, buffered saline, dextrose solution, maltodextrin solution, glycerol, ethanol and a mixture of at least one component thereof, and may be also used with the addition of other conventional additives such as antioxidant, buffer solution, bacteriostatic agent, etc., if needed. Also, such pharmaceutical composition may be formulated into an injectable dosage form such as aqueous solution, suspension, emulsion, etc., pill, capsule, granule or tablet with a supplementary addition of diluent, dispersing agent, surfactant, binder and lubricant. Thus, the composition of the present invention may be a patch, liquid medicine, pill, capsule, granule, tablet, suppository, etc. Such preparations may be prepared by means of a conventional method used for formulation in the field or a method disclosed in Remington's Pharmaceutical Science (latest edition), Merck Publishing Company, Easton PA, and such composition may be formulated into various preparations according to each disease or component.

The composition of the present invention may be orally or parenterally administered (for example, applied intravenously, hypodermically, intraperitoneally or locally) according to an intended method, and a dosage thereof has various ranges depending on a patient's weight, age, gender, health condition, diet, administration time, administration method, excretion rate, severity of a disease and the like. A daily dosage of the compounds represented by the formula I of the present invention is about 1 to 1000 mg/kg, preferably 5 to 100 mg/kg, and may be administered once a day or divided into several times a day.

The pharmaceutical composition of the present invention may further include at least one effective component, which shows the same or similar medicinal effect, in addition to the compounds represented by the formula I above, optical isomers thereof or pharmaceutically acceptable salts thereof.

The present invention provides a method for preventing or treating histone deacetylase 6 activity-related diseases, including a step of administering a therapeutically effective amount of the compounds represented by the formula I above, optical isomers thereof or pharmaceutically acceptable salts thereof.

As used herein, the term "therapeutically effective amount" refers to an amount of the compounds represented by the formula I above, which is effective in preventing or treating histone deacetylase 6 activity-related diseases.

Also, the present invention provides a method for selectively inhibiting HDAC6 by administering the compounds represented by the formula I above, optical isomers thereof or pharmaceutically acceptable salts thereof into mammals including humans.

The method for preventing or treating histone deacetylase 6 activity-related diseases according to the present invention encompasses not only dealing with the diseases themselves before expression of their symptoms, but also inhibiting or avoiding such symptoms by administering the compounds represented by the formula I above. In managing diseases, a preventive or therapeutic dose of a certain active component may vary depending on a nature and severity of diseases or conditions and a route of administering the active component. A dose and a frequency thereof may vary depending on an individual patient's age, weight and reactions. A suitable dose and usage may be easily selected by those having ordinary skill in the art, naturally considering such factors. Also, the method for preventing or treating histone deacetylase 6 activity-related diseases according to the present invention may further include a step of administering a therapeutically effective amount of an additional active agent, which is helpful in treating the diseases, along with the compounds represented by the formula I above, wherein the additional active agent may show a synergy effect or an additive effect together with the compounds of the formula I above.

The present invention is also intended to provide a use of the compounds represented by the formula I above, optical isomers thereof or pharmaceutically acceptable salts thereof in preparing a drug for treating histone deacetylase 6 activity-related diseases. The compounds represented by the formula I above for preparing a drug may be combined with an acceptable adjuvant, diluent, carrier, etc., and may be prepared into a complex preparation together with other active agents, thus having a synergy action of active components.

Matters mentioned in the use, composition and therapeutic method of the present invention are equally applied, if not contradictory to each other.

Advantageous Effects of Invention

According to the present invention, the compounds represented by the formula I above, optical isomers thereof or pharmaceutically acceptable salts thereof may selectively inhibit HDAC6, thus having a remarkably excellent effect of preventing or treating histone deacetylase 6 activity-related diseases.

MODE FOR THE INVENTION

Hereinafter, the present invention will be described in more detail through the following examples and experimental examples. However, the following examples, etc. are provided only for the purpose of illustrating the present invention, and thus the scope of the present invention is not limited thereto.

Example 1: Compound 1, 4-(5-(difluoromethyl)-1,3,4-oxadiazole-2-yl)-1-(naphthalene-2-ylmethyl)pyridine-2(1H)-one

[Step 1] Synthesis of methyl 1-(naphthalene-2-ylmethyl)-2-oxo-1,2-dihydropyridine-4-carboxylate

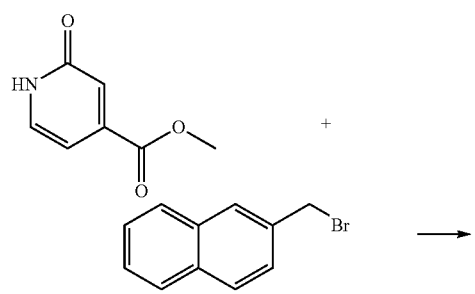

-continued

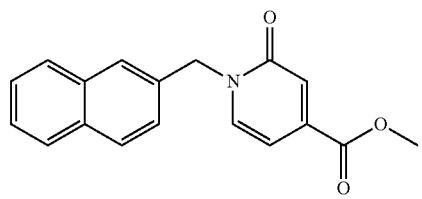

Methyl 2-oxo-1,2-dihydropyridine-4-carboxylate (1.730 g, 11.297 mmol) was dissolved in N,N-dimethylformamide (30 mL) at 0° C., after which hydrogenated sodium (60.00%, 0.678 g, 16.945 mmol) was added into the resulting solution, and stirred at the same temperature for 30 minutes. 2-(bromomethyl)naphthalene (2.498 g, 11.297 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 30%), and concentrated to obtain the title compound (2.800 g, 84.5%) in a white solid form.

[Step 2] Synthesis of 1-(naphthalene-2-ylmethyl)-2-oxo-1,2-dihydropyridine-4-carbohydrazide

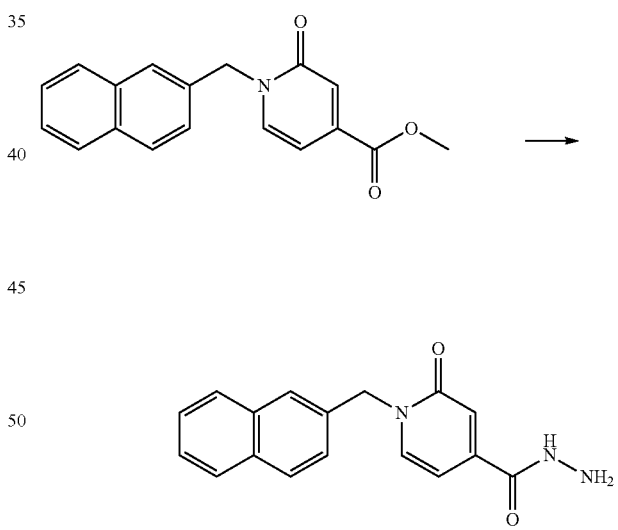

Methyl 1-(naphthalene-2-ylmethyl)-2-oxo-1,2-dihydropyridine-4-carboxylate (0.560 g, 1.909 mmol) prepared in the step 1 and hydrazine monohydrate (1.856 mL, 38.184 mmol) were dissolved in ethanol (10 mL) at 80° C., after which the resulting solution was stirred at the same temperature for 12 hours, and then a reaction was finished by lowering the temperature to room temperature. Solvent was removed from the reaction mixture under reduced pressure, after which a product obtained was used without an additional purification process (title compound, 0.560 g, 100.0%, white solid).

[Step 3] Synthesis of Compound 1

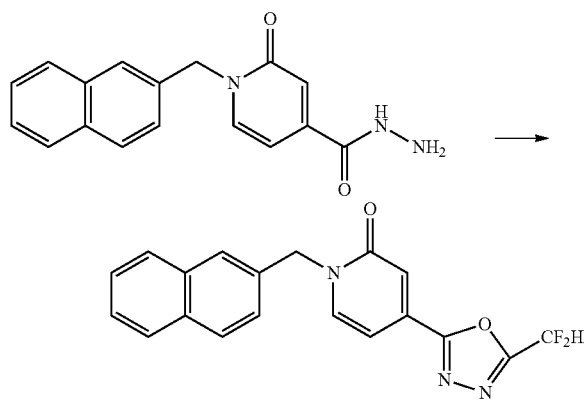

1-(naphthalene-2-ylmethyl)-2-oxo-1,2-dihydropyridine-4-carbohydrazide (0.500 g, 1.705 mmol) prepared in the step 2, 2,2-difluoroacetic anhydride (0.636 mL, 5.114 mmol) and imidazole (0.348 g, 5.114 mmol) were dissolved in dichloromethane (10 mL) at 45° C., after which the resulting solution was stirred at the same temperature for 12 hours, and then a reaction was finished by lowering the temperature to room temperature. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography ($SiO_2$, 12 g cartridge; ethyl acetate/hexane=0 to 50%), and concentrated to obtain the title compound (0.440 g, 73.1%) in a white solid form.

$^1$H NMR (400 MHz, $CDCl_3$) δ 7.89~7.84 (m, 3H), 7.80 (s, 1H), 7.56~7.51 (m, 3H), 4.45~7.41 (m, 2H), 7.07 (s, 0.25H), 6.94 (s, 0.5H), 6.93 (dd, J=7.1, 1.9 Hz, 1H), 6.81 (s, 0.25H), 5.40 (s, 2H); LRMS (ES) m/z 354.3 ($M^+$+1).

Example 2: Synthesis of Compound 2, 1-benzyl-4-(5-(difluoromethyl)-1,3,4-oxadiazole-2-yl)pyridine-2(1H)-one

[Step 1] Synthesis of 2-oxo-1,2-dihydropyridine-4-carbohydrazide

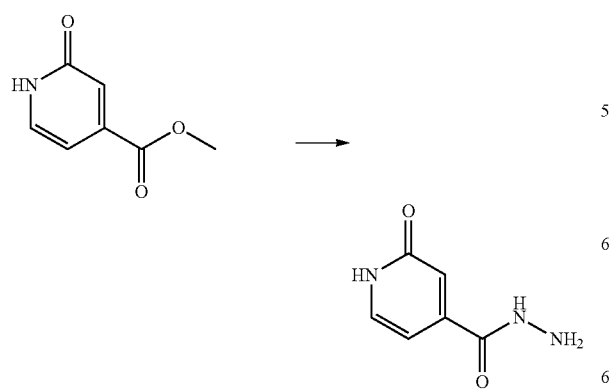

Methyl 2-oxo-1,2-dihydropyridine-4-carboxylate (1.000 g, 6.530 mmol) and hydrazine monohydrate (6.347 mL, 130.599 mmol) were dissolved in ethanol (20 mL) at 80° C., after which the resulting solution was stirred at the same temperature for 12 hours, and then a reaction was finished by lowering the temperature to room temperature. A precipitated solid was filtered, then washed with hexane, and then dried to obtain the title compound (1.000 g, 100.0%) in a white solid form.

[Step 2] Synthesis of 4-(5-(difluoromethyl)-1,3,4-oxadiazole-2-yl)pyridine-2(1H)-one

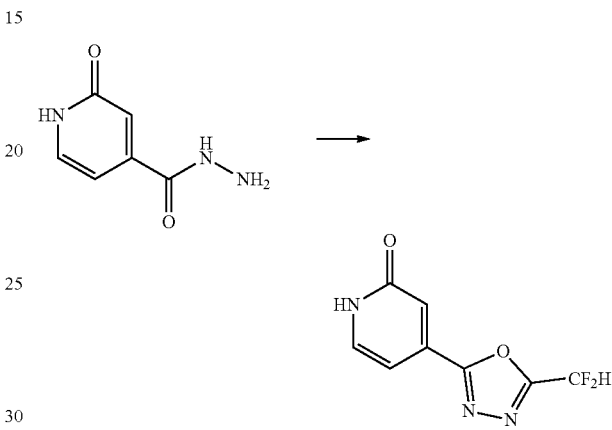

2-oxo-1,2-dihydropyridine-4-carbohydrazide (1.000 g, 6.530 mmol) prepared in the step 1, 2,2-difluoroacetic anhydride (2.435 mL, 19.590 mmol) and imidazole (1.334 g, 19.590 mmol) were dissolved in dichloromethane (30 mL) at 45° C., after which the resulting solution was stirred at the same temperature for 12 hours, and then a reaction was finished by lowering the temperature to room temperature. A precipitated solid was filtered, then washed with hexane, and then dried to obtain the title compound (1.100 g, 79.0%) in a white solid form.

[Step 3] Synthesis of Compound 2

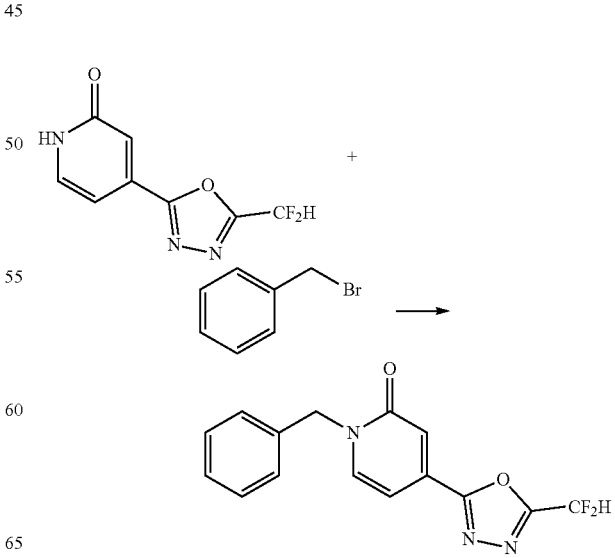

4-(5-(difluoromethyl)-1,3,4-oxadiazole-2-yl)pyridine-2 (1H)-one (0.100 g, 0.469 mmol) prepared in the step 2 was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. (Bromomethyl)benzene (0.084 mL, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.080 g, 56.2%) in a yellow solid form.

$^1$H NMR (400 MHz, CDCl$_3$) δ 7.48 (dd, J=7.1, 0.6 Hz, 1H), 7.40~7.30 (m, 6H), 7.06 (s, 0.25H), 6.93 (s, 0.5H), 6.84 (dd, J=7.1, 1.9 Hz, 1H), 6.80 (s, 0.25H), 5.20 (s, 2H); LRMS (ES) m/z 304.3 (M$^+$+1).

Example 3: Synthesis of Compound 3, 4-(5-(difluoromethyl)-1,3,4-oxadiazole-2-yl)-1-(2-oxo-2-phenylethyl)pyridine-2(1H)-one

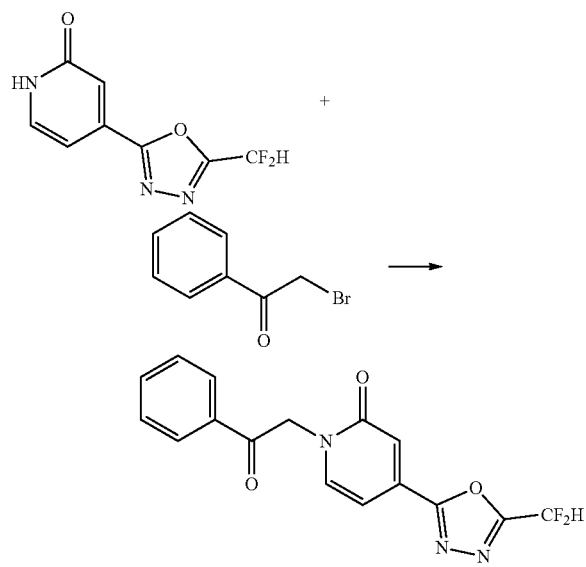

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-bromo-1-phenylethane-1-one (0.140 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.090 g, 57.9%) in a white solid form.

$^1$H NMR (400 MHz, CDCl$_3$) δ 8.06 (d, J=7.5 Hz, 2H), 7.69 (t, J=7.3 Hz, 1H), 7.56 (t, J=7.5 Hz, 2H), 7.41 (d, J=8.7 Hz, 1H), 7.34 (s, 1H), 7.08 (s, 0.25H), 6.97~6.95 (m, 1H), 6.95 (s, 0.5H), 6.82 (s, 0.25H), 5.46 (s, 2H); LRMS (ES) m/z 332.4 (M$^+$+1).

Example 4: Synthesis of Compound 4, 4-(5-(difluoromethyl)-1,3,4-oxadiazole-2-yl)-1-methylpyridine-2 (1H)-one

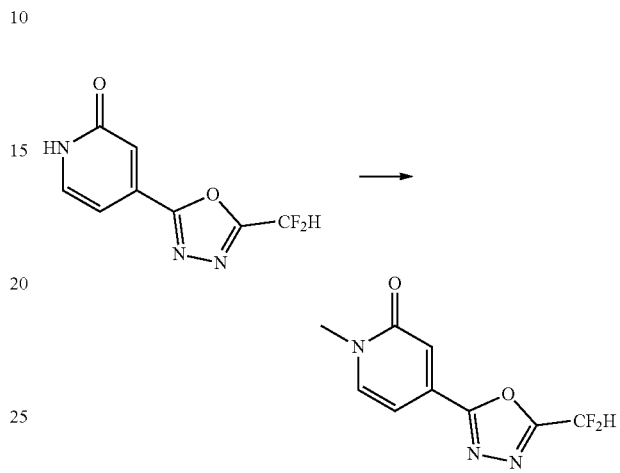

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. Iodomethane (0.044 mL, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.070 g, 65.7%) in a colorless oil form.

$^1$H NMR (400 MHz, CDCl$_3$) δ 7.50 (d, J=7.1 Hz, 1H), 7.28 (s, 1H), 7.07 (s, 0.25H), 6.94 (s, 0.5H), 6.86 (dd, J=7.0, 1.9 Hz, 1H), 6.81 (s, 0.25H), 3.63 (s, 3H); LRMS (ES) m/z 228.3 (M$^+$+1).

Example 5: Synthesis of Compound 5, 1-cinnamyl-4-(5-(difluoromethyl)-1,3,4-oxadiazole-2-yl)pyridine-2(1H)-one

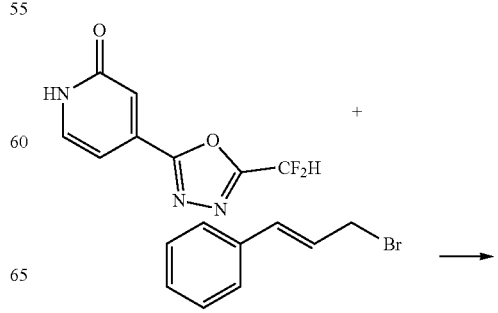

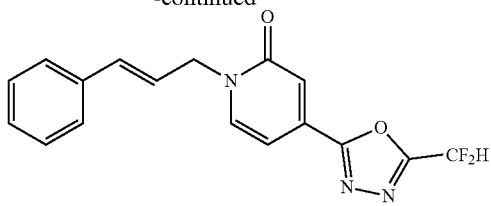

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. (E)-(3-bromoprop-1-en-1-yl)benzene (0.139 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 64.7%) in a white solid form.

$^1$H NMR (400 MHz, CDCl$_3$) δ 7.55 (d, J=7.1 Hz, 1H), 7.41~7.39 (m, 2H), 7.35~7.26 (m, 4H), 7.07 (s, 0.25H), 6.94 (s, 0.5H), 6.89 (dd, J=7.1, 1.9 Hz, 1H), 6.81 (s, 0.25H), 6.67 (d, J=15.8 Hz, 1H), 4.79 (dd, J=6.6, 1.0 Hz, 2H); LRMS (ES) m/z 330.4 (M$^+$+1).

Example 6: Synthesis of Compound 6, 1-(2-(1H-pyrazole-1-yl)ethyl)-4-(5-(difluoromethyl)-1,3,4-oxadiazole-2-yl)pyridine-2(1H)-one

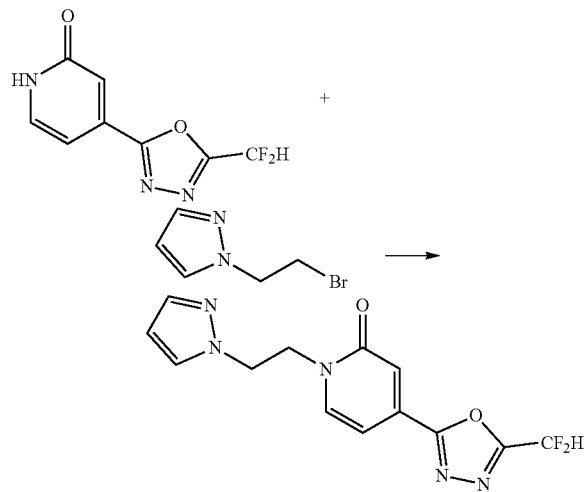

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(2-bromoethyl)-1H-pyrazole (0.123 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain a desired compound (0.070 g, 48.6%) in a white solid form.

$^1$H NMR (400 MHz, CDCl$_3$) δ 7.60 (dd, J=1.9, 0.6 Hz, 1H), 7.28 (dd, J=1.9, 0.6 Hz, 1H), 7.17 (dd, J=2.3, 0.6 Hz, 1H), 7.08 (s, 0.25H), 6.92 (s, 0.5H), 6.80 (s, 0.25H), 6.62 (dd, J=7.1, 1.9 Hz, 1H), 6.18 (dd, J=2.2, 2.0 Hz, 1H), 4.58~4.54 (m, 2H), 4.51~4.47 (m, 2H); LRMS (ES) m/z 366.1 (M$^+$+1).

Example 7: Synthesis of Compound 7, 4-(5-(difluoromethyl)-1,3,4-oxadiazole-2-yl)-1-(2-(naphthalene-2-yl)-2-oxoethyl)pyridine-2(1H)-one

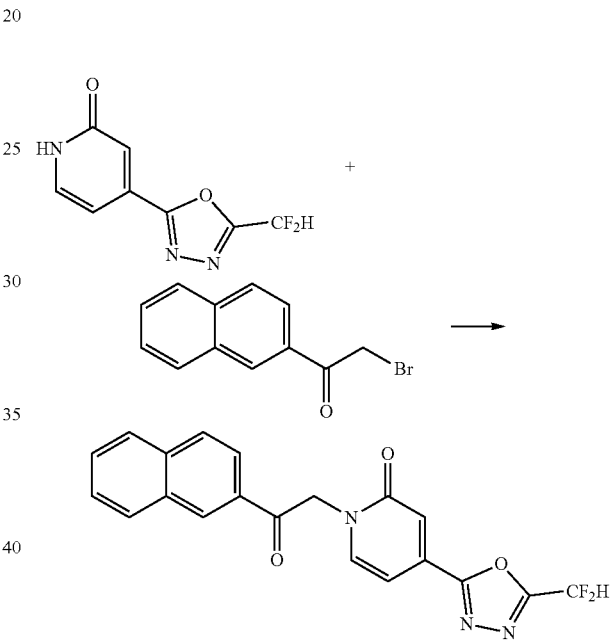

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-bromo-1-(naphthalene-2-yl)ethane-1-one (0.175 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.080 g, 44.7%) in a white solid form.

$^1$H NMR (400 MHz, CDCl$_3$) δ 8.61 (s, 1H), 8.05-6.61 (m, 6H), 7.48 (dd, J=7.1, 0.6 Hz, 1H), 7.34 (dd, J=1.9, 0.5 Hz, 1H), 7.08 (s, 0.25H), 6.79~6.95 (m, 1H), 6.95 (s, 0.5H), 6.82 (s, 0.25H), 5.60 (s, 2H); LRMS (ES) m/z 382.4 (M$^+$+1).

Example 8: Synthesis of Compound 8, 4-(5-(difluoromethyl)-1,3,4-oxadiazole-2-yl)-1-(3,5-dimethoxyphenethyl)pyridine-2(1H)-one

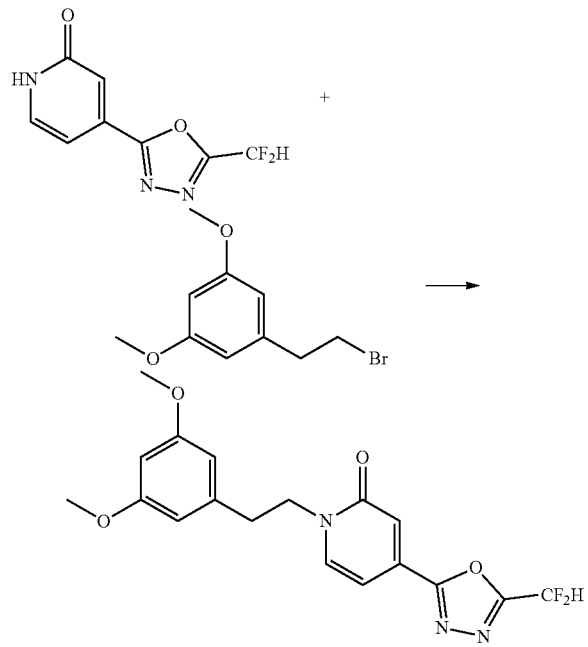

4-(5-(difluoromethyl)-1,3,4-oxadiazole-2-yl)pyridine-2(1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(2-bromoethyl)-3,5-dimethoxybenzene (0.173 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.050 g, 28.2%) in a white solid form.

$^1$H NMR (400 MHz, CDCl$_3$) δ 7.42 (d, J=7.1 Hz, 1H), 7.34 (d, J=1.8 Hz, 1H), 7.17 (d, J=2.2 Hz, 2H), 7.08 (s, 0.25H), 6.95 (dd, J=7.1, 1.9 Hz, 1H), 6.95 (s, 0.5H), 6.82 (s, 0.25H), 6.74 (t, J=2.2 Hz, 1H), 5.54 (s, 2H), 3.37 (s, 6H); LRMS (ES) m/z 392.3 (M$^+$+1).

Example 9: Synthesis of Compound 9, 1-(2-(1,3-dioxane-2-yl)ethyl)-4-(5-(difluoromethyl)-1,3,4-oxadiazole-2-yl)pyridine-2(1H)-one

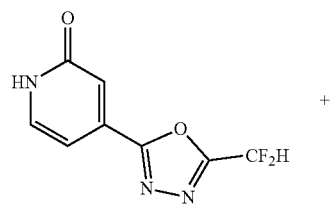

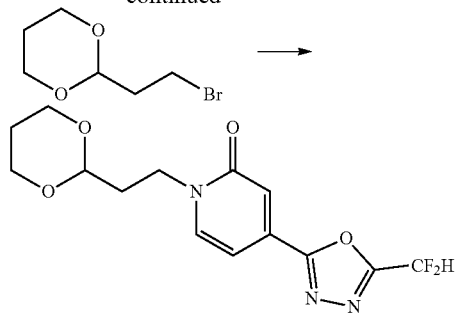

4-(5-(difluoromethyl)-1,3,4-oxadiazole-2-yl)pyridine-2(1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-(2-bromoethyl)-1,3-dioxane (0.137 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.080 g, 52.1%) in a colorless oil form.

$^1$H NMR (400 MHz, CDCl$_3$) δ 7.51 (d, J=7.1 Hz, 1H), 7.22 (d, J=1.8 Hz, 1H), 7.05 (s, 0.25H), 6.93 (s, 0.5H), 6.82~6.79 (m, 1H), 6.80 (s, 0.25H), 5.31 (s, 2H), 4.41 (t, J=108.0 Hz, 1H), 4.12~4.06 (m, 4H), 3.75~3.69 (m, 2H), 2.10~1.99 (m, 2H); LRMS (ES) m/z 328.4 (M$^+$+1).

Example 10: Synthesis of Compound 10, 1-(2,5-difluorobenzyl)-4-(5-(difluoromethyl)-1,3,4-oxadiazole-2-yl)pyridine-2(1H)-one

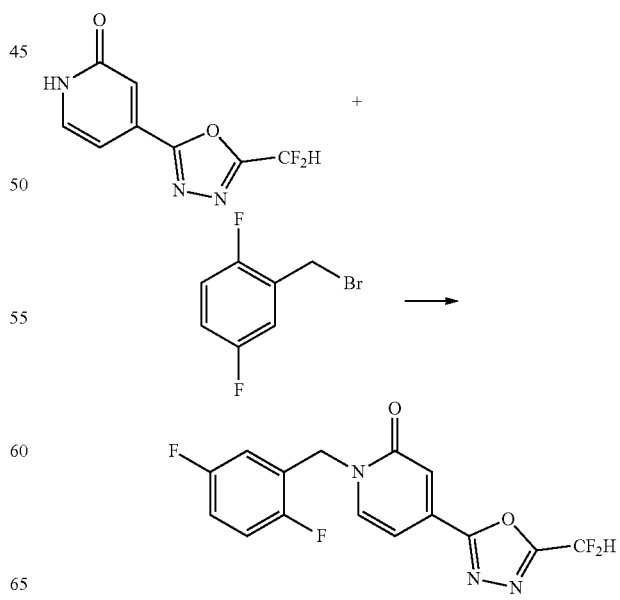

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-(bromomethyl)-1,4-difluorobenzene (0.146 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.080 g, 50.3%) in a yellow solid form.

$^1$H NMR (400 MHz, CDCl$_3$) δ 7.61~7.59 (m, 1H), 7.27 (dd, J=1.9, 0.6 Hz, 1H), 7.22~7.18 (m, 1H), 7.10~6.98 (m, 2H), 7.07 (s, 0.25H), 6.93 (s, 0.5H), 6.88 (dd, J=7.2, 2.0 Hz, 1H), 6.81 (s, 0.25H), 5.17 (s, 2H); LRMS (ES) m/z 340.3 (M$^+$+1).

Example 11: Synthesis of Compound 11, 1-(2-(diethylamino)ethyl)-4-(5-(difluoromethyl)-1,3,4-oxadiazole-2-yl)pyridine-2(1H)one

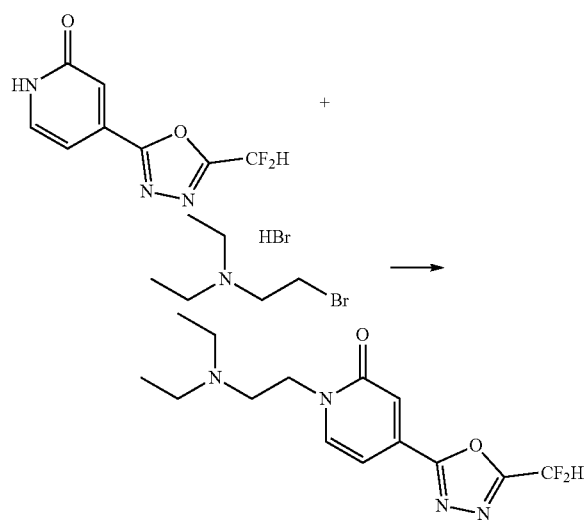

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-bromo-N,N-diethylethane-1-amine hydrobromide (0.184 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.110 g, 75.1%) in a white solid form.

$^1$H NMR (400 MHz, CDCl$_3$) δ 7.53 (d, J=7.0 Hz, 1H), 7.24 (d, J=1.8 Hz, 1H), 7.06 (s, 0.25H), 6.93 (s, 0.5H), 6.82~6.80 (m, 1H), 6.80 (s, 0.25H), 4.01 (t, J=5.9 Hz, 2H), 2.78~2.74 (m, 2H), 2.56~2.50 (m, 4H), 0.96~0.90 (m, 6H); LRMS (ES) m/z 313.4 (M$^+$+1).

Example 12: Synthesis of Compound 12, 1-(2-chlorobenzyl)-4-(5-(difluoromethyl)-1,3,4-oxadiazole-2-yl)pyridine-2(1H)-one

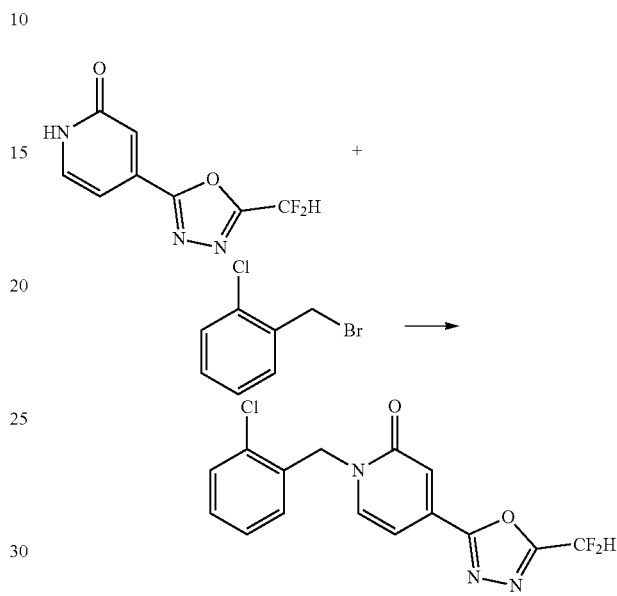

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(bromomethyl)-2-chlorobenzene (0.145 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.110 g, 69.4%) in a white solid form.

$^1$H NMR (400 MHz, CDCl$_3$) δ 7.53 (d, J=7.2 Hz, 1H), 7.43~7.40 (m, 1H), 7.34~7.30 (m, 1H), 7.29~7.24 (m, 3H), 7.06 (s, 0.25H), 6.93 (s, 0.5H), 6.84 (dd, J=7.2, 2.0 Hz, 1H), 6.80 (s, 0.25H), 5.29 (s, 2H); LRMS (ES) m/z 338.3 (M$^+$+1).

Example 13: Synthesis of Compound 13, 4-(5-(difluoromethyl)-1,3,4-oxadiazole-2-yl)-1-(2,4,5-trifluorobenzyl)pyridine-2(1H)-one

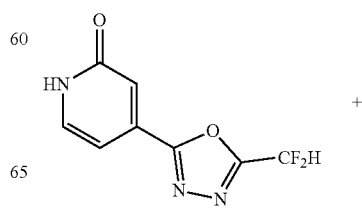

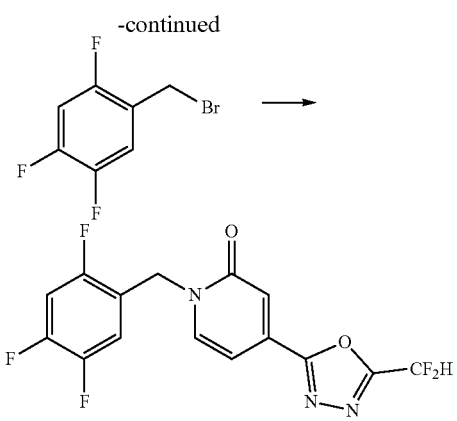

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(bromomethyl)-2,4,5-trifluorobenzene (0.158 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.130 g, 77.6%) in a white solid form.

$^1$H NMR (400 MHz, CDCl$_3$) δ 7.60 (d, J=7.1 Hz, 1H), 7.48~7.42 (m, 1H), 7.29~7.28 (m, 1H), 7.06 (s, 0.25H), 7.03~6.96 (m, 1H), 6.93 (s, 0.5H), 6.90 (dd, J=7.2, 1.9 Hz, 1H), 6.81 (s, 0.25H), 5.14 (s, 2H); LRMS (ES) m/z 358.3 (M$^+$+1).

Example 14: Synthesis of Compound 14, 4-(5-(difluoromethyl)-1,3,4-oxadiazole-2-yl)-1-(3-fluorobenzyl)pyridine-2(1H)-one

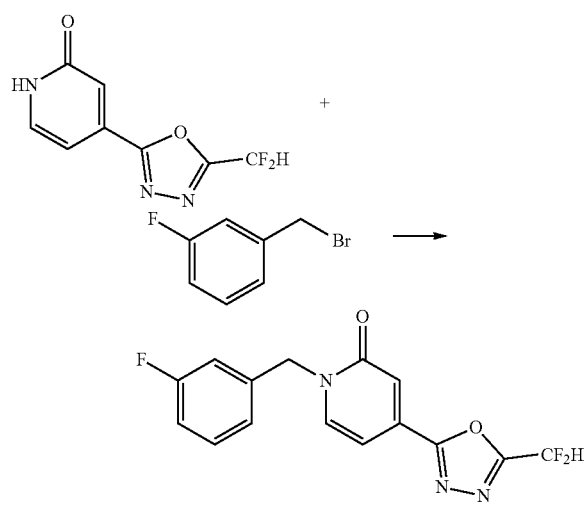

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(bromomethyl)-3-fluorobenzene (0.133 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 66.3%) in a white solid form.

$^1$H NMR (400 MHz, CDCl$_3$) δ 7.48 (dd, J=7.1, 0.7 Hz, 1H), 7.38~7.32 (m, 2H), 7.13~7.11 (m, 1H), 7.07 (s, 0.25H), 7.06~7.03 (m, 2H), 6.94 (s, 0.5H), 6.90 (dd, J=13.4, 11.4 Hz, 1H), 6.81 (s, 0.25H), 5.19 (s, 2H); LRMS (ES) m/z 322.3 (M$^+$+1).

Example 15: Synthesis of Compound 15, benzyl 2-(4-(5-(difluoromethyl)-1,3,4-oxadiazole-2-yl)-2-oxopyridine-1(2H)-yl)acetate

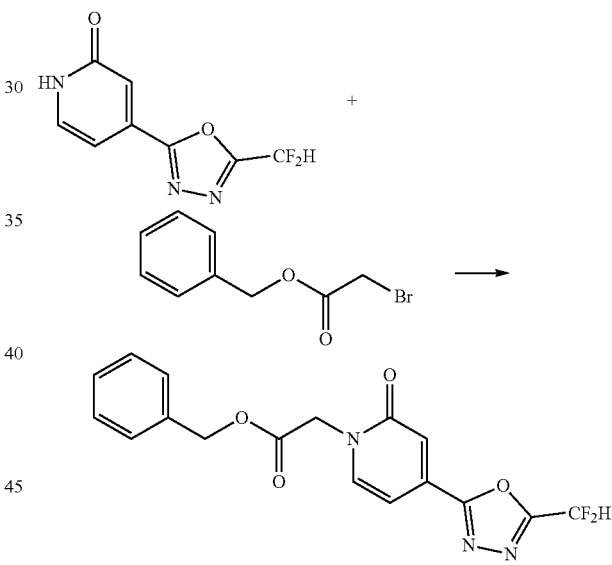

4-(5-(difluoromethyl)-1,3,4-oxadiazole-2-yl)pyridine-2 (1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. Benzyl 2-bromoacetate (0.161 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 59.0%) in a white solid form.

$^1$H NMR (400 MHz, CDCl$_3$) δ 7.42 (d, J=7.1 Hz, 1H), 7.47~7.31 (m, 5H), 7.30 (d, J=2.9 Hz, 1H), 7.07 (s, 0.25H), 6.94 (s, 0.5H), 6.92 (dd, J=9.2, 7.3 Hz, 1H), 6.81 (s, 0.25H), 5.25 (s, 2H), 4.76 (s, 2H); LRMS (ES) m/z 362.3 (M⁺+1).

Example 16: Synthesis of Compound 16, 2-(4-(5-(difluoromethyl)-1,3,4-oxadiazole-2-yl)-2-oxopyridine-1(2H)-yl)ethyl

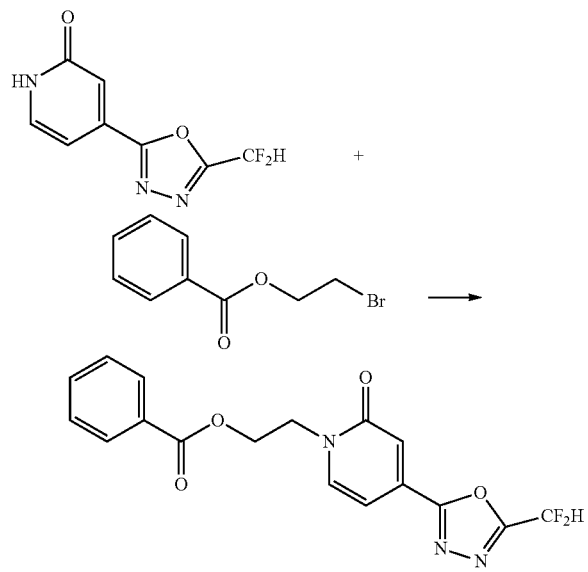

4-(5-(difluoromethyl)-1,3,4-oxadiazole-2-yl)pyridine-2(1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 2-bromoethyl benzoate (0.161 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.100 g, 59.0%) in a white solid form.
¹H NMR (400 MHz, CDCl₃) δ 8.37 (dd, J=5.3, 0.7 Hz, 1H), 8.09~8.05 (m, 2H), 7.60~7.56 (m, 2H), 7.48~7.43 (m, 3H), 7.07 (s, 0.25H), 6.94 (s, 0.5H), 6.82 (s, 0.25H), 4.78~4.68 (m, 4H); LRMS (ES) m/z 362.3 (M⁺+1).

Example 17: Synthesis of Compound 17, 4-(5-(difluoromethyl)-1,3,4-oxadiazole-2-yl)-1-(2-fluorobenzyl)pyridine-2(1H)-one

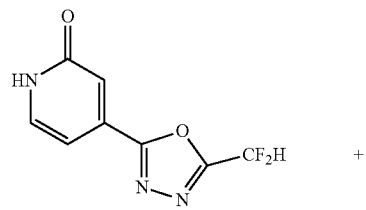

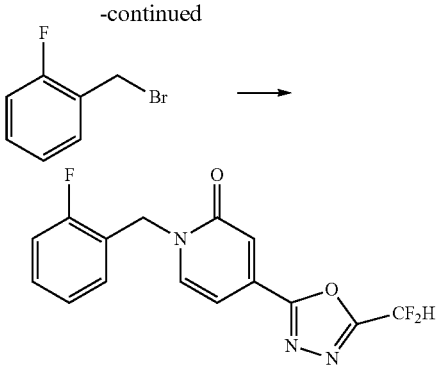

4-(5-(difluoromethyl)-1,3,4-oxadiazole-2-yl)pyridine-2(1H)-one (0.100 g, 0.469 mmol) was dissolved in N,N-dimethylformamide (5 mL) at 0° C., after which hydrogenated sodium (60.00%, 0.028 g, 0.704 mmol) was added into the resulting solution, and stirred at the same temperature for 30 minutes. 1-(bromomethyl)-2-fluorobenzene (0.133 g, 0.704 mmol) was added into the reaction mixture, and further stirred at room temperature for two hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.100 g, 66.3%) in a white solid form.
¹H NMR (400 MHz, CDCl₃) δ 7.61~7.59 (m, 1H), 7.51 (td, J=7.6, 1.7 Hz, 1H), 7.37~7.34 (m, 1H), 7.28~7.27 (m, 1H), 7.18~7.08 (m, 2H), 7.06 (s, 0.25H), 6.93 (s, 0.5H), 6.86 (dd, J=7.1, 2.0 Hz, 1H), 6.80 (s, 0.25H), 5.18 (s, 2H); LRMS (ES) m/z 322.3 (M⁺+1).

Example 18: Synthesis of Compound 18, 1-(2-(3,4-dichlorophenyl)-2-oxoethyl)-4-(5-(difluoromethyl)-1,3,4-oxadiazole-2-yl)pyridine-2(1H)-one

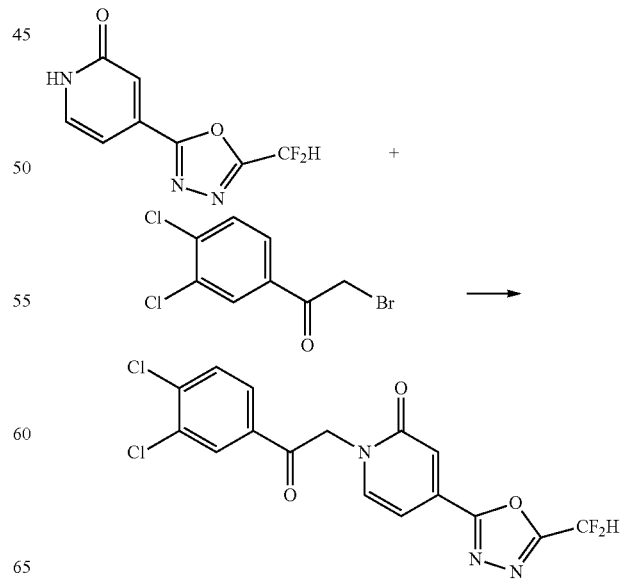

4-(5-(difluoromethyl)-1,3,4-oxadiazole-2-yl)pyridine-2 (1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(3,4-dichlorophenyl)ethane-1-one (0.189 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.080 g, 42.6%) in a white solid form.

$^1$H NMR (400 MHz, CDCl$_3$) δ 8.13~8.12 (m, 1H), 7.90~7.86 (m, 1H), 7.65~7.61 (m, 1H), 7.45~7.41 (m, 1H), 7.33 (d, J=1.6 Hz, 1H), 7.08 (s, 1H), 6.98 (dd, J=7.1, 1.9 Hz, 1H), 6.96 (s, 1H), 6.83 (s, 1H), 5.32 (s, 2H); LRMS (ES) m/z 400.3 (M$^+$+1).

Example 19: Synthesis of Compound 19, 1-(2-(4-chlorophenyl)-2-oxoethyl)-4-(5-(difluoromethyl)-1,3,4-oxadiazole-2-yl)pyridine-2(1H)-one

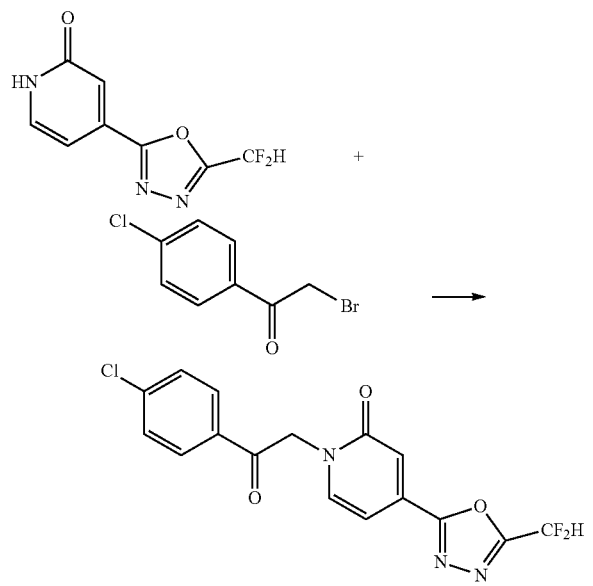

4-(5-(difluoromethyl)-1,3,4-oxadiazole-2-yl)pyridine-2 (1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(4-chlorophenyl)ethane-1-one (0.164 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.100 g, 58.3%) in a white solid form.

$^1$H NMR (400 MHz, CDCl$_3$) δ 8.02~7.97 (m, 2H), 7.54~7.51 (m, 2H), 7.43 (d, J=7.1 Hz, 1H), 7.33 (d, J=1.8 Hz, 1H), 7.08 (s, 0.25H), 6.97 (dd, J=7.1, 1.8 Hz, 1H), 6.95 (s, 0.5H), 6.82 (s, 0.25H), 5.40 (s, 2H); LRMS (ES) m/z 366.3 (M$^+$+1).

Example 20: Synthesis of Compound 20, 4-(5-(difluoromethyl)-1,3,4-oxadiazole-2-yl)-1-(2-(2,4-dimethoxyphenyl)-2-oxoethyl) pyridine-2(1H)-one

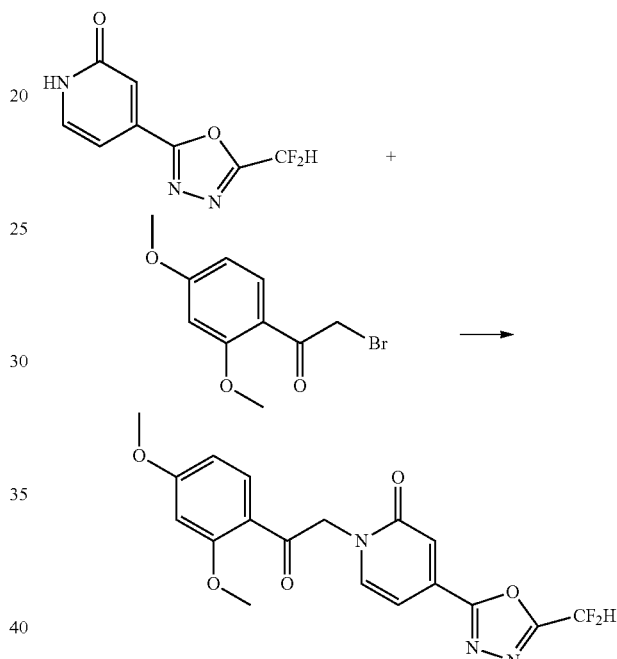

4-(5-(difluoromethyl)-1,3,4-oxadiazole-2-yl)pyridine-2 (1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(2,4-dimethoxyphenyl)ethane-1-one (0.182 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.110 g, 59.9%) in a white solid form.

$^1$H NMR (400 MHz, CDCl$_3$) δ 8.00 (d, J=8.8 Hz, 1H), 7.39 (dd, J=7.1, 0.7 Hz, 1H), 7.32 (dd, J=1.9, 0.6 Hz, 1H), 7.07 (s, 0.25H), 6.94 (s, 0.5H), 6.91 (dd, J=7.1, 1.9 Hz, 1H), 6.81 (s, 0.25H), 6.60 (dd, J=8.9, 2.3 Hz, 1H), 6.52 (d, J=2.3 Hz, 1H), 5.35 (s, 2H), 3.99 (s, 3H), 3.89 (s, 3H); LRMS (ES) m/z 392.4 (M$^+$+1).

Example 21: Synthesis of Compound 21, 4-(5-(difluoromethyl)-1,3,4-oxadiazole-2-yl)-1-((2,3-dihydrobenzo[b][1,4]dioxin-6-yl) methyl)pyridine-2(1H)-one

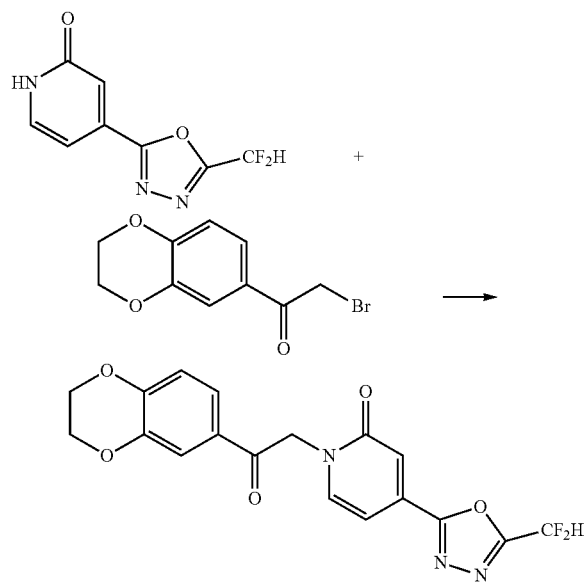

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 6-(bromomethyl)-2,3-dihydrobenzo[b][1,4]dioxin (0.181 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.090 g, 49.3%) in a white solid form.

$^1$H NMR (400 MHz, CDCl$_3$) δ 7.51 (dd, J=7.9, 1.6 Hz, 1H), 7.41 (d, J=7.1 Hz, 1H), 7.30 (d, J=1.8 Hz, 1H), 7.11 (dd, J=8.0, 1.7 Hz, 1H), 7.07 (s, 0.25H), 6.95 (d, J=3.0 Hz, 1H), 6.93 (s, 0.5H), 6.91~6.88 (m, 1H), 6.81 (s, 0.25H), 5.36 (s, 2H), 4.47~4.43 (m, 2H), 4.14~4.10 (m, 2H); LRMS (ES) m/z 390.3 (M$^+$+1).

Example 22: Synthesis of Compound 22, 4-(5-(difluoromethyl)-1,3,4-oxadiazole-2-yl)-1-(2-(3-methoxyphenyl)-2-oxoethyl)pyridine-2(1H)-one

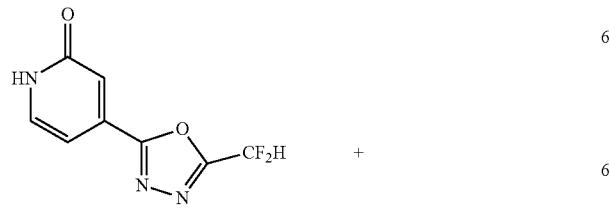

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(3-methoxyphenyl)ethane-1-one (0.161 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 59.0%) in a white solid form.

$^1$H NMR (400 MHz, CDCl$_3$) δ 7.62 (d, J=7.6 Hz, 1H), 7.54 (t, J=1.8 Hz, 1H), 7.45 (t, J=7.9 Hz, 1H), 7.43 (d, J=7.1 Hz, 1H), 7.31 (d, J=1.6 Hz, 1H), 7.20 (dd, J=8.3, 2.6 Hz, 1H), 7.08 (s, 0.25H), 6.95 (s, 0.5H), 6.93 (dd, J=7.1, 1.8 Hz, 1H), 6.82 (s, 0.25H), 5.43 (s, 2H), 3.87 (s, 3H); LRMS (ES) m/z 362.4 (M$^+$+1).

Example 23: Synthesis of Compound 23, 1-(2-(4-chloro-2-fluoro-5-methylphenyl)-2-oxoethyl)-4-(5-(difluoromethyl)-1,3,4-oxadiazole-2-yl)pyridine-2(1H)-one

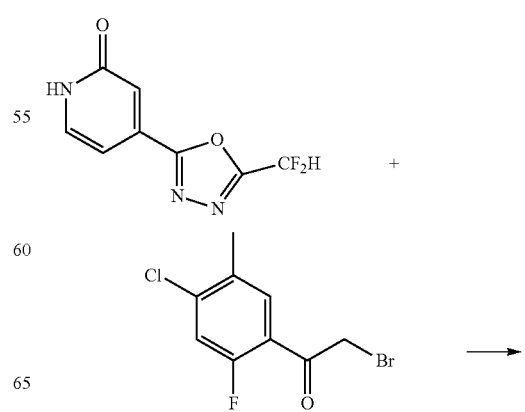

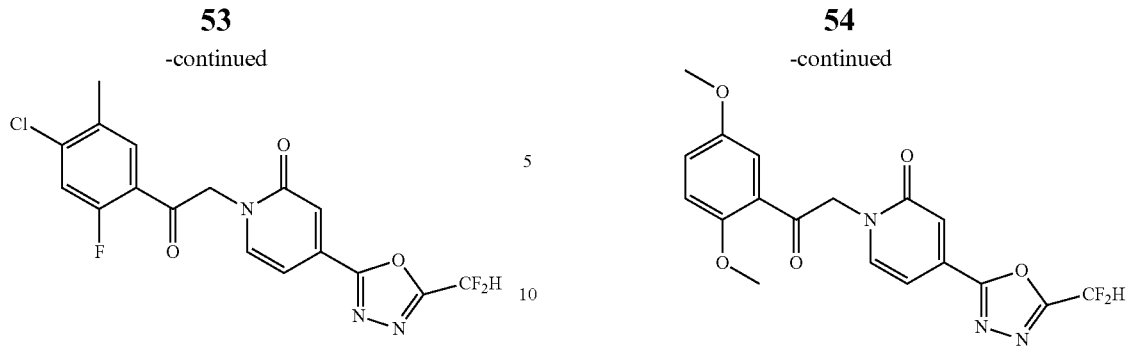

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(4-chloro-2-fluoro-5-methylphenyl)ethane-1-one (0.187 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.110 g, 58.9%) in a white solid form.

$^1$H NMR (400 MHz, CDCl$_3$) δ 7.85 (d, J=7.6 Hz, 1H), 7.42 (dd, J=7.1, 0.5 Hz, 1H), 7.32~7.26 (m, 2H), 7.08 (s, 0.25H), 6.95 (s, 0.5H), 6.94 (dd, J=6.8, 1.6 Hz, 1H), 6.82 (s, 0.25H), 5.31 (s, 2H), 2.39 (s, 3H); LRMS (ES) m/z 398.3 (M$^+$+1).

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(2,5-dimethoxyphenyl)ethane-1-one (0.182 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.130 g, 70.8%) in a white solid form.

$^1$H NMR (400 MHz, CDCl$_3$) δ 7.46 (d, J=3.2 Hz, 1H), 7.42 (d, J=7.1 Hz, 1H), 7.30 (d, J=1.8 Hz, 1H), 7.14 (dd, J=9.1, 3.3 Hz, 1H), 7.07 (s, 0.25H), 6.96 (d, J=11.2 Hz, 1H), 6.94 (s, 0.5H), 6.91 (dd, J=7.0, 1.9 Hz, 1H), 6.82 (s, 0.25H), 5.38 (s, 2H), 3.97 (s, 3H), 3.80 (s, 3H); LRMS (ES) m/z 392.3 (M$^+$+1).

Example 24: Synthesis of Compound 24, 4-(5-(difluoromethyl)-1,3,4-oxadiazole-2-yl)-1-(2-(2,5-dimethoxyphenyl)-2-oxoethyl) pyridine-2(1H)-one Example 25: Synthesis of Compound 25, 4-(5-(difluoromethyl)-1,3,4-oxadiazole-2-yl)-1-(2-(4-nitrophenyl)-2-oxoethyl)pyridine-2(1H)-one

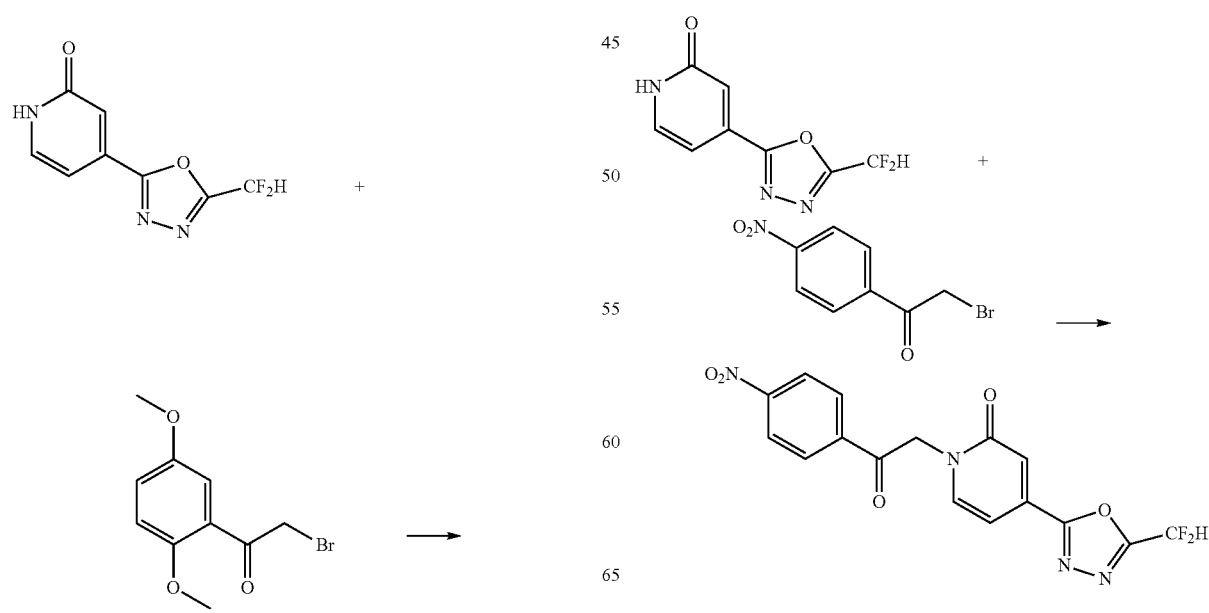

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 2-bromo-1-(4-nitrophenyl)ethane-1-one (0.172 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.080 g, 45.3%) in a white solid form.

$^1$H NMR (400 MHz, CDCl$_3$) δ 8.43~8.32 (m, 2H), 8.28~8.13 (m, 2H), 7.46 (d, J=7.2 Hz, 1H), 7.36 (d, J=1.8 Hz, 1H), 7.09 (s, 0.25H), 7.01 (dd, J=7.1, 1.9 Hz, 1H), 6.96 (s, 0.5H), 6.83 (s, 0.25H), 5.29 (s, 2H); LRMS (ES) m/z 377.3 (M$^+$+1).

Example 26: Synthesis of Compound 26, 4-(5-(difluoromethyl)-1,3,4-oxadiazole-2-yl)-1-(4-nitrobenzyl)pyridine-2(1H)-one

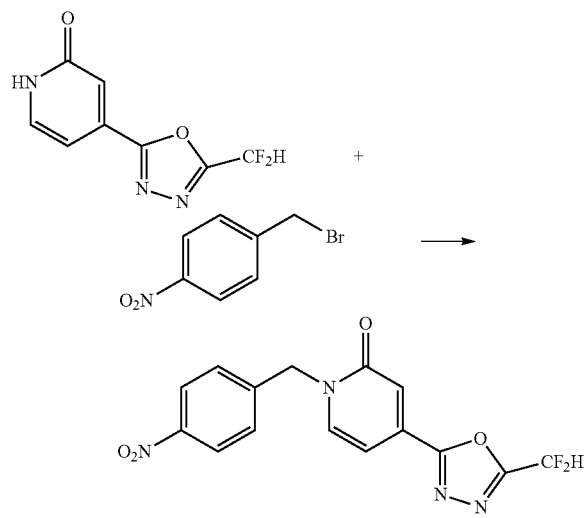

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 1-(bromomethyl)-4-nitrobenzene (0.152 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 61.2%) in a white solid form.

$^1$H NMR (400 MHz, CDCl$_3$) δ 8.28~8.20 (m, 2H), 7.53~7.46 (m, 3H), 7.34~7.28 (m, 1H), 7.07 (s, 0.25H), 6.94 (s, 0.5H), 6.94 (dd, J=7.2, 2.0 Hz, 1H), 6.82 (s, 0.25H), 5.29 (s, 2H); LRMS (ES) m/z 349.3 (M$^+$+1).

Example 27: Synthesis of Compound 27, 4-(5-(difluoromethyl)-1,3,4-oxadiazole-2-yl)-1-(2-ethylbutyl)pyridine-2(1H)-one

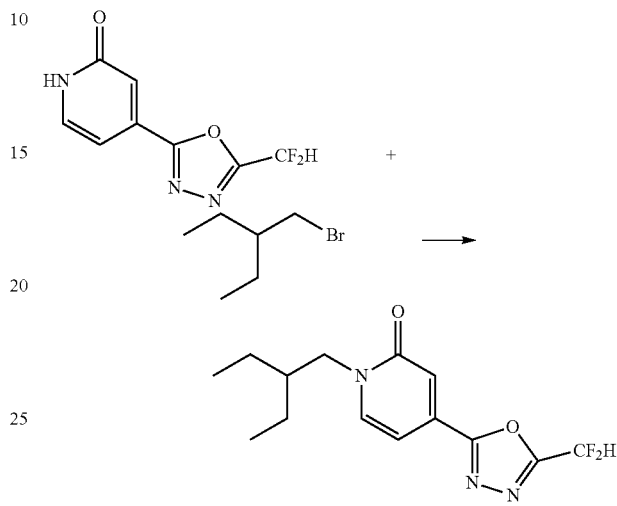

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 3-(bromomethyl)pentane (0.116 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.090 g, 64.5%) in a colorless oil form.

$^1$H NMR (400 MHz, CDCl$_3$) δ 7.42 (dd, J=7.1, 0.6 Hz, 1H), 7.25 (dd, J=1.9, 0.5 Hz, 1H), 7.06 (s, 0.25H), 6.93 (s, 0.5H), 6.84 (dd, J=7.1, 2.0 Hz, 1H), 6.81 (s, 0.25H), 3.90 (d, J=7.4 Hz, 2H), 1.88~1.85 (m, 1H), 1.40~1.33 (m, 4H), 0.93 (t, J=7.4 Hz, 6H); LRMS (ES) m/z 298.4 (M$^+$+1).

Example 28: Synthesis of Compound 28, 4-(5-(difluoromethyl)-1,3,4-oxadiazole-2-yl)-1-((5-(trifluoromethyl)-1,2,4-oxadiazole-3-yl)methyl)pyridine-2(1H)-one

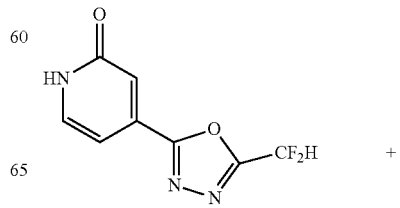

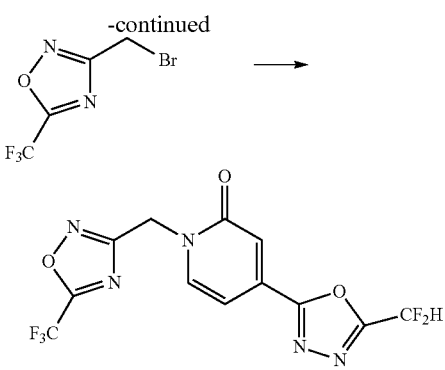

4-(5-(difluoromethyl)-1,3,4-oxadiazole-2-yl)pyridine-2(1H)-one (0.100 g, 0.469 mmol) was dissolved in N,N-dimethylformamide (10 mL) at 0° C., after which hydrogenated sodium (60.00%, 0.028 g, 0.704 mmol) was added into the resulting solution, and stirred at the same temperature for 30 minutes. 3-(bromomethyl)-5-(trifluoromethyl)-1,2,4-oxadiazole (0.163 g, 0.704 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.120 g, 70.4%) in a white solid form.

$^1$H NMR (400 MHz, CDCl$_3$) δ 7.63 (d, J=7.2 Hz, 1H), 7.33 (d, J=1.7 Hz, 1H), 7.07 (s, 0.25H), 6.99 (dd, J=7.2, 1.9 Hz, 1H), 6.94 (s, 0.5H), 6.82 (s, 0.25H), 5.40 (s, 2H); LRMS (ES) m/z 364.3 (M$^+$+1).

Example 29: Synthesis of Compound 29, 2-(4-(4-(5-(difluoromethyl)-1,3,4-oxadiazole-2-yl)-2-oxopyridine-1(2H)-yl)butyl)isoindoline-1,3-dione

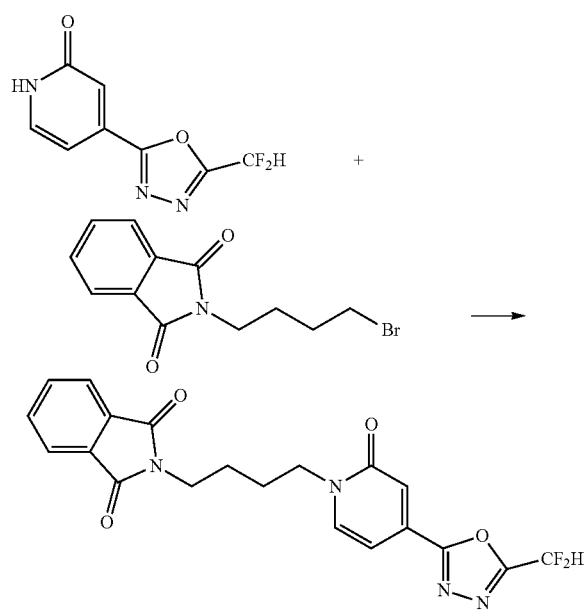

4-(5-(difluoromethyl)-1,3,4-oxadiazole-2-yl)pyridine-2(1H)-one (0.100 g, 0.469 mmol) was dissolved in N,N-dimethylformamide (2.5 mL) at 0° C., after which hydrogenated sodium (60.00%, 0.028 g, 0.704 mmol) was added into the resulting solution, and stirred at the same temperature for 10 minutes. 2-(4-bromobutyl)isoindoline-1,3-dione (0.172 g, 0.610 mmol) was added into the reaction mixture, and further stirred at room temperature for two hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; ethyl acetate/hexane=0 to 100%), and concentrated to obtain the title compound (0.067 g, 34.5%) in a white solid form.

$^1$H NMR (400 MHz, CDCl$_3$) δ 7.84~7.82 (m, 2H), 7.72~7.70 (m, 2H), 7.49 (d, J=7.1 Hz, 1H), 7.22 (d, J=1.8 Hz, 1H), 6.91 (t, J=51.6 Hz, 1H), 6.83 (dd, J=7.1, 1.9 Hz, 1H), 4.04 (t, J=7.1 Hz, 2H), 3.74 (t, J=6.6 Hz, 2H), 1.87~1.75 (m, 4H); LRMS (ES) m/z 415.5 (M$^+$+1).

Example 30: Synthesis of Compound 30, 1-(2,4,5-trifluorobenzyl)-4-(5-(trifluoromethyl)-1,3,4-oxadiazole-2-yl)pyridine-2(1H)one

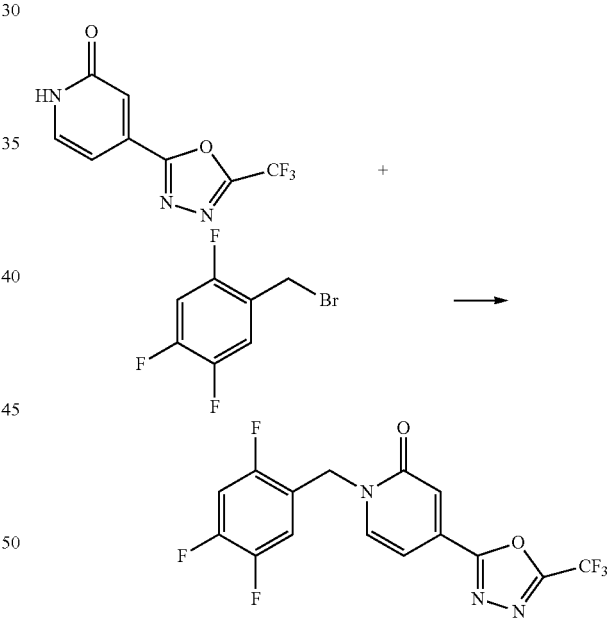

4-(5-(trifluoromethyl)-1,3,4-oxadiazole-2-yl)pyridine-2(1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 1-(bromomethyl)-2,4,5-trifluorobenzene (0.127 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO₂, 12 g cartridge; hexane/ethyl acetate=0 to 100%), and concentrated to obtain the title compound (0.029 g, 17.9%) in a white solid form.

¹H NMR (400 MHz, CDCl₃) δ 7.61 (dd, J=7.2, 0.7 Hz, 1H), 7.46~7.40 (m, 1H), 7.27~7.26 (m, 1H), 6.98 (td, J=9.6, 6.4 Hz, 1H), 6.88 (dd, J=7.1, 1.9 Hz, 1H), 5.13 (s, 2H); LRMS (ES) m/z 376.4 (M⁺+1).

Example 31: Synthesis of Compound 31, 1-(3-fluorobenzyl)-4-(5-(trifluoromethyl)-1,3,4-oxadiazole-2-yl)pyridine-2(1H)-one

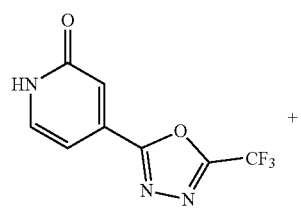

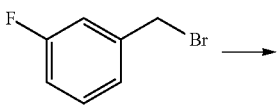

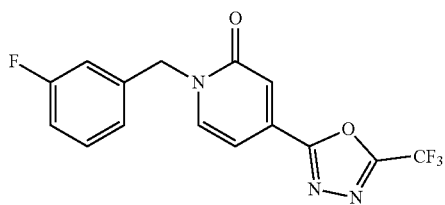

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 1-(bromomethyl)-3-fluorobenzene (0.106 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO₂, 12 g cartridge; hexane/ethyl acetate=0 to 100%), and concentrated to obtain the title compound (0.041 g, 27.9%) in a white solid form.

¹H NMR (400 MHz, CDCl₃) δ 7.48 (dd, J=7.1, 0.5 Hz, 1H), 7.36~7.30 (m, 2H), 7.11~7.09 (m, 1H), 7.02~7.00 (m, 2H), 6.85 (dd, J=7.1, 1.9 Hz, 1H), 5.17 (s, 2H); LRMS (ES) m/z 340.4 (M⁺+1).

Example 32: Synthesis of Compound 32, 1-(2-fluorobenzyl)-4-(5-(trifluoromethyl)-1,3,4-oxadiazole-2-yl)pyridine-2(1H)-one

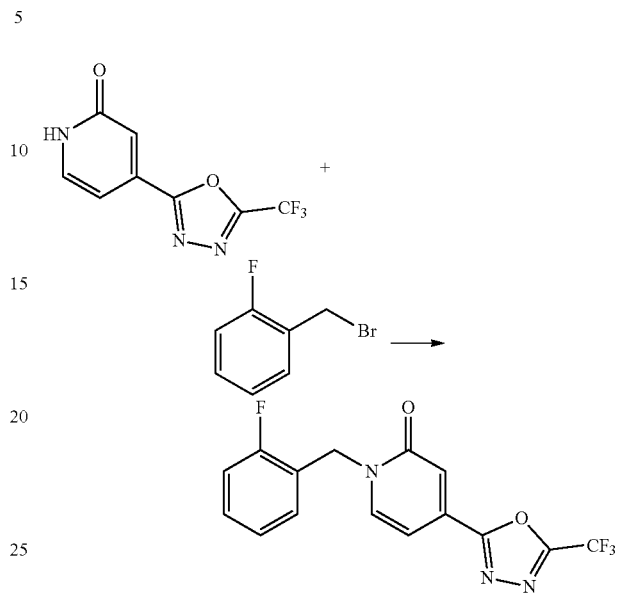

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 1-(bromomethyl)-2-fluorobenzene (0.106 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO₂, 12 g cartridge; hexane/ethyl acetate=0 to 100%), and concentrated to obtain the title compound (0.047 g, 32.0%) in a white solid form.

¹H NMR (400 MHz, CDCl₃) δ 7.60 (d, J=7.0 Hz, 1H), 7.48 (td, J=7.6, 1.7 Hz, 1H), 7.35~7.29 (m, 1H), 7.25 (d, J=1.6 Hz, 1H), 7.16~7.06 (m, 2H), 6.83 (dd, J=7.2, 2.0 Hz, 1H), 5.20 (s, 2H); LRMS (ES) m/z 340.3 (M⁺+1).

Example 33: Synthesis of Compound 33, 1-(2,5-difluorobenzyl)-4-(5-(trifluoromethyl)-1,3,4-oxadiazole-2-yl)pyridine-2(1H)-one

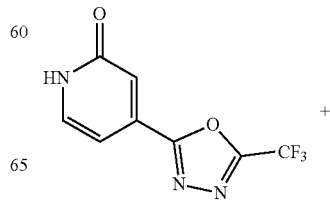

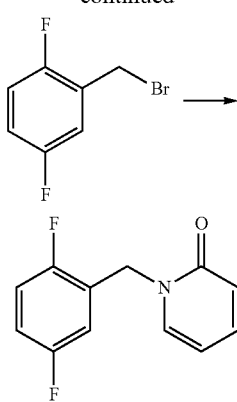

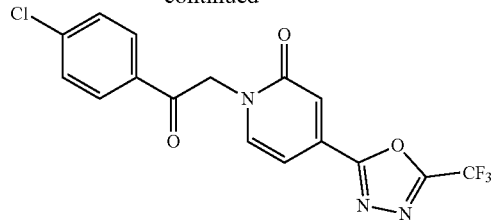

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 2-(bromomethyl)-1,4-difluorobenzene (0.116 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.050 g, 32.3%) in a white solid form.

$^1$H NMR (400 MHz, CDCl$_3$) δ 7.61 (d, J=7.2 Hz, 1H), 7.26~7.26 (m, 1H), 7.21~7.17 (m, 1H), 7.09~6.87 (m, 2H), 6.86 (dd, J=7.1, 2.0 Hz, 1H), 5.17 (d, J=0.9 Hz, 2H); LRMS (ES) m/z 358.3 (M$^+$+1).

Example 34: Synthesis of Compound 34, 1-(2-(4-chlorophenyl)-2-oxoethyl)-4-(5-(trifluoromethyl)-1,3,4-oxadiazole-2-yl)pyridine-2(1H)-one

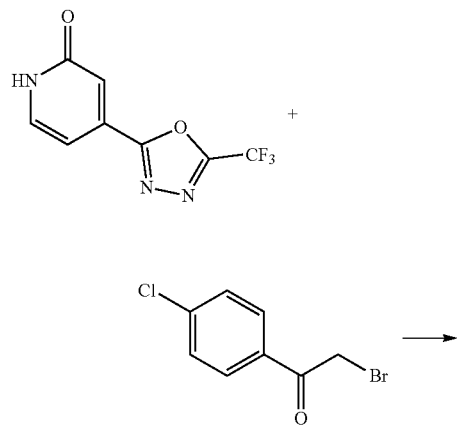

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 2-bromo-1-(4-chlorophenyl)ethane-1-one (0.131 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.088 g, 53.0%) in a yellow solid form.

$^1$H NMR (400 MHz, CDCl$_3$) δ 7.98 (d, J=8.6 Hz, 2H), 7.52 (d, J=8.6 Hz, 2H), 7.42 (d, J=7.1 Hz, 1H), 7.31 (d, J=1.7 Hz, 1H), 6.94 (dd, J=7.1, 1.9 Hz, 1H), 5.39 (s, 2H); LRMS (ES) m/z 384.3 (M$^+$+1).

Example 35: Synthesis of Compound 35, 1-(2-(4-(methylsulfonyl)phenyl)-2-oxoethyl)-4-(5-(trifluoromethyl)-1,3,4-oxadiazole-2-yl)pyridine-2(1H)-one

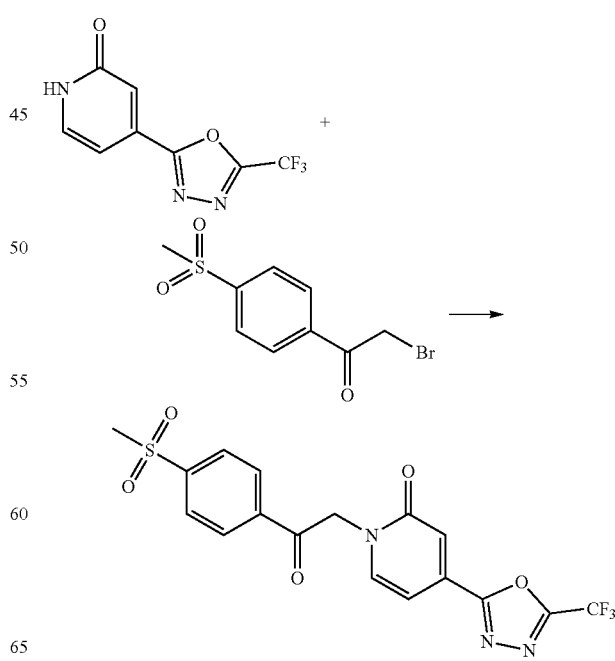

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 2-bromo-1-(4-(methylsulfonyl)phenyl)ethane-1-one (0.156 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.084 g, 45.4%) in a yellow solid form.

$^1$H NMR (400 MHz, CDCl$_3$) δ 8.22 (d, J=8.4 Hz, 2H), 8.12 (d, J=8.4 Hz, 2H), 7.46 (d, J=7.1 Hz, 1H), 7.32 (d, J=1.9 Hz, 1H), 6.97 (dd, J=7.1, 1.9 Hz, 1H), 5.41 (s, 2H), 3.11 (s, 3H); LRMS (ES) m/z 428.3 (M$^+$+1).

Example 36: Synthesis of Compound 36, 1-(2-oxo-2-(thiophene-2-yl)ethyl)-4-(5-(trifluoromethyl)-1,3,4-oxadiazole-2-yl)pyridine-2(1H)-one

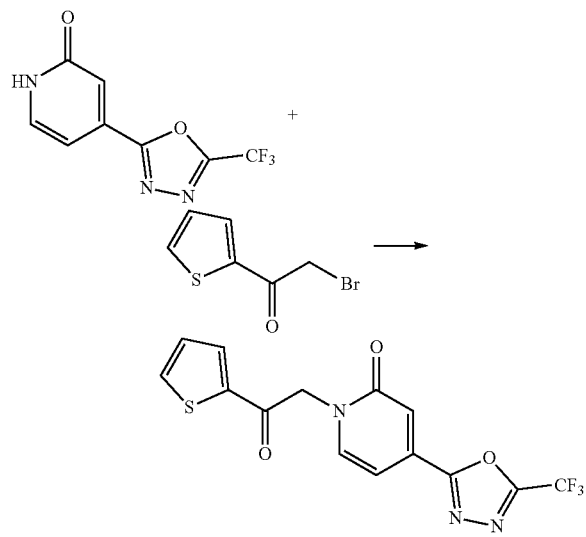

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 2-bromo-1-(thiophene-2-yl)ethane-1-one (0.115 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.118 g, 76.8%) in a brown solid form.

$^1$H NMR (400 MHz, CDCl$_3$) δ 7.91 (dd, J=3.8, 1.0 Hz, 1H), 7.75 (dd, J=5.0, 1.0 Hz, 1H), 7.47 (d, J=7.1 Hz, 1H), 7.27~7.26 (m, 1H), 7.20 (dd, J=4.9, 3.9 Hz, 1H), 6.89 (dd, J=7.1, 1.9 Hz, 1H), 5.34 (s, 2H); LRMS (ES) m/z 356.3 (M$^+$+1).

Example 37: Synthesis of Compound 37, 1-(2-(5-chlorothiophene-2-yl)-2-oxoethyl)-4-(5-(trifluoromethyl)-1,3,4-oxadiazole-2-yl)pyridine-2(1H)-one

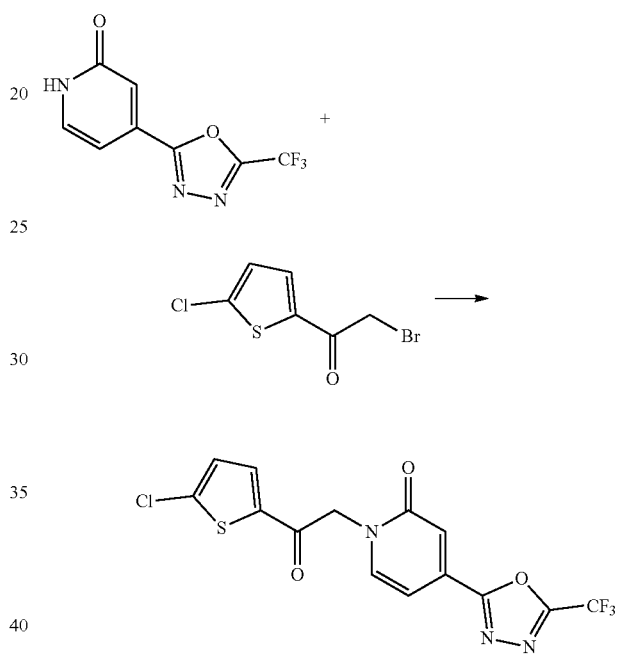

4-(5-(trifluoromethyl)-1,3,4-oxadiazole-2-yl)pyridine-2 (1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 2-bromo-1-(5-chlorothiophene-2-yl)ethane-1-one (0.135 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.088 g, 52.2%) in a brown solid form.

$^1$H NMR (400 MHz, CDCl$_3$) δ 7.73 (d, J=4.1 Hz, 1H), 7.46 (d, J=7.2 Hz, 1H), 7.29 (d, J=1.6 Hz, 1H), 7.04 (d, J=4.1 Hz, 1H), 6.92 (dd, J=7.1, 1.9 Hz, 1H), 5.26 (s, 2H); LRMS (ES) m/z 390.3 (M$^+$+1).

Example 38: Synthesis of Compound 38, 1-(2-(benzofuran-3-yl)-2-oxoethyl)-4-(5-(trifluoromethyl)-1,3,4-oxadiazole-2-yl)pyridine-2(1H)-one

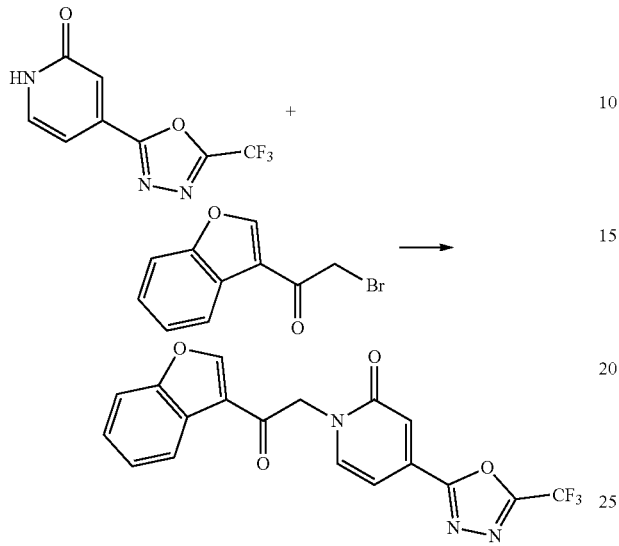

4-(5-(trifluoromethyl)-1,3,4-oxadiazole-2-yl)pyridine-2(1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 1-(benzofuran-3-yl)-2-bromoethane-1-one (0.134 g, 0.562 mmol) was added into the reaction mixture, and further stirred at room temperature for 18 hours. Solvent was removed from the reaction mixture under reduced pressure, after which water was poured into a resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 12 g cartridge; hexane/ethyl acetate=0 to 100%), and concentrated to obtain the title compound (0.074 g, 43.9%) in a brown solid form.
$^1$H NMR (400 MHz, CDCl$_3$) δ 8.54 (s, 1H), 8.16 (dd, J=7.5, 1.4 Hz, 1H), 7.57 (dd, J=7.1, 1.6 Hz, 1H), 7.53 (d, J=7.1 Hz, 1H), 7.44~7.36 (m, 2H), 7.31 (d, J=1.8 Hz, 1H), 6.95 (dd, J=7.1, 1.9 Hz, 1H), 5.27 (s, 2H); LRMS (ES) m/z 390.4 (M$^+$+1).

Example 39: Synthesis of Compound 39, 2-(2-oxo-4-(5-(trifluoromethyl)-1,3,4-oxadiazole-2-yl)pyridine-1(2H)-yl)ethyl benzoate

[Step 1] Synthesis of 4-(5-(trifluoromethyl)-1,3,4-oxadiazole-2-yl)pyridine-2(1H)-one

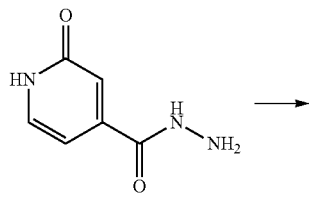

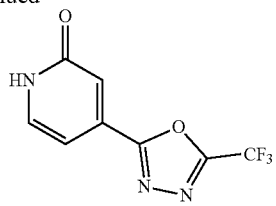

2-oxo-1,2-dihydropyridine-4-carbohydrazide (10.000 g, 65.300 mmol), trifluoroacetic anhydride (27.670 mL, 195.899 mmol) and imidazole (13.336 g, 195.899 mmol) were dissolved in dichloromethane (50 mL) at 45° C., after which the resulting solution was stirred at the same temperature for 12 hours, and then a reaction was finished by lowering the temperature to room temperature. Water (20 mL) was put into the reaction mixture and stirred, after which a precipitated solid was filtered, then washed with water, and then dried to obtain the title compound (6.500 g, 43.1%) in a white solid form.

[Step 2] Synthesis of Compound 39

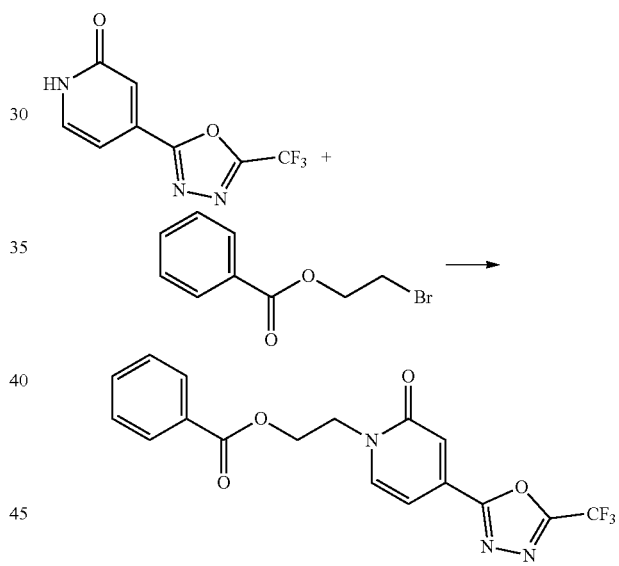

The 4-(5-(trifluoromethyl)-1,3,4-oxadiazole-2-yl)pyridine-2(1H)-one (0.100 g, 0.433 mmol) prepared in the step 1 was dissolved in N,N-dimethylformamide (10 mL) at 0° C., after which hydrogenated sodium (60.00%, 0.026 g, 0.649 mmol) was added into the resulting solution, and stirred at the same temperature for 30 minutes. 2-bromoethyl benzoate (0.149 g, 0.649 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.050 g, 30.5%) in a white solid form.
$^1$H NMR (400 MHz, CDCl$_3$) δ 8.05~7.97 (m, 1H), 7.78~7.60 (m, 1H), 7.59~7.45 (m, 4H), 7.30~7.28 (m, 1H), 6.87 (dd, J=7.1, 1.9 Hz, 1H), 4.72~4.70 (m, 2H), 4.41~4.39 (m, 2H); LRMS (ES) m/z 380.4 (M⁺+1).

Example 40: Synthesis of Compound 40, benzyl 2-(2-oxo-4-(5-(trifluoromethyl)-1,3,4-oxadiazole-2-yl)pyridine-1(2H)-yl)acetate

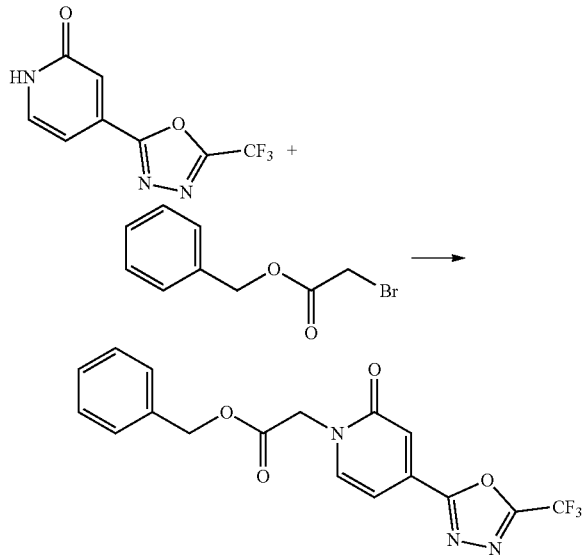

4-(5-(trifluoromethyl)-1,3,4-oxadiazole-2-yl)pyridine-2(1H)-one (0.100 g, 0.433 mmol) was dissolved in N,N-dimethylformamide (10 mL) at 0° C., after which hydrogenated sodium (60.00%, 0.026 g, 0.649 mmol) was added into the resulting solution and stirred at the same temperature for 30 minutes. Benzyl 2-bromoacetate (0.149 g, 0.649 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.110 g, 67.0%) in a yellow solid form.

¹H NMR (400 MHz, CDCl₃) δ 7.45 (dd, J=7.1, 0.5 Hz, 1H), 7.41~7.32 (m, 5H), 7.29~7.28 (m, 1H), 6.90 (dd, J=7.1, 1.9 Hz, 1H), 5.22 (s, 2H), 4.76 (s, 2H); LRMS (ES) m/z 380.4 (M⁺+1).

Example 41: Synthesis of Compound 41, 1-(2-(naphthalene-2-yl)-2-oxoethyl)-4-(5-(trifluoromethyl)-1,3,4-oxadiazole-2-yl)pyridine-2(1H)-one

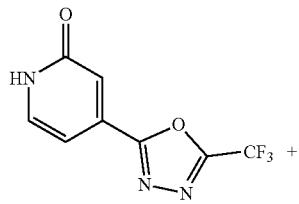

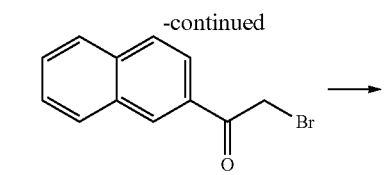

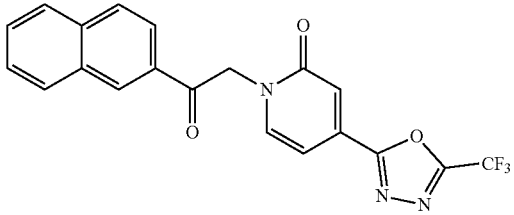

4-(5-(trifluoromethyl)-1,3,4-oxadiazole-2-yl)pyridine-2(1H)-one (0.100 g, 0.433 mmol) was dissolved in N,N-dimethylformamide (10 mL) at 0° C., after which hydrogenated sodium (60.00%, 0.026 g, 0.649 mmol) was added into the resulting solution, and stirred at the same temperature for 30 minutes. 2-bromo-1-(naphthalene-2-yl)ethane-1-one (0.162 g, 0.649 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO₂, 12 g cartridge; ethyl acetate/hexane=0 to 50%), and concentrated to obtain the title compound (0.120 g, 69.5%) in a yellow solid form.

¹H NMR (400 MHz, CDCl₃) δ 8.61 (s, 1H), 8.08~7.85 (m, 4H), 7.70~7.59 (m, 2H), 7.50 (d, J=7.1 Hz, 1H), 7.35 (d, J=1.7 Hz, 1H), 6.97 (dd, J=7.1, 1.9 Hz, 1H), 5.61 (s, 2H); LRMS (ES) m/z 400.4 (M⁺+1).

Example 42: Synthesis of Compound 42, 1-(2-oxo-2-phenylethyl)-4-(5-(trifluoromethyl)-1,3,4-oxadiazole-2-yl)pyridine-2(1H)-one

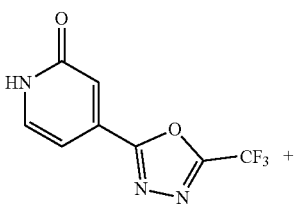

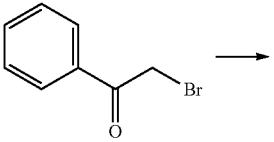

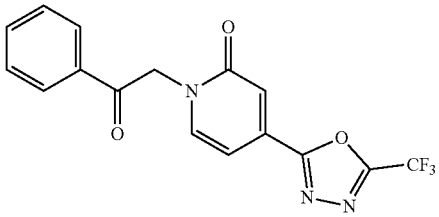

4-(5-(trifluoromethyl)-1,3,4-oxadiazole-2-yl)pyridine-2(1H)-one (0.100 g, 0.433 mmol) was dissolved in N,N-dimethylformamide (10 mL) at 0° C., after which hydrogenated sodium (60.00%, 0.026 g, 0.649 mmol) was added into the resulting solution, and stirred at the same temperature for 30 minutes. 2-bromo-1-phenylethane-1-one (0.129 g, 0.649 mmol) was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (0.100 g, 66.2%) in a white solid form.

$^1$H NMR (400 MHz, CDCl$_3$) δ 8.05~8.03 (m, 2H), 7.70~7.65 (m, 1H), 7.57~7.52 (m, 2H), 7.45 (dd, J=7.1, 0.7 Hz, 1H), 7.32 (dd, J=1.9, 0.6 Hz, 1H), 6.94 (dd, J=7.1, 1.9 Hz, 1H), 5.46 (s, 2H); LRMS (ES) m/z 350.3 (M$^+$+1).

Example 43: Synthesis of Compound 43, tert-butyl 2-(4-(5-(difluoromethyl)-1,3,4-oxadiazole-2-yl)-2-oxopyridine-1(2H)-yl)acetate

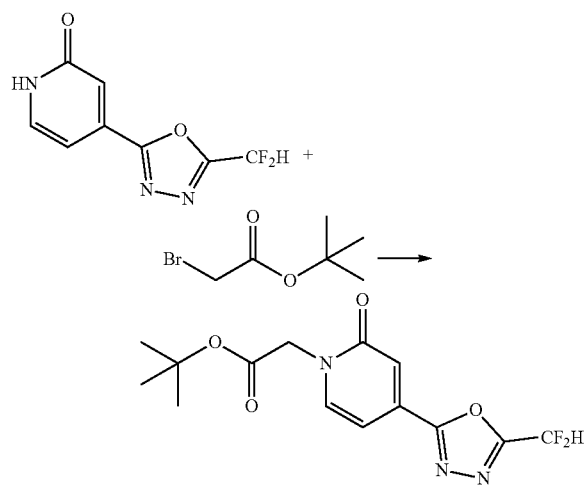

4-(5-(difluoromethyl)-1,3,4-oxadiazole-2-yl)pyridine-2(1H)-one (1.000 g, 4.692 mmol) was dissolved in N,N-dimethylformamide (30 mL) at 0° C., after which hydrogenated sodium (60.00%, 0.281 g, 7.038 mmol) was added into the resulting solution, and stirred at the same temperature for 30 hours. Tert-butyl 2-bromoacetate (1.007 g, 5.161 mmol) was added into the reaction mixture, and further stirred at room temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 50%), and concentrated to obtain the title compound (1.300 g, 84.7%) in a colorless oil form.

$^1$H NMR (400 MHz, CDCl$_3$) δ 7.42 (dd, J=7.2, 0.6 Hz, 1H), 7.31~7.30 (m, 1H), 7.07 (s, 0.25H), 6.94 (s, 0.5H), 6.91 (dd, J=7.1, 1.9 Hz, 1H), 6.81 (s, 0.25H), 4.62 (s, 2H), 1.51 (s, 9H); LRMS (ES) m/z 328.4 (M$^+$+1).

Example 44: Synthesis of Compound 44, 4-(5-(difluoromethyl)-1,3,4-oxadiazole-2-yl)-1-(3-morpholino-3-oxo-2-phenylpropyl)pyridine-2(1H)-one

[Step 1] Synthesis of benzyl 2-phenylacetate

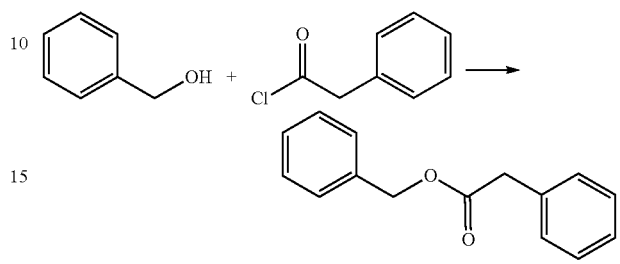

Phenylmethanol (3.000 g, 27.742 mmol), 2-phenylacetyl chloride (4.289 g, 27.742 mmol) and triethylamine (4.253 mL, 30.516 mmol) were dissolved in dichloromethane (50 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography (SiO$_2$, 40 g cartridge; ethyl acetate/hexane=0 to 10%), and concentrated to obtain a title compound (4.400 g, 70.1%) in a colorless oil form.

[Step 2] Synthesis of benzyl 3-hydroxy-2-phenylpropanoate

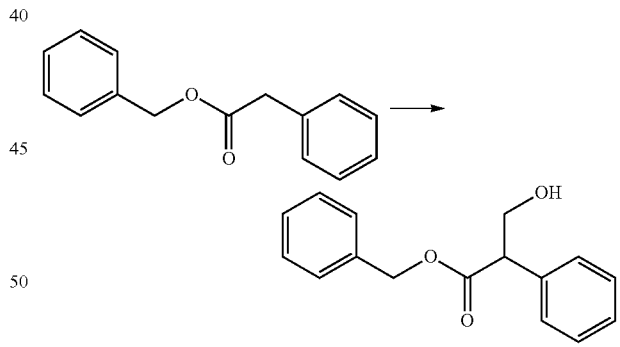

The benzyl 2-phenylacetate (5.300 g, 23.422 mmol) prepared in the step 1, formaldehyde (0.774 g, 25.765 mmol) and potassium carbonate (3.561 g, 25.765 mmol) were dissolved in N,N-dimethylformamide (30 mL) at room temperature, after which the resulting solution was stirred at the same temperature for 12 hours. Saturated ammonium chloride aqueous solution was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 40 g cartridge; ethyl acetate/hexane=0 to 30%), and concentrated to obtain the title compound (3.400 g, 56.6%) in a colorless oil form.

[Step 3] Synthesis of benzyl 3-bromo-2-phenylpropanoate

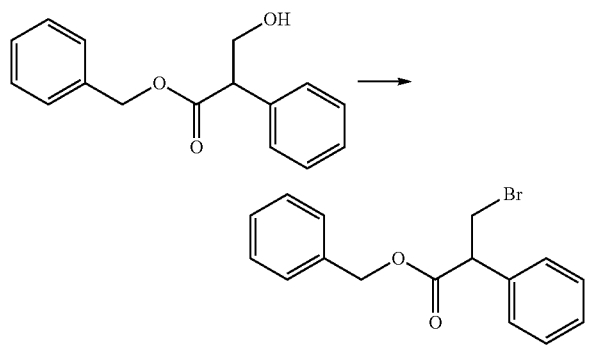

The benzyl 3-hydroxy-2-phenylpropanoate (2.000 g, 7.803 mmol) prepared in the step 2, carbon tetrabromide (3.364 g, 10.144 mmol) and triphenylphosphine (2.661 g, 10.144 mmol) were dissolved in dichloromethane (30 mL) at room temperature, after which the resulting solution was stirred at the same temperature for two hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography (SiO$_2$, 40 g cartridge; ethyl acetate/hexane=0 to 10%), and concentrated to obtain the title compound (2.000 g, 80.3%) in a colorless oil form.

[Step 4] Synthesis of benzyl 3-(4-(5-(difluoromethyl)-1,3,4-oxadiazole-2-yl)-2-oxopyridine-1(2H)-yl)-2-phenylpropanoate

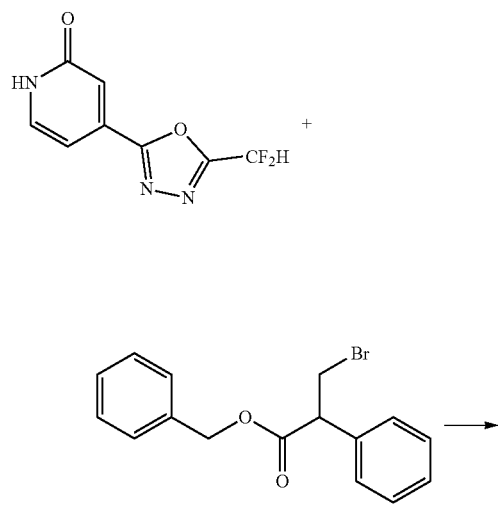

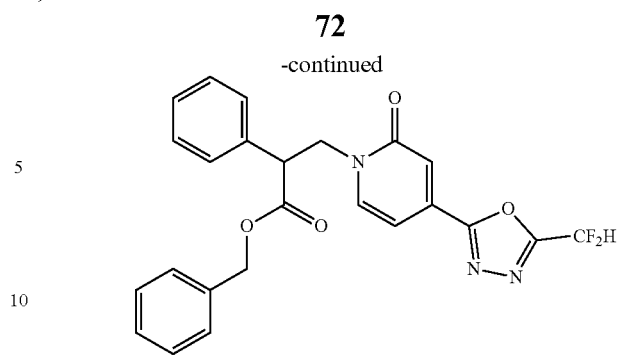

4-(5-(difluoromethyl)-1,3,4-oxadiazole-2-yl)pyridine-2 (1H)-one (1.100 g, 5.161 mmol) was dissolved in N,N-dimethylformamide (20 mL) at 0° C., after which hydrogenated sodium (60.00%, 0.310 g, 7.741 mmol) was added into the resulting solution, and stirred at the same temperature for 30 minutes. The benzyl 3-bromo-2-phenylpropanoate (1.977 g, 6.193 mmol) prepared in the step 3 was added into the reaction mixture, and further stirred at room temperature for three hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. A concentrate was purified via column chromatography (SiO$_2$, 40 g cartridge; ethyl acetate/hexane=0 to 50%), and concentrated to obtain the title compound (0.500 g, 21.5%) in a colorless oil form.

[Step 5] Synthesis of 3-(4-(5-(difluoromethyl)-1,3,4-oxadiazole-2-yl)-2-oxopyridine-1(2H)-yl)-2-phenylpropanoic acid

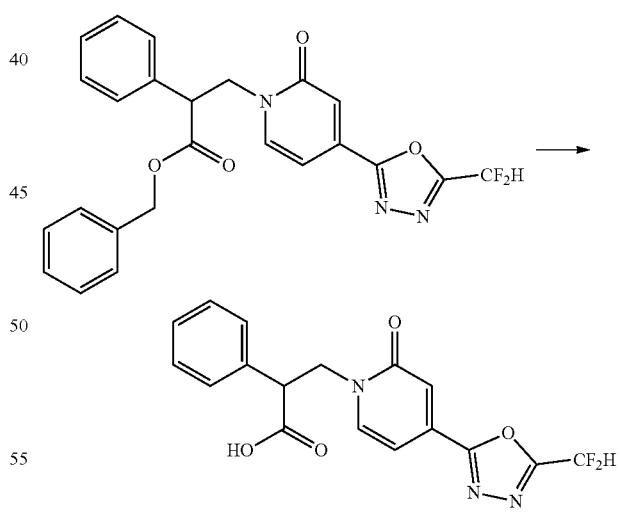

The benzyl 3-(4-(5-(difluoromethyl)-1,3,4-oxadiazole-2-yl)-2-oxopyridine-1(2H)-yl)-2-phenylpropanoate (0.500 g, 1.108 mmol) prepared in the step 4 was dissolved in methanol (10 mL) at room temperature, after which 10%-Pd/C (0.05 mg) was slowly added thereinto, and stirred at the same temperature for 12 hours in the presence of a hydrogen balloon attached thereto. The reaction mixture was filtered via a celite pad to remove a solid therefrom, after which solvent was removed from a resulting filtrate under

[Step 6] Synthesis of Compound 44

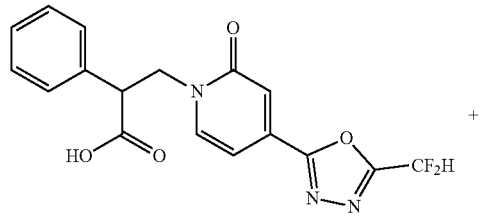

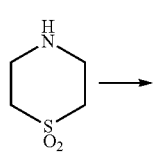

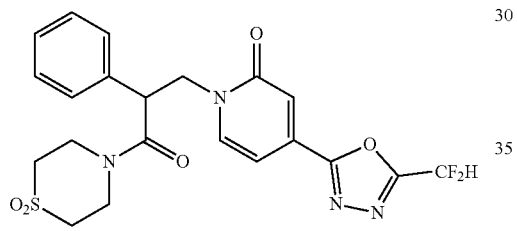

The 3-(4-(5-(difluoromethyl)-1,3,4-oxadiazole-2-yl)-2-oxopyridine-1(2H)-yl)-2-phenylpropanoic acid (0.290 g, 0.803 mmol) prepared in the step 5, thiomorpholine 1,1-dioxide (0.163 g, 1.204 mmol), 1H-benzo[d][1,2,3]triazole-1-ol (HOBt, 0.217 g, 1.605 mmol), 1-ethyl-3-(3-dimethylaminopropyl)carbodiimide hydrochloride (EDC-HCl, 0.308 g, 1.605 mmol) and N,N-diisopropylethylamine (0.559 mL, 3.211 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 70%), and concentrated to obtain the title compound (0.200 g, 52.1%) in a white solid form.

$^1$H NMR (400 MHz, CDCl$_3$) δ 7.42~7.37 (m, 4H), 7.30~7.28 (m, 2H), 7.25 (d, J=1.8 Hz, 1H), 7.06 (s, 0.25H), 6.94 (s, 0.5H), 6.81 (s, 0.25H), 6.69 (dd, J=7.1, 1.9 Hz, 1H), 4.67~4.64 (m, 1H), 4.56~4.47 (m, 2H), 4.20 (dd, J=12.8, 5.9 Hz, 1H), 3.89~3.80 (m, 1H), 3.70~3.61 (m, 2H), 2.96~2.87 (m, 2H), 2.64~2.59 (m, 1H), 2.01~1.93 (m, 1H); LRMS (ES) m/z 479.4 (M$^+$+1).

Example 45: Synthesis of Compound 45, 4-(5-(difluoromethyl)-1,3,4-oxadiazole-2-yl)-1-(3-morpholino-3-oxo-2-phenylpropyl)pyridine-2(1H)-one

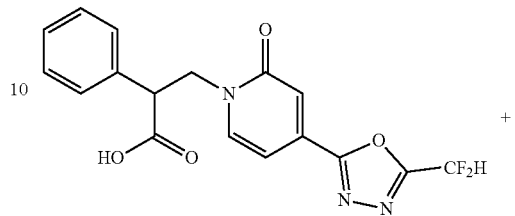

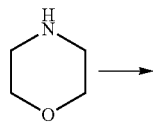

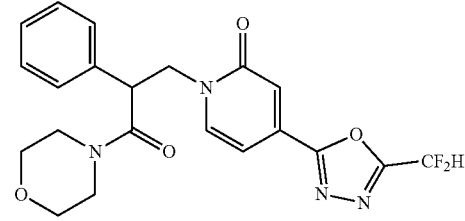

3-(4-(5-(difluoromethyl)-1,3,4-oxadiazole-2-yl)-2-oxopyridine-1(2H)-yl)-2-phenylpropanoic acid (0.290 g, 0.803 mmol), morpholine (0.104 mL, 1.204 mmol), 1H-benzo[d][1,2,3]triazole-1-ol (HOBt, 0.217 g, 1.605 mmol), 1-ethyl-3-(3-dimethylaminopropyl)carbodiimide hydrochloride (EDC-HCl, 0.308 g, 1.605 mmol) and N,N-diisopropylethylamine (0.559 mL, 3.211 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 70%), and concentrated to obtain the title compound (0.080 g, 23.2%) in a colorless oil form.

$^1$H NMR (400 MHz, CDCl$_3$) δ 7.47 (dd, J=7.1, 0.5 Hz, 1H), 7.39~7.30 (m, 5H), 7.26 (dd, J=1.9, 0.5 Hz, 1H), 7.07 (s, 0.25H), 6.94 (s, 0.5H), 6.80 (s, 0.25H), 6.70 (dd, J=7.1, 2.0 Hz, 1H), 4.57~4.48 (m, 2H), 4.24 (dd, J=11.6, 4.5 Hz, 1H), 3.80~3.75 (m, 1H), 3.62~3.61 (m, 1H), 3.54~3.42 (m, 3H), 3.40~3.30 (m, 1H), 3.22~3.20 (m, 1H), 3.06~3.03 (m, 1H); LRMS (ES) m/z 431.4 (M$^+$+1).

Example 46: Synthesis of Compound 46, 4-(5-(difluoromethyl)-1,3,4-oxadiazole-2-yl)-1-(2-morpholino-2-oxoethyl)pyridine-2(1H)-one

[Step 1] Synthesis of 2-(4-(5-(difluoromethyl)-1,3,4-oxadiazole-2-yl)-2-oxopyridine-1(2H)-yl)acetic acid

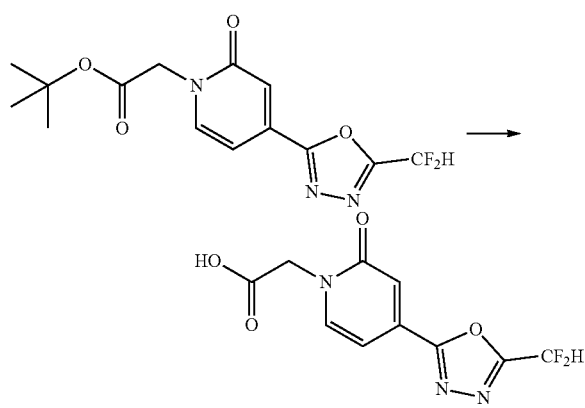

Tert-butyl 2-(4-(5-(difluoromethyl)-1,3,4-oxadiazole-2-yl)-2-oxopyridine-1(2H)-yl)acetate (1.300 g, 3.972 mmol) and trifluoroacetic acid (6.083 mL, 79.440 mmol) were dissolved in dichloromethane (30 mL) at room temperature, after which the resulting solution was stirred at the same temperature for 12 hours. Solvent was removed from the reaction mixture under reduced pressure, after which a product obtained was used without an additional purification process (title compound, 1.000 g, 92.8%, colorless oil).

[Step 2] Synthesis of Compound 46

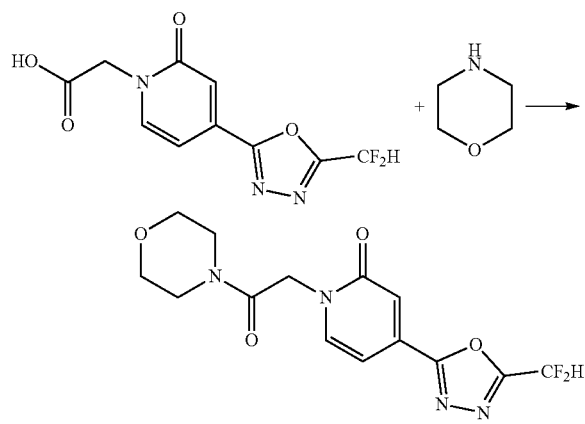

The 2-(4-(5-(difluoromethyl)-1,3,4-oxadiazole-2-yl)-2-oxopyridine-1(2H)-yl)acetic acid (0.160 g, 0.590 mmol) prepared in the step 1, morpholine (0.077 mL, 0.885 mmol), 1H-benzo[d][1,2,3]triazole-1-ol (HOBt, 0.159 g, 1.180 mmol), 1-ethyl-3-(3-dimethylaminopropyl)carbodiimide hydrochloride (EDC-HCl, 0.226 g, 1.180 mmol) and N,N-diisopropylethylamine (0.411 mL, 2.360 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A concentrate was purified via column chromatography (SiO$_2$, 12 g cartridge; ethyl acetate/hexane=0 to 70%), and concentrated to obtain the title compound (0.100 g, 49.8%) in a colorless oil form.

$^1$H NMR (400 MHz, CDCl$_3$) δ 7.51 (dd, J=7.1, 0.7 Hz, 1H), 7.28~7.26 (m, 1H), 7.07 (s, 0.25H), 6.94 (s, 0.5H), 6.91 (dd, J=7.1, 2.0 Hz, 1H), 6.81 (s, 0.25H), 4.80 (s, 2H), 3.78~3.70 (m, 4H), 3.66~3.62 (m, 4H); LRMS (ES) m/z 341.3 (M$^+$+1).

Example 47: Synthesis of Compound 47, 1-(2-methylallyl)-4-(5-(trifluoromethyl)-1,3,4-oxadiazole-2-yl)pyridine-2(1H)-one

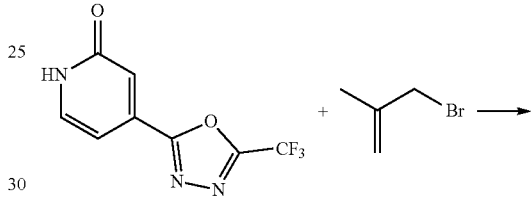

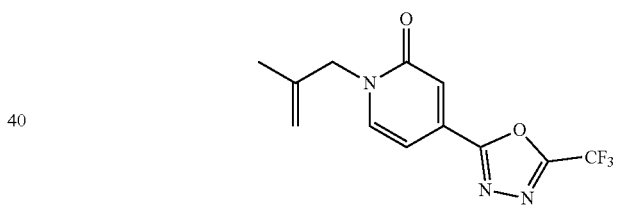

4-(5-(trifluoromethyl)-1,3,4-oxadiazole-2-yl)pyridine-2(1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 3-bromo-2-methylprop-1-en (0.076 g, 0.562 mmol) was added into the reaction mixture, and further stirred at room temperature for 18 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; hexane/ethyl acetate=0 to 100%), and concentrated to obtain the title compound (0.071 g, 57.5%) in a white solid form.

$^1$H NMR (400 MHz, CDCl$_3$) δ 7.43 (d, J=7.1 Hz, 1H), 7.28 (d, J=1.9 Hz, 1H), 6.86 (dd, J=7.1, 2.0 Hz, 1H), 5.02 (s, 1H), 4.80 (s, 1H), 4.56 (s, 2H), 1.76 (s, 3H); LRMS (ES) m/z 286.3 (M$^+$+1).

Example 48: Synthesis of Compound 48, 1-(3-methylbut-2-en-1-yl)-4-(5-(trifluoromethyl)-1,3,4-oxadiazole-2-yl)pyridine-2(1H)-one

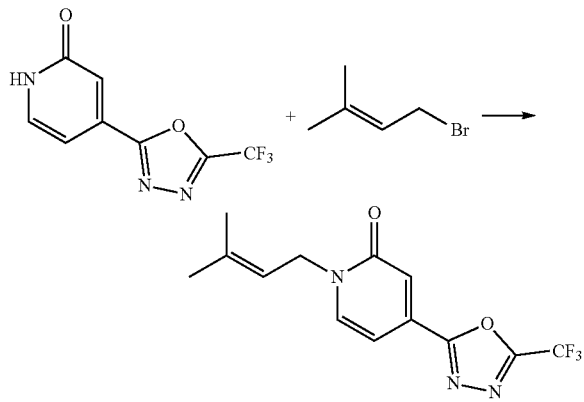

4-(5-(trifluoromethyl)-1,3,4-oxadiazole-2-yl)pyridine-2(1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. 1-bromo-3-methylbut-2-en (0.084 g, 0.562 mmol) was added into the reaction mixture, and further stirred at room temperature for 18 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; hexane/ethyl acetate=0 to 100%), and concentrated to obtain the title compound (0.090 g, 69.5%) in a white solid form.

$^1$H NMR (400 MHz, CDCl$_3$) δ 7.49 (dd, J=7.1, 0.5 Hz, 1H), 7.23 (dd, J=2.0, 0.5 Hz, 1H), 6.83 (dd, J=7.1, 2.0 Hz, 1H), 5.33~5.28 (m, 1H), 4.58 (d, J=7.3 Hz, 2H), 1.80 (dd, J=3.6, 0.8 Hz, 6H); LRMS (ES) m/z 300.3 (M$^+$+1).

Example 49: Synthesis of Compound 49, 1-ethyl-4-(5-(trifluoromethyl)-1,3,4-oxadiazole-2-yl)pyridine-2(1H)-one

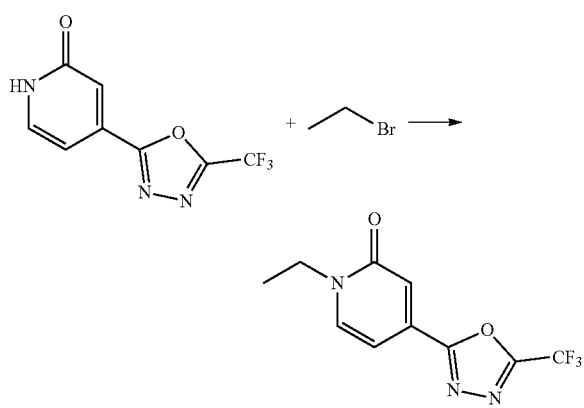

4-(5-(trifluoromethyl)-1,3,4-oxadiazole-2-yl)pyridine-2(1H)-one (0.100 g, 0.433 mmol) was dissolved in N,N-dimethylformamide (2.5 mL), after which hydrogenated sodium (60.00%, 0.026 g, 0.649 mmol) was added into the resulting solution at 0° C., and stirred at the same temperature for 10 minutes. Bromoethane (0.061 g, 0.562 mmol) was added into the reaction mixture, and further stirred at room temperature for 18 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; hexane/ethyl acetate=0 to 100%), and concentrated to obtain the title compound (0.022 g, 19.6%) in a white solid form.

$^1$H NMR (400 MHz, CDCl$_3$) δ 7.49 (d, J=6.8 Hz, 1H), 7.24 (d, J=1.6 Hz, 1H), 6.86 (dd, J=7.1, 1.9 Hz, 1H), 4.05 (q, J=7.2 Hz, 2H), 1.40 (t, J=7.2 Hz, 3H); LRMS (ES) m/z 260.2 (M$^+$+1).

Example 50: Synthesis of Compound 50, 4-(5-(difluoromethyl)-1,3,4-oxadiazole-2-yl)-1-(2-oxo-2-(thiophene-2-yl)ethyl)pyridine-2(1H)-one

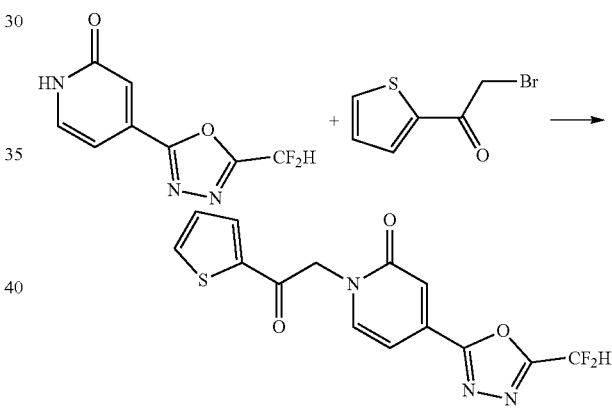

4-(5-(difluoromethyl)-1,3,4-oxadiazole-2-yl)pyridine-2(1H)-one (0.100 g, 0.469 mmol) was dissolved in N,N-dimethylformamide (2.5 mL) at 0° C., after which hydrogenated sodium (60.00%, 0.028 g, 0.704 mmol) was added into the resulting solution, and stirred at the same temperature for 10 minutes. 2-bromo-1-(thiophene-2-yl)ethane-1-one (0.125 g, 0.610 mmol) was added into the reaction mixture, and further stirred at room temperature for two hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; ethyl acetate/hexane=0 to 100%), and concentrated to obtain the title compound (0.110 g, 69.5%) in a white solid form.

$^1$H NMR (400 MHz, CDCl$_3$) δ 7.93 (dd, J=3.8, 0.9 Hz, 1H), 7.77 (dd, J=5.0, 0.8 Hz, 1H), 7.45 (d, J=7.2 Hz, 1H), 7.31 (d, J=1.6 Hz, 1H), 7.22 (dd, J=4.8, 4.0 Hz, 1H), 6.93 (t,

J=51.6 Hz, 1H), 6.93 (dd, J=7.1, 1.9 Hz, 1H), 5.35 (s, 2H); LRMS (ES) m/z 338.3 (M⁺+1).

Example 51: Synthesis of Compound 51, 1-(2-(benzofuran-3-yl)-2-oxoethyl)-4-(5-(difluoromethyl)-1,3,4-oxadiazole-2-yl)pyridine-2(1H)-one

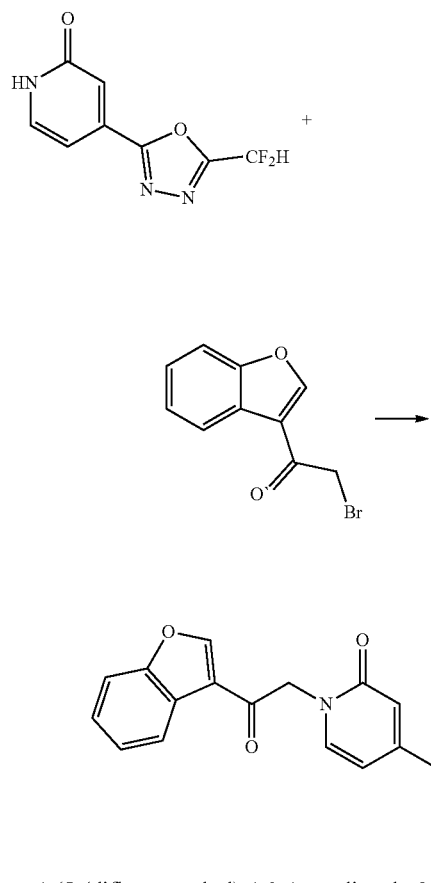

4-(5-(difluoromethyl)-1,3,4-oxadiazole-2-yl)pyridine-2(1H)-one (0.100 g, 0.469 mmol) was dissolved in N,N-dimethylformamide (2.5 mL) at 0° C., after which hydrogenated sodium (60.00%, 0.028 g, 0.704 mmol) was added into the resulting solution, and stirred at the same temperature for 10 minutes. 1-(benzofuran-3-yl)-2-bromoethane-1-one (0.146 g, 0.610 mmol) was added into the reaction mixture, and further stirred at room temperature for two hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO₂, 12 g cartridge; ethyl acetate/hexane=0 to 100%), and concentrated to obtain the title compound (0.085 g, 48.8%) in a white solid form.

¹H NMR (400 MHz, CDCl₃) δ 8.55 (s, 1H), 8.17~8.15 (m, 1H), 7.57 (d, J=11.0 Hz, 1H), 7.51 (d, J=7.1 Hz, 1H), 7.44~7.37 (m, 2H), 7.33 (d, J=1.8 Hz, 1H), 6.93 (t, J=51.6 Hz, 1H), 6.96 (dd, J=7.1, 1.8 Hz, 1H), 5.27 (s, 2H); LRMS (ES) m/z 372.4 (M⁺+1).

Example 52: Synthesis of Compound 52, 4-(5-(difluoromethyl)-1,3,4-oxadiazole-2-yl)-1-(2-methylallyl)pyridine-2(1H)-one

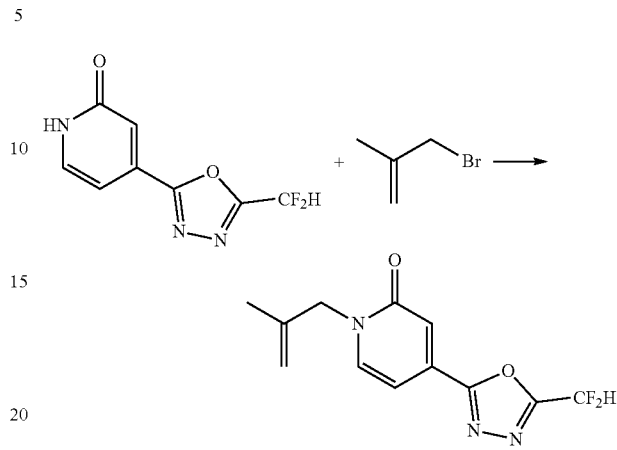

4-(5-(difluoromethyl)-1,3,4-oxadiazole-2-yl)pyridine-2(1H)-one (0.100 g, 0.469 mmol) was dissolved in N,N-dimethylformamide (2.5 mL) at 0° C., after which hydrogenated sodium (60.00%, 0.028 g, 0.704 mmol) was added into the resulting solution, and stirred at the same temperature for 10 minutes. 3-bromo-2-methylprop-1-en (0.061 mL, 0.610 mmol) was added into the reaction mixture, and further stirred at room temperature for two hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO₂, 12 g cartridge; ethyl acetate/hexane=0 to 100%), and concentrated to obtain the title compound (0.067 g, 53.4%) in a white solid form.

¹H NMR (400 MHz, CDCl₃) δ 7.40 (d, J=7.1 Hz, 1H), 7.24 (d, J=1.7 Hz, 1H), 6.91 (t, J=51.6 Hz, 1H), 6.83 (dd, J=7.1, 1.9 Hz, 1H), 4.98 (s, 1H), 4.75 (s, 1H), 4.53 (s, 2H), 1.72 (s, 3H); LRMS (ES) m/z 268.4 (M⁺+1).

Example 53: Synthesis of Compound 53, 4-(5-(difluoromethyl)-1,3,4-oxadiazole-2-yl)-1-(2-oxo-2-(thiophene-2-yl)ethyl)pyridine-2(1H)-one

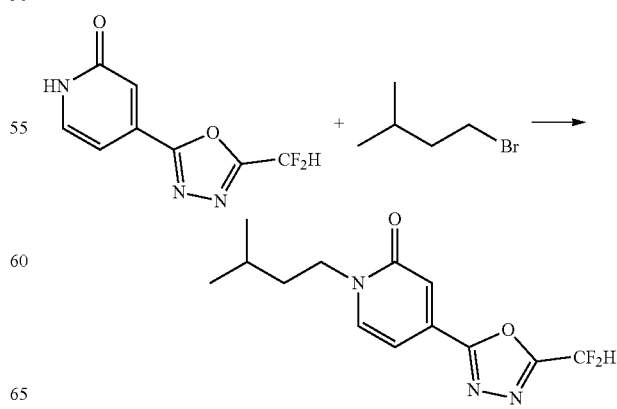

4-(5-(difluoromethyl)-1,3,4-oxadiazole-2-yl)pyridine-2(1H)-one (0.100 g, 0.469 mmol) was dissolved in N,N-dimethylformamide (2.5 mL) at 0° C., after which hydrogenated sodium (60.00%, 0.028 g, 0.704 mmol) was added into the resulting solution, and stirred at the same temperature for 10 minutes. 1-bromo-3-methylbutane (0.073 mL, 0.610 mmol) was added into the reaction mixture, and further stirred at room temperature for two hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; ethyl acetate/hexane=0 to 100%), and concentrated to obtain the title compound (0.035 g, 26.3%) in a white solid form.

$^1$H NMR (400 MHz, CDCl$_3$) δ 7.44 (d, J=7.1 Hz, 1H), 7.23 (d, J=1.8 Hz, 1H), 6.91 (t, J=51.6 Hz, 1H), 6.83 (dd, J=7.1, 1.9 Hz, 1H), 3.98 (dd, J=7.5, 7.5 Hz, 2H), 1.67~1.63 (m, 3H), 0.97 (d, J=6.2 Hz, 6H); LRMS (ES) m/z 284.4 (M$^+$+1).

Example 54: Synthesis of Compound 54, 4-(5-(difluoromethyl)-1,3,4-oxadiazole-2-yl)-1-(3-methylbut-2-en-1-yl)pyridine-2(1H)-one

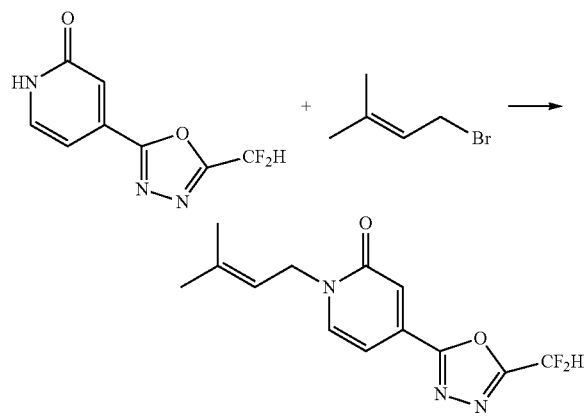

4-(5-(difluoromethyl)-1,3,4-oxadiazole-2-yl)pyridine-2(1H)-one (0.100 g, 0.469 mmol) was dissolved in N,N-dimethylformamide (3 mL) at 0° C., after which hydrogenated sodium (60.00%, 0.028 g, 0.704 mmol) was added into the resulting solution, and stirred at the same temperature for 10 minutes. 1-bromo-3-methylbut-2-en (0.091 g, 0.610 mmol) was added into the reaction mixture, and further stirred at room temperature for 1.5 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; ethyl acetate/hexane=0 to 100%), and concentrated to obtain the title compound (0.026 g, 19.7%) in a white solid form.

$^1$H NMR (400 MHz, CDCl$_3$) δ 7.46 (d, J=7.1 Hz, 1H), 7.22 (d, J=1.5 Hz, 1H), 6.91 (t, J=51.6 Hz, 1H), 6.82 (dd, J=7.1, 1.9 Hz, 1H), 5.35~5.18 (m, 1H), 4.57 (d, J=7.3 Hz, 2H), 1.78 (s, 6H); LRMS (ES) m/z 282.4 (M$^+$+1).

Example 55: Synthesis of Compound 55, 4-(5-(difluoromethyl)-1,3,4-oxadiazole-2-yl)-1-ethylpyridine-2(1H)-one

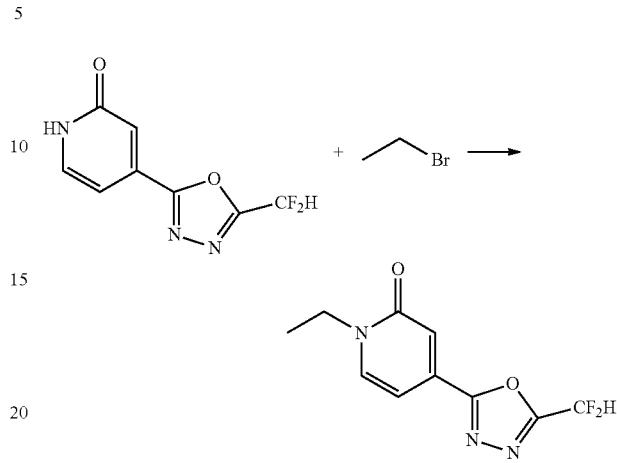

4-(5-(difluoromethyl)-1,3,4-oxadiazole-2-yl)pyridine-2(1H)-one (0.100 g, 0.469 mmol) was dissolved in N,N-dimethylformamide (3 mL) at 0° C., after which hydrogenated sodium (60.00%, 0.028 g, 0.704 mmol) was added into the resulting solution, and stirred at the same temperature for 10 minutes. Bromoethane (0.066 g, 0.610 mmol) was added into the reaction mixture, and further stirred at room temperature for 1.5 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (Si 2, 12 g cartridge; ethyl acetate/hexane=0 to 100%), and concentrated to obtain the title compound (0.011 g, 9.7%) in a white solid form.

$^1$H NMR (400 MHz, CDCl$_3$) δ 7.47 (d, J=7.1 Hz, 1H), 7.26 (d, J=3.2 Hz, 1H), 6.92 (t, J=51.6 Hz, 1H), 6.86 (dd, J=7.0, 1.9 Hz, 1H), 4.05 (q, J=7.2 Hz, 2H), 1.40 (t, J=7.2 Hz, 3H); LRMS (ES) m/z 242.3 (M$^+$+1).

Example 56: Synthesis of Compound 56, 1-(2-(5-chlorothiophene-2-yl)-2-oxoethyl)-4-(5-(difluoromethyl)-1,3,4-oxadiazole-2-yl)pyridine-2(1H)-one

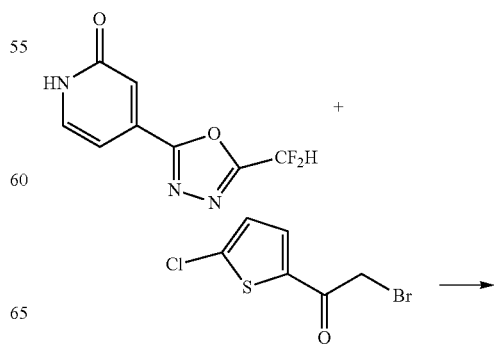

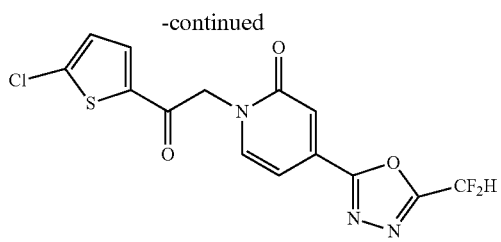

4-(5-(difluoromethyl)-1,3,4-oxadiazole-2-yl)pyridine-2(1H)-one (0.100 g, 0.469 mmol) was dissolved in N,N-dimethylformamide (3 mL) at 0° C., after which hydrogenated sodium (60.00%, 0.028 g, 0.704 mmol) was added into the resulting solution, and stirred at the same temperature for 10 minutes. 2-bromo-1-(5-chlorothiophene-2-yl)ethane-1-one (0.146 g, 0.610 mmol) was added into the reaction mixture, and further stirred at room temperature for 1.5 hours. Solvent was removed from the reaction mixture under reduced pressure, after which water was poured into a resulting concentrate, and an extraction was performed with dichloromethane, then filtered via a plastic filter to remove a solid residue and an aqueous solution layer therefrom, and then concentrated under reduced pressure. A concentrate was purified via column chromatography (SiO$_2$, 12 g cartridge; ethyl acetate/hexane=0 to 100%), and concentrated to obtain the title compound (0.035 g, 20.1%) in a yellow solid form.

$^1$H NMR (400 MHz, CDCl$_3$) δ 7.74 (d, J=4.2 Hz, 1H), 7.44 (d, J=6.7 Hz, 1H), 7.31 (s, 1H), 6.93 (t, J=51.5 Hz, 1H), 7.04 (d, J=3.9 Hz, 1H), 6.94 (dd, J=7.8, 2.2 Hz, 1H), 5.25 (s, 2H); LRMS (ES) m/z 372.3 (M$^+$+1).

Example 57: Synthesis of Compound 57, (R)—N-(2-(4-(5-(difluoromethyl)-1,3,4-oxadiazole-2-yl)-2-oxopyridine-1(2H)-yl)-1-phenylethyl)morpholine-4-carboxamide

[Step 1] Synthesis of tert-butyl (R)-(2-bromo-1-phenylethyl)carbamate

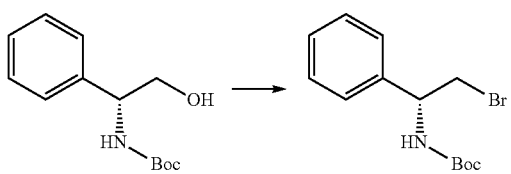 [SMILES: CC(C)(C)OC(=O)N[C@@H](CO)c1ccccc1 ; CC(C)(C)OC(=O)N[C@@H](CBr)c1ccccc1]

Tert-butyl (R)-(2-hydroxy-1-phenylethyl)carbamate (1.000 g, 4.214 mmol), carbon tetrabromide (2.096 g, 6.321 mmol) and triphenylphosphine (1.658 g, 6.321 mmol) were dissolved in dichloromethane (30 mL) at 0° C., after which the resulting solution was stirred at room temperature for 18 hours. Saturated sodium hydrogen carbonate aqueous solution was poured into the reaction mixture, and an extraction was performed with dichloromethane. An organic layer was washed with saturated sodium chloride aqueous solution, then dehydrated with anhydrous magnesium sulfate, then filtered, and then concentrated under reduced pressure. A concentrate was purified via column chromatography (SiO$_2$, 24 g cartridge; ethyl acetate/hexane=0 to 5%), and concentrated to obtain a title compound (0.620 g, 49.0%) in a white solid form.

[Step 2] Synthesis of tert-butyl (R)-(2-(4-(5-(difluoromethyl)-1,3,4-oxadiazole-2-yl)-2-oxopyridine-1(2H)-yl)-1-phenylethyl)carbamate

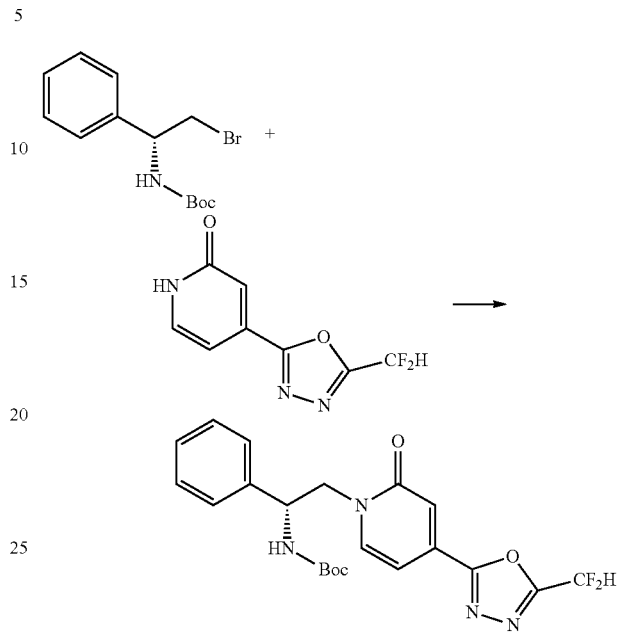

4-(5-(difluoromethyl)-1,3,4-oxadiazole-2-yl)pyridine-2(1H)-one (0.484 g, 2.272 mmol) and hydrogenated sodium (60.00%, 0.091 g, 2.272 mmol) were dissolved in N,N-dimethylformamide (10 mL) at 0° C., after which the tert-butyl (R)-(2-bromo-1-phenylethyl)carbamate (0.620 g, 2.065 mmol) prepared in the step 1 was added into the resulting solution, and stirred at room temperature for 18 hours. Solvent was removed from the reaction mixture under reduced pressure, after which a concentrate was purified via column chromatography (SiO$_2$, 12 g cartridge; ethyl acetate/hexane=50 to 100%, methanol/dichloromethane aqueous solution=5%), and concentrated to obtain a title compound (0.170 g, 19.0%) in a white solid form.

[Step 3] Synthesis of (R)-1-(2-amino-2-phenylethyl)-4-(5-(difluoromethyl)-1,3,4-oxadiazole-2-yl)pyridine-2(1H)-one

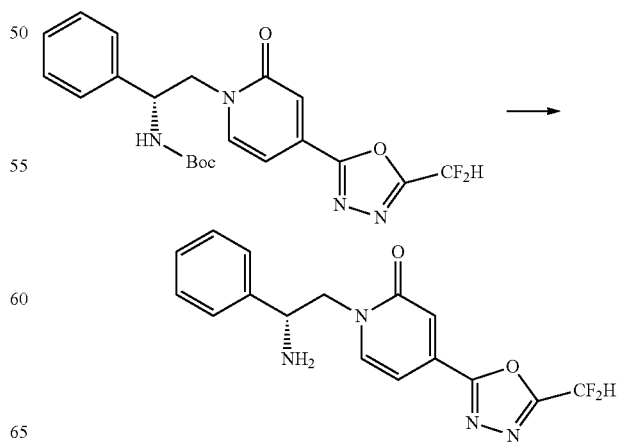

Tert-butyl (R)-(2-(4-(5-(difluoromethyl)-1,3,4-oxadiazole-2-yl)-2-oxopyridine-1(2H)-yl)-1-phenylethyl)carbamate (0.170 g, 0.393 mmol) prepared in the step 2 and trifluoroacetic acid (0.301 mL, 3.931 mmol) were dissolved in dichloromethane (5 mL) at room temperature, after which the resulting solution was stirred at the same temperature for five hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. A title compound was used without an additional purification process (0.095 g, 72.7%, light yellow solid).

[Step 4] Synthesis of Compound 57

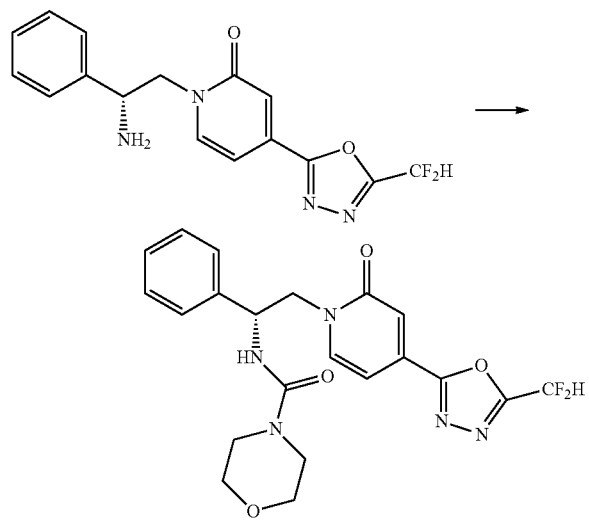

(R)-1-(2-amino-2-phenylethyl)-4-(5-(difluoromethyl)-1,3,4-oxadiazole-2-yl)pyridine-2(1H)-one (0.050 g, 0.150 mmol) prepared in the step 3 and N,N-diisopropylethylamine (0.131 mL, 0.752 mmol) were dissolved in dichloromethane (5 mL) at 0° C., after which triphosgene (0.036 g, 0.120 mmol) was added into the resulting solution, and stirred at the same temperature. Morpholine (0.016 mL, 0.181 mmol) was added into the reaction mixture, and further stirred at the same temperature for 30 minutes. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. A concentrate was purified via column chromatography (SiO$_2$, 4 g cartridge; ethyl acetate/hexane=60 to 100%), and concentrated to obtain a product, after which the resulting product was purified again via chromatography (SiO$_2$, 4 g cartridge; methanol/dichloromethane=0 to 2.5%), and concentrated to obtain a title compound (0.033 g, 49.2%) in a white solid form.

$^1$H NMR (400 MHz, CDCl$_3$) δ 7.39-7.27 (m, 5H), 7.14 (d, 1H, J=7.1 Hz), 7.08-6.80 (m, 3H), 5.28-5.24 (m, 1H), 4.48-4.43 (m, 1H), 4.26 (dd, 1H, J=13.8, 3.2 Hz), 3.72-3.67 (m, 4H), 3.41-3.34 (m, 4H); LRMS (ES) m/z 446.5 (M$^+$+1).

Example 58: Synthesis of Compound 58, (R)—N-(2-(4-(5-(difluoromethyl)-1,3,4-oxadiazole-2-yl)-2-oxopyridine-1(2H)-yl)-1-phenylethyl)thiomorpholine-4-carboxamide 1,1-dioxide

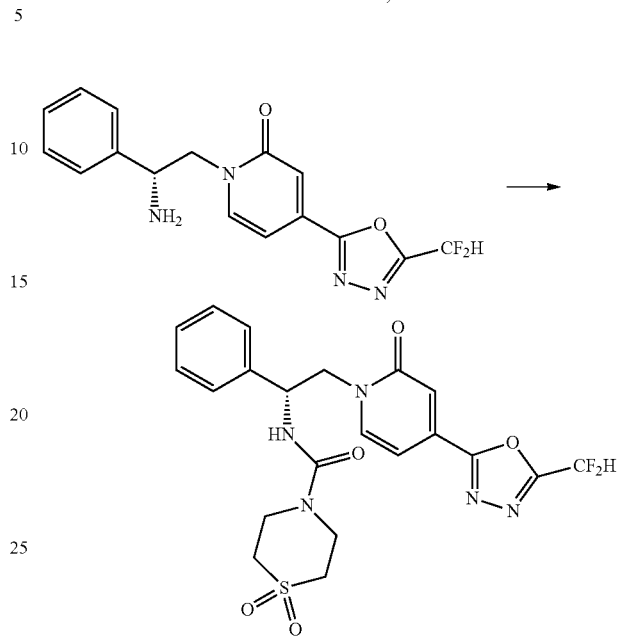

(R)-1-(2-amino-2-phenylethyl)-4-(5-(difluoromethyl)-1,3,4-oxadiazole-2-yl)pyridine-2(1H)-one (0.045 g, 0.135 mmol) prepared in the step 3 for the synthesis of Compound 57, and N,N-diisopropylethylamine (0.118 mL, 0.677 mmol) were dissolved in dichloromethane (5 mL) at 0° C., after which triphosgene (0.032 g, 0.108 mmol) was added into the resulting solution, and stirred at the same temperature. Thiomorpholine 1,1-dioxide (0.022 g, 0.162 mmol) was added into the reaction mixture, and further stirred at the same temperature for 30 minutes. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. A concentrate was purified via column chromatography (SiO$_2$, 4 g cartridge; ethyl acetate/hexane=60 to 100%), and concentrated to obtain a product, after which the resulting product was purified again via chromatography (SiO$_2$, 4 g cartridge; methanol/dichloromethane=0 to 2.5%), and concentrated to obtain a title compound (0.025 g, 37.4%) in a white solid form.

$^1$H NMR (400 MHz, CDCl$_3$) δ 7.51 (d, 1H, J=5.9 Hz), 7.34-7.25 (m, 6H), 7.08-6.82 (m, 2H), 5.21-5.16 (m, 1H), 4.46-4.40 (m, 1H), 4.22 (dd, 1H, J=13.8, 3.4 Hz), 3.90-3.80 (m, 4H), 2.98-2.95 (m, 4H); LRMS (ES) m/z 494.5 (M$^+$+1).

Protocol for Measuring and Analyzing the Activity of the Inventive Compounds

<Example 1> Identification of HDAC Enzyme Activity Inhibition (In Vitro)

A selective HDAC6 inhibitor is important for selectivity of HDAC1 inhibition, which is a cause of side effects. To identify this, HDAC1/6 enzyme selectivity and cell selectivity (HDAC1: histone acetylation/HDAC6: tubulin acetylation) were investigated accordingly.

1. Experimental Method

An HDAC enzyme inhibitory ability of a test material was measured by means of HDAC1 Fluorimetric Drug Discovery Assay Kit (Enzolifesciences: BML-AK511) and HDAC6 human recombinant (Calbiochem: 382180). For an HDAC1 assay, samples were treated at a concentration of 100, 1000 and 10000 nM. For an HDAC6 assay, samples were treated at a concentration of 0.1, 1, 10, 100 and 1000 nM. After such sample treatment, a reaction was continued at 37° C. for 60 minutes, then treated with a developer, and then subjected to reaction at 37° C. for 30 minutes, after which fluorescence intensity (Ex 390, Em 460) was measured by means of FlexStation3 (Molecular device).

2. Experimental Results

The results thereof were as shown in a following table 2.

As shown in the results of searching the HDAC enzyme activity inhibition in the Table 2, 1,3,4-oxadiazole derivatives of the present invention showed an excellent HDAC1/6 enzyme selectivity.

TABLE 2

| compound | HDAC6 (μM) | HDAC1 (μM) |
|---|---|---|
| 1 | 0.082 | ND |
| 2 | 0.065 | ND |
| 3 | 0.210 | ND |
| 4 | 0.514 | ND |
| 5 | 0.040 | ND |
| 6 | 0.456 | ND |
| 7 | 0.364 | ND |
| 8 | 0.253 | ND |
| 9 | 0.247 | ND |
| 10 | 0.217 | ND |
| 11 | 2.248 | ND |
| 12 | 0.631 | ND |
| 13 | 0.306 | ND |
| 14 | 0.108 | ND |
| 15 | 0.074 | ND |
| 16 | 0.952 | ND |
| 17 | 0.507 | ND |
| 18 | 0.509 | ND |
| 19 | 0.351 | ND |
| 20 | 0.257 | ND |
| 21 | 0.381 | ND |
| 22 | 0.427 | ND |
| 23 | 0.598 | ND |
| 24 | 0.284 | ND |
| 25 | 0.239 | ND |
| 26 | 0.272 | ND |
| 27 | 0.726 | ND |
| 28 | 0.156 | ND |
| 29 | 0.261 | ND |
| 30 | 1.794 | ND |
| 31 | 1.097 | ND |
| 32 | 2.422 | ND |
| 33 | 1.266 | ND |
| 34 | 2.316 | ND |
| 35 | 2.212 | ND |
| 36 | 0.935 | ND |
| 37 | 1.297 | ND |
| 38 | 2.395 | ND |
| 39 | 0.900 | ND |
| 40 | 0.945 | ND |
| 41 | 5.180 | ND |
| 42 | 1.909 | ND |
| 43 | 0.236 | ND |
| 44 | 0.382 | ND |
| 45 | 0.290 | ND |
| 46 | 1.127 | ND |
| 47 | ND | ND |
| 48 | 1.666 | ND |
| 49 | 1.593 | ND |
| 50 | 0.238 | ND |
| 51 | 0.284 | ND |
| 52 | 0.377 | ND |
| 53 | 0.388 | ND |

TABLE 2-continued

| compound | HDAC6 (μM) | HDAC1 (μM) |
|---|---|---|
| 54 | 0.663 | ND |
| 55 | 0.284 | ND |
| 56 | 0.126 | ND |
| 57 | 0.301 | ND |
| 58 | 0.358 | ND |

As described in the Table 2 above, it was identified from the results of testing the activity inhibition to HDAC1 and HDAC6 that the inventive 1,3,4-oxadiazole derivative compounds, optical isomers thereof or pharmaceutically acceptable salts thereof show not only an excellent HDAC6 inhibitory activity, but also an excellent selective inhibitory activity of HDAC6 to HDAC1.

The invention claimed is:

1. A 1,3,4-oxadiazole derivative compound represented by a following formula I, optical isomer thereof or pharmaceutically acceptable salt thereof:

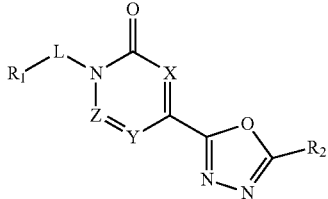

[Formula I]

wherein,

X, Y and Z are each independently $CR_3$ or N;

L is $-(C_1-C_6$ alkylene)-, $-(C_2-C_6$ alkenylene)-, $-(C=O)-(C_1-C_4$ alkylene)-, $-(C=O)O-(C_1-C_4$ alkylene)-, $-(C=O)NH-(C_1-C_4$ alkylene)-, $-O(C=O)-(C_1-C_4$ alkylene)- or a single bond, wherein at least one H of $-(C_1-C_6$ alkylene)-, $-(C_2-C_6$ alkenylene)-, $-(C=O)-(C_1-C_4$ alkylene)-, $-(C=O)O-(C_1-C_4$ alkylene)-, $-(C=O)NH-(C_1-C_4$ alkylene)- and $-O(C=O)-(C_1-C_4$ alkylene)- may be substituted with aryl or heteroaryl;

$R_1$ is hydrogen, $-C_1-C_6$ alkyl, $-C_2-C_6$ alkenyl, $-C_3-C_8$ cycloalkyl, heterocycloalkyl, benzyl, aryl, heteroaryl or $-NR_4R_5$, wherein at least one H of aryl or heteroaryl may be substituted with $-C_1-C_6$ alkyl, $-C_2-C_6$ alkenyl, $-C_1-C_6$ haloalkyl, $-C_1-C_6$ aminoalkyl, $-C_1-C_6$ hydroxyalkyl, $-C_1-C_6$ alkoxy, hydroxy, cyano, halo, nitro, $-CF_2H$, $-CF_3$, $-NR_6R_7$, $-C(=O)-R_8$ or $-S(=O)_2-R_9$;

$R_2$ is $-CF_2H$ or $-CF_3$;

$R_3$ is hydrogen, halo or $-C_1-C_6$ alkyl;

$R_4$ to $R_7$ are each independently H or $-C_1-C_6$ alkyl; and $R_8$ and $R_9$ are each independently H, OH or $-C_1-C_6$ alkyl.

2. The 1,3,4-oxadiazole derivative compound represented by the formula I, optical isomer thereof or pharmaceutically acceptable salt thereof according to claim 1, wherein:

X, Y and Z are each independently $CR_3$ or N;

L is $-(C_1-C_6$ alkylene)-, $-(C_2-C_6$ alkenylene)-, $-(C=O)-(C_1-C_4$ alkylene)-, $-(C=O)O-(C_1-C_4$ alkylene)-, $-(C=O)NH-(C_1-C_4$ alkylene)-, $-O(C=O)-(C_1-C_4$ alkylene)- or a single bond, wherein at least one H of $-(C_1-C_6$ alkylene)-, $-(C_2-C_6$ alkenylene)-, $-(C=O)-(C_1-C_4$ alkylene)-, —(C═O)O—($C_1$-$C_4$ alkylene)-, —(C═O)NH—($C_1$-$C_4$ alkylene)- and —O(C═O)—($C_1$-$C_4$ alkylene)- may be substituted with aryl;

$R_1$ is hydrogen, —$C_1$-$C_6$ alkyl, —$C_2$-$C_6$ alkenyl, heterocycloalkyl, benzyl, aryl, heteroaryl or —$NR_4R_5$, wherein at least one H of aryl or heteroaryl may be substituted with —$C_1$-$C_6$ alkyl, —$C_1$-$C_6$ alkoxy, halo, nitro, —$CF_3$ or —$S(═O)_2$—$R_9$;

$R_2$ is —$CF_2H$ or —$CF_3$;

$R_3$ is hydrogen or halo;

$R_4$ to $R_5$ are each independently —$C_1$-$C_6$ alkyl; and $R_9$ is each independently —$C_1$-$C_6$ alkyl.

3. The 1,3,4-oxadiazole derivative compound represented by the formula I, optical isomer thereof or pharmaceutically acceptable salt thereof according to claim 1, wherein:

X, Y and Z are each independently $CR_3$;

L is —($C_1$-$C_4$ alkylene)-, —($C_2$-$C_4$ alkenylene)-, —(C═O)—($C_1$-$C_2$ alkylene)-, —(C═O)O—($C_1$-$C_2$ alkylene)-, —(C═O)NH—($C_1$-$C_2$ alkylene)-, —O(C═O)—($C_1$-$C_2$ alkylene)- or a single bond, wherein at least one H of —($C_1$-$C_4$ alkylene)-, —($C_2$-$C_4$ alkenylene)-, —(C═O)—($C_1$-$C_2$ alkylene)-, —(C═O)O—($C_1$-$C_2$ alkylene)-, —(C═O)NH—($C_1$-$C_2$ alkylene)- and —O(C═O)—($C_1$-$C_2$ alkylene)- may be substituted with aryl;

$R_1$ is —$C_1$-$C_6$ alkyl, —$C_2$-$C_6$ alkenyl,

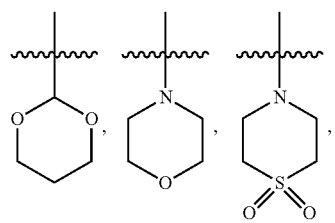

benzyl, phenyl, naphthyl,

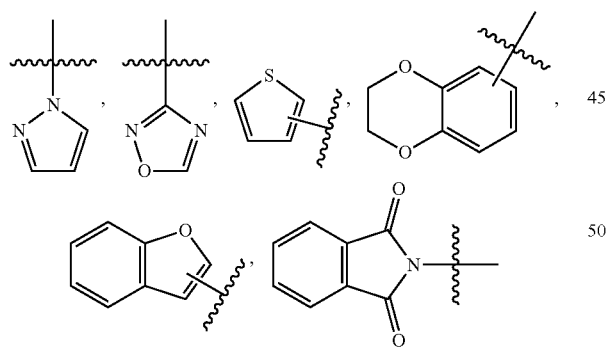

or —$NR_4R_5$, wherein at least one H of phenyl, naphythyl,

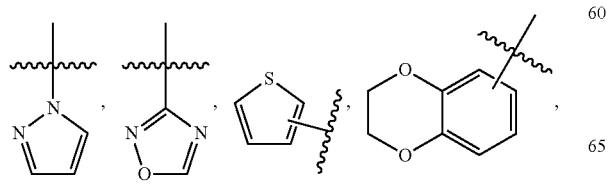

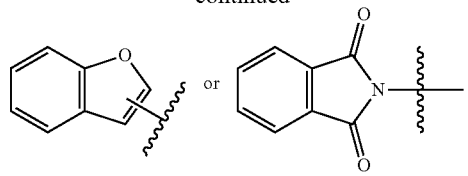

may be substituted with —$C_1$-$C_6$ alkyl, —$C_1$-$C_6$ alkoxy, halo, nitro, —$CF_3$ or —$S(═O)_2$—$R_9$;

$R_2$ is —$CF_2H$ or —$CF_3$;

$R_3$ is hydrogen;

$R_4$ to $R_5$ are each independently —$C_1$-$C_4$ alkyl; and $R_9$ is each independently —$C_1$-$C_4$ alkyl.

4. The 1,3,4-oxadiazole derivative compound represented by the formula I, optical isomer thereof or pharmaceutically acceptable salt thereof according to claim 1, wherein:

X, Y and Z are each independently $CR_3$;

L is —($C_1$-$C_4$ alkylene)-, —($C_2$-$C_4$ alkenylene)-, —(C═O)—($C_1$-$C_2$ alkylene)-, —(C═O)NH—($C_1$-$C_2$ alkylene)-, —O(C═O)—($C_1$-$C_2$ alkylene)- or a single bond, wherein at least one H of —($C_1$-$C_4$ alkylene)-, —($C_2$-$C_4$ alkenylene)-, —(C═O)—($C_1$-$C_2$ alkylene)-, —(C═O)NH—($C_1$-$C_2$ alkylene)- or —O(C═O)—($C_1$-$C_2$ alkylene)- may be substituted with aryl;

$R_1$ is —$C_1$-$C_6$ alkyl, —$C_2$-$C_6$ alkenyl,

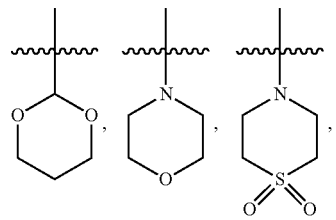

phenyl, naphthyl,

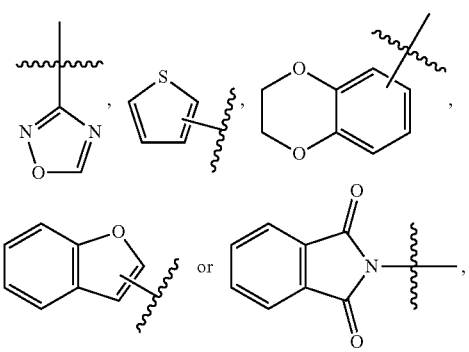

wherein at least one H of phenyl, naphthyl,

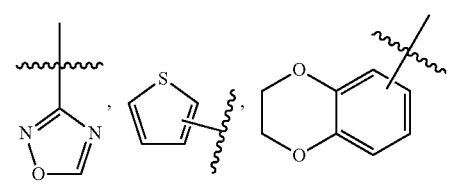

-continued

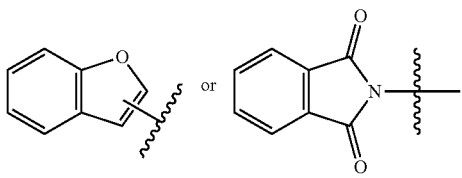

may be substituted with —$C_1$-$C_6$ alkoxy, halo, nitro or —$CF_3$;

$R_2$ is —$CF_2H$; and $R_3$ is hydrogen.

5. The 1,3,4-oxadiazole derivative compound represented by the formula I, optical isomer thereof or pharmaceutically acceptable salt thereof according to claim 1, wherein the compound represented by the formula I above is selected from the compounds as described in a following table:

| Compound | structure |
| --- | --- |
| 1 | 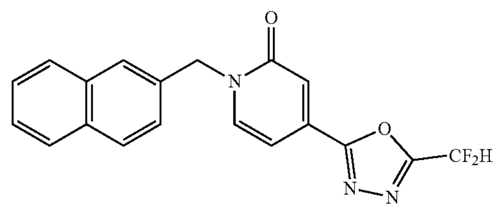 [SMILES: O=c1cc(-c2nnc(C(F)F)o2)ccn1Cc1ccc2ccccc2c1] |
| 2 | 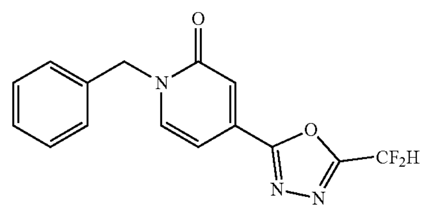 [SMILES: O=c1cc(-c2nnc(C(F)F)o2)ccn1Cc1ccccc1] |
| 3 | 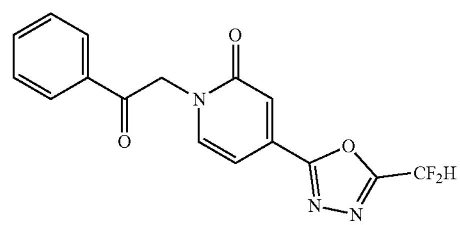 [SMILES: O=C(Cn1ccc(-c2nnc(C(F)F)o2)cc1=O)c1ccccc1] |
| 4 | 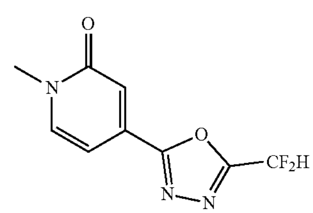 [SMILES: Cn1ccc(-c2nnc(C(F)F)o2)cc1=O] |
| 5 | 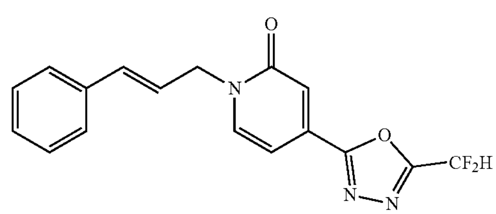 [SMILES: O=c1cc(-c2nnc(C(F)F)o2)ccn1C/C=C/c1ccccc1] |
| 6 | 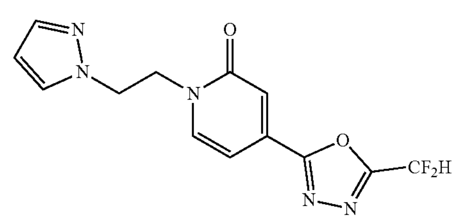 [SMILES: O=c1cc(-c2nnc(C(F)F)o2)ccn1CCn1cccn1] |

-continued

| Compound | structure |
|---|---|
| 7 | (naphthalen-2-yl ketone-CH2-N-pyridinone-oxadiazole-CF2H) |
| 8 | (3,5-dimethoxyphenethyl-N-pyridinone-oxadiazole-CF2H) |
| 9 | (1,3-dioxan-2-yl-ethyl-N-pyridinone-oxadiazole-CF2H) |
| 10 | (2,5-difluorobenzyl-N-pyridinone-oxadiazole-CF2H) |
| 11 | (diethylaminoethyl-N-pyridinone-oxadiazole-CF2H) |
| 12 | (2-chlorobenzyl-N-pyridinone-oxadiazole-CF2H) |
| 13 | (2,4,5-trifluorobenzyl-N-pyridinone-oxadiazole-CF2H) |

-continued
| Compound | structure |
|---|---|
| 14 | 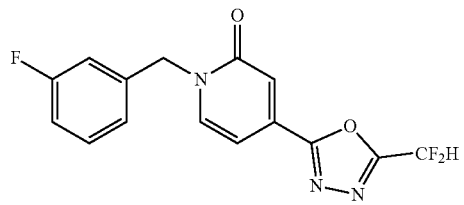 |
| 15 | 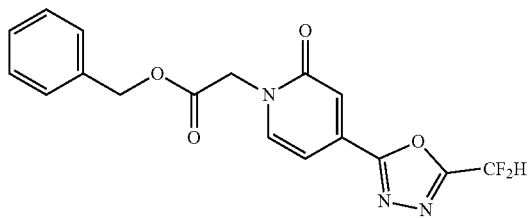 [SMILES: O=C(Cn1ccc(-c2nnc(C(F)F)o2)cc1=O)OCc1ccccc1] |
| 16 | 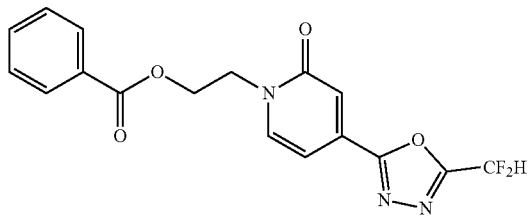 [SMILES: O=C(OCCn1ccc(-c2nnc(C(F)F)o2)cc1=O)c1ccccc1] |
| 17 | 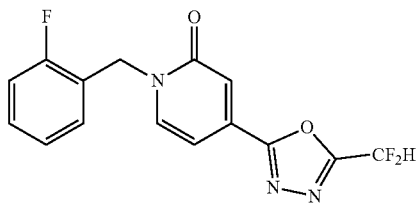 |
| 18 | 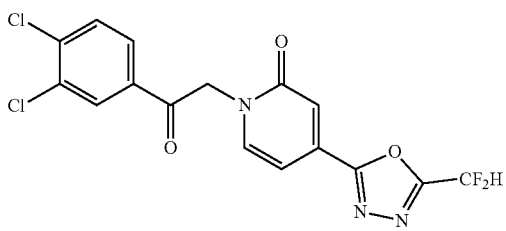 [SMILES: O=C(Cn1ccc(-c2nnc(C(F)F)o2)cc1=O)c1ccc(Cl)c(Cl)c1] |
| 19 | 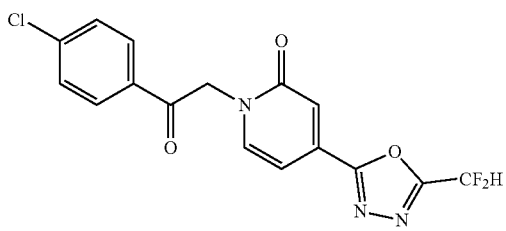 [SMILES: O=C(Cn1ccc(-c2nnc(C(F)F)o2)cc1=O)c1ccc(Cl)cc1] |
| 20 | 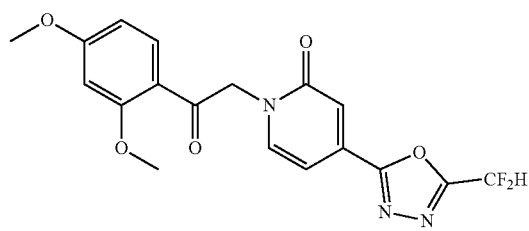 [SMILES: COc1ccc(C(=O)Cn2ccc(-c3nnc(C(F)F)o3)cc2=O)c(OC)c1] |

-continued
| Compound | structure |
|---|---|
| 21 | 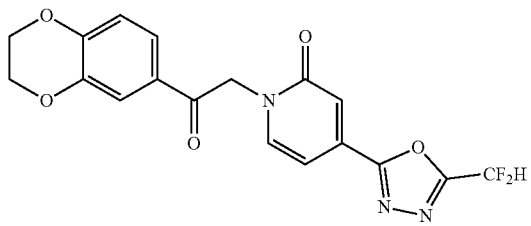 [SMILES: O=C(Cn1ccc(-c2nnc(C(F)F)o2)cc1=O)c1ccc2c(c1)OCCO2] |
| 22 | 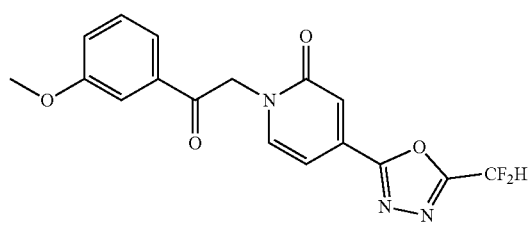 [SMILES: COc1cccc(C(=O)Cn2ccc(-c3nnc(C(F)F)o3)cc2=O)c1] |
| 23 | 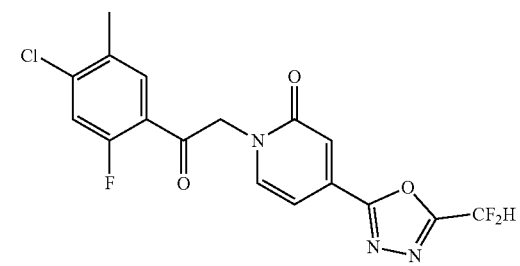 [SMILES: Cc1cc(C(=O)Cn2ccc(-c3nnc(C(F)F)o3)cc2=O)c(F)cc1Cl] |
| 24 | 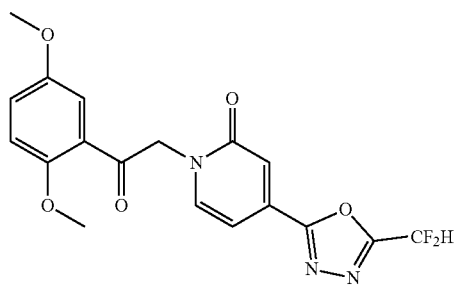 [SMILES: COc1ccc(OC)c(C(=O)Cn2ccc(-c3nnc(C(F)F)o3)cc2=O)c1] |
| 25 | 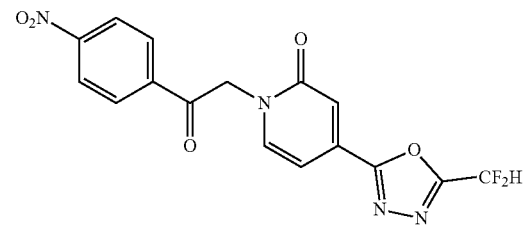 [SMILES: O=C(Cn1ccc(-c2nnc(C(F)F)o2)cc1=O)c1ccc([N+](=O)[O-])cc1] |
| 26 | 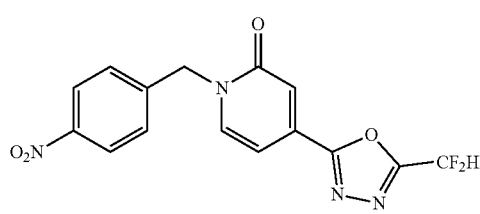 [SMILES: O=c1cc(-c2nnc(C(F)F)o2)ccn1Cc1ccc([N+](=O)[O-])cc1] |

-continued

| Compound | structure |
|---|---|
| 27 | (structure: 1-(2-ethylbutyl)-4-[5-(difluoromethyl)-1,3,4-oxadiazol-2-yl]pyridin-2(1H)-one) |
| 28 | (structure: 1-{[5-(trifluoromethyl)-1,2,4-oxadiazol-3-yl]methyl}-4-[5-(difluoromethyl)-1,3,4-oxadiazol-2-yl]pyridin-2(1H)-one) |
| 29 | (structure: 1-{4-(1,3-dioxoisoindolin-2-yl)butyl}-4-[5-(difluoromethyl)-1,3,4-oxadiazol-2-yl]pyridin-2(1H)-one) |
| 30 | (structure: 1-(2,4,5-trifluorobenzyl)-4-[5-(trifluoromethyl)-1,3,4-oxadiazol-2-yl]pyridin-2(1H)-one) |
| 31 | (structure: 1-(3-fluorobenzyl)-4-[5-(trifluoromethyl)-1,3,4-oxadiazol-2-yl]pyridin-2(1H)-one) |
| 32 | (structure: 1-(2-fluorobenzyl)-4-[5-(trifluoromethyl)-1,3,4-oxadiazol-2-yl]pyridin-2(1H)-one) |
| 33 | (structure: 1-(2,5-difluorobenzyl)-4-[5-(trifluoromethyl)-1,3,4-oxadiazol-2-yl]pyridin-2(1H)-one) |

-continued

| Compound | structure |
|---|---|
| 34 | 4-chlorophenyl-CO-CH₂-N(pyridin-2(1H)-one)-4-(5-(trifluoromethyl)-1,3,4-oxadiazol-2-yl) |
| 35 | 4-(methylsulfonyl)phenyl-CO-CH₂-N(pyridin-2(1H)-one)-4-(5-(trifluoromethyl)-1,3,4-oxadiazol-2-yl) |
| 36 | thiophen-2-yl-CO-CH₂-N(pyridin-2(1H)-one)-4-(5-(trifluoromethyl)-1,3,4-oxadiazol-2-yl) |
| 37 | 5-chlorothiophen-2-yl-CO-CH₂-N(pyridin-2(1H)-one)-4-(5-(trifluoromethyl)-1,3,4-oxadiazol-2-yl) |
| 38 | benzofuran-3-yl-CO-CH₂-N(pyridin-2(1H)-one)-4-(5-(trifluoromethyl)-1,3,4-oxadiazol-2-yl) |
| 39 | phenyl-C(=O)-O-CH₂CH₂-N(pyridin-2(1H)-one)-4-(5-(trifluoromethyl)-1,3,4-oxadiazol-2-yl) |
| 40 | benzyl-O-C(=O)-CH₂-N(pyridin-2(1H)-one)-4-(5-(trifluoromethyl)-1,3,4-oxadiazol-2-yl) |

-continued
| Compound | structure |
|---|---|
| 41 | 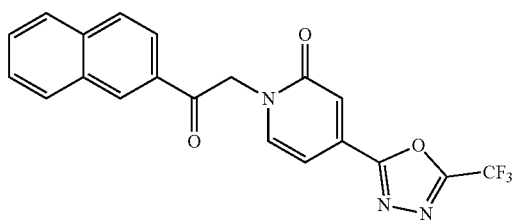 [SMILES: O=C(Cn1ccc(-c2nnc(C(F)(F)F)o2)cc1=O)c1ccc2ccccc2c1] |
| 42 | 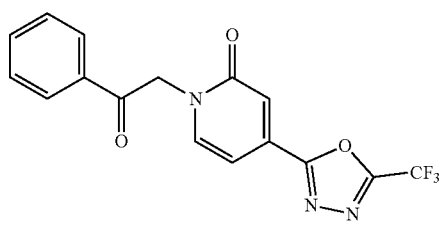 [SMILES: O=C(Cn1ccc(-c2nnc(C(F)(F)F)o2)cc1=O)c1ccccc1] |
| 43 | 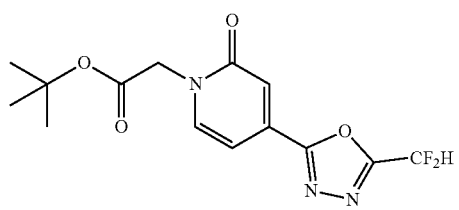 [SMILES: CC(C)(C)OC(=O)Cn1ccc(-c2nnc(C(F)F)o2)cc1=O] |
| 44 | 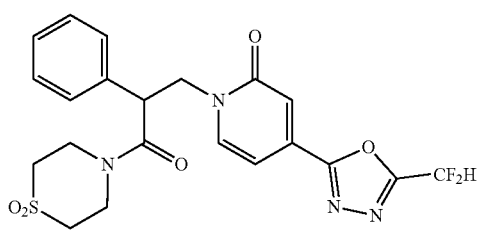 [SMILES: O=C(C(Cn1ccc(-c2nnc(C(F)F)o2)cc1=O)c1ccccc1)N1CCS(=O)(=O)CC1] |
| 45 | 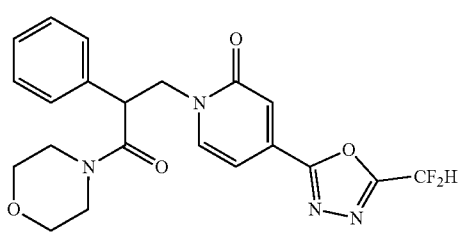 [SMILES: O=C(C(Cn1ccc(-c2nnc(C(F)F)o2)cc1=O)c1ccccc1)N1CCOCC1] |
| 46 | 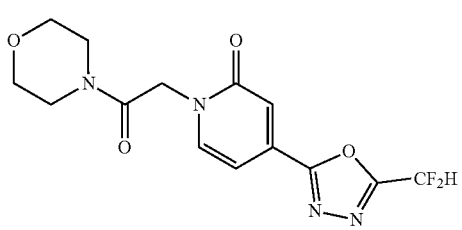 [SMILES: O=C(Cn1ccc(-c2nnc(C(F)F)o2)cc1=O)N1CCOCC1] |
| 47 | 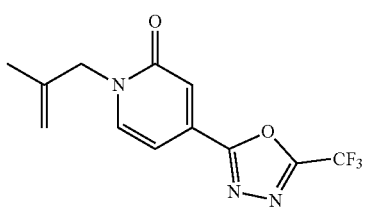 [SMILES: C=C(C)Cn1ccc(-c2nnc(C(F)(F)F)o2)cc1=O] |

-continued
| Compound | structure |
|---|---|
| 48 | 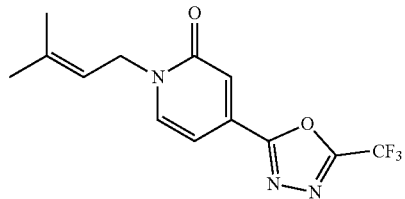 [SMILES: CC(C)=CCn1ccc(-c2nnc(C(F)(F)F)o2)cc1=O] |
| 49 | 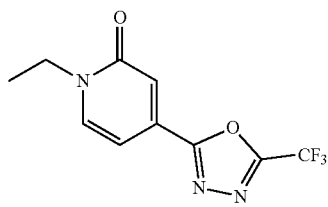 [SMILES: CCn1ccc(-c2nnc(C(F)(F)F)o2)cc1=O] |
| 50 | 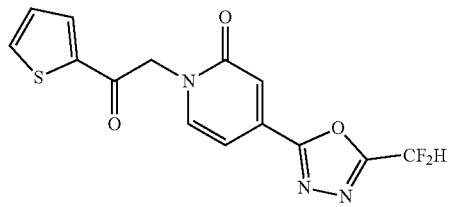 [SMILES: O=C(Cn1ccc(-c2nnc(C(F)F)o2)cc1=O)c1cccs1] |
| 51 | 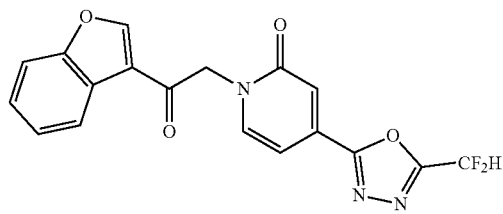 [SMILES: O=C(Cn1ccc(-c2nnc(C(F)F)o2)cc1=O)c1coc2ccccc12] |
| 52 | 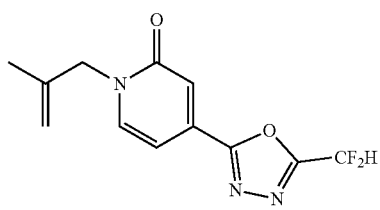 [SMILES: C=C(C)Cn1ccc(-c2nnc(C(F)F)o2)cc1=O] |
| 53 | 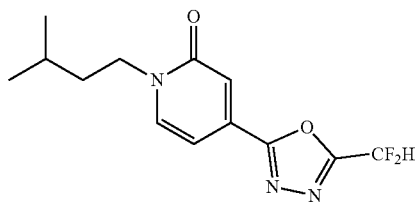 [SMILES: CC(C)CCn1ccc(-c2nnc(C(F)F)o2)cc1=O] |
| 54 | 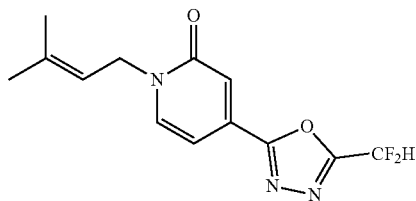 [SMILES: CC(C)=CCn1ccc(-c2nnc(C(F)F)o2)cc1=O] |

| Compound | structure |
|---|---|
| 55 | (1-ethyl-2-oxo-pyridin-4-yl connected to 1,3,4-oxadiazole-CF₂H) |
| 56 | (5-chlorothiophen-2-yl-C(=O)-CH₂-N of pyridinone-4-(1,3,4-oxadiazole)-CF₂H) |
| 57 | (phenyl-CH(NHC(=O)-morpholine)-CH₂-N-pyridinone-4-(1,3,4-oxadiazole)-CF₂H) |
| 58 | (phenyl-CH(NHC(=O)-thiomorpholine-1,1-dioxide)-CH₂-N-pyridinone-4-(1,3,4-oxadiazole)-CF₂H) |

6. The 1,3,4-oxadiazole derivative compound represented by the formula I, optical isomer thereof or pharmaceutically acceptable salt thereof according to claim 5, wherein the compound represented by the formula I above is selected from the compounds selected from the group consisting of compounds 1, 2, 3, 5, 7, 8, 9, 10, 13, 14, 15, 20, 21, 24, 25, 26, 28, 29, 43, 44, 45, 50, 51, 52, 53, 55, 56, 57 and 58.

7. A pharmaceutical composition for preventing or treating histone deacetylase 6 activity-related diseases, comprising the 1,3,4-oxadiazole derivative compound represented by the formula I, optical isomer thereof or pharmaceutically acceptable salt thereof according to claim 1 as an active ingredient.

8. The pharmaceutical composition according to claim 7, wherein histone deacetylase 6 activity-related diseases are at least one selected from the group consisting of infectious diseases; neoplasm; internal secretion; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, and chromosomal aberration.

9. A method for treating or preventing histone deacetylase 6 activity-related diseases, comprising administering a therapeutically effective amount of the 1,3,4-oxadiazole derivative compound represented by the formula I, optical isomer thereof or pharmaceutically acceptable salt thereof according to claim 1.

* * * * *

UNITED STATES PATENT AND TRADEMARK OFFICE
CERTIFICATE OF CORRECTION

PATENT NO. : 11,958,844 B2
APPLICATION NO. : 17/263333
DATED : April 16, 2024
INVENTOR(S) : Chang Sik Lee et al.

It is certified that error appears in the above-identified patent and that said Letters Patent is hereby corrected as shown below:

On the Title Page

Column 1, Applicant Item (71):
After Chong Kun Dang Pharmaceutical Corp., delete "Soul" and insert -- Seoul --.

Column 2, Other Publications, Line 4:
Delete "mededlineplus/" and insert -- medlineplus/ --.

In the Claims

Column 89, Line 57, in Claim 3:
Delete "naphythyl," and insert -- naphthyl, --.

Signed and Sealed this
Twentieth Day of August, 2024

Katherine Kelly Vidal
*Director of the United States Patent and Trademark Office*